US010562913B2

(12) United States Patent
Delcamp et al.

(10) Patent No.: US 10,562,913 B2
(45) Date of Patent: Feb. 18, 2020

(54) INDOLIZINE-BASED DYES FOR DYE-SENSITIZED SOLAR CELL

(71) Applicant: University of Mississippi, University, MS (US)

(72) Inventors: Jared Delcamp, Oxford, MS (US); Aron Huckaba, Oxford, MS (US)

(73) Assignee: University of Mississippi, University, MS (US)

( * ) Notice: Subject to any disclaimer, the term of this patent is extended or adjusted under 35 U.S.C. 154(b) by 151 days.

(21) Appl. No.: 15/500,480

(22) PCT Filed: Jul. 30, 2015

(86) PCT No.: PCT/US2015/042990
§ 371 (c)(1),
(2) Date: Jan. 30, 2017

(87) PCT Pub. No.: WO2016/019182
PCT Pub. Date: Feb. 4, 2016

(65) Prior Publication Data
US 2017/0226125 A1    Aug. 10, 2017

Related U.S. Application Data

(60) Provisional application No. 62/031,031, filed on Jul. 30, 2014.

(51) Int. Cl.
| C07D 495/04 | (2006.01) |
| C07D 471/04 | (2006.01) |
| C07D 471/16 | (2006.01) |
| H01G 9/20 | (2006.01) |

(52) U.S. Cl.
CPC ......... *C07D 495/04* (2013.01); *C07D 471/04* (2013.01); *H01G 9/2031* (2013.01)

(58) Field of Classification Search
CPC .. C07D 495/04; C07D 471/04; C07D 471/16; H01G 9/2031
See application file for complete search history.

(56) References Cited

U.S. PATENT DOCUMENTS 2,706,193 A * 4/1955 Sprague .................. C09B 23/02
544/300
2006/0130249 A1 6/2006 Ikeda et al.

OTHER PUBLICATIONS

Liu et al., 18(6) Chemistry—A European Journal, 1599-1603 (2012) (CAS Abtract) (Year: 2012).*
Danac, R et al. "D.C. electric conduction mechanism of some newly synthesized indolizine derivatives in thin films", Materials Chemistry and Physics. 2012. vol. 134, pp. 1042-1048.
Delcamp, JH et al. "The Molecular Engineering of Organic Sensitizers for Solar-Cell Applications", Angew. Chem. Int. Ed. 2013. vol. 52, pp. 376-380.
Mishra, A et al. "Metal-Free Organic Dyes for Dye-Sensitized Solar Cells: From Structure: Property Relationships to Design Rules". Angew. Chern. Int. Ed. 2013. vol. 52. pp. 376-380.
Brogdon, et al., A Computational and Experimental Study of Thieno[3,4-b]thiophene as a Proaromatic p-Bridge in Dye-Sensitized Solar Cells; Chem. Eur. J. 2016, 22, 694-703.
Brogdon, et al., Toward tightly bound carboxylic acid-based organic dyes for DSCs: relative TiO2 binding strengths of benzoic acid, cyanoacrylic acid, and conjugated double carboxylic acid anchoring dyes; Synthetic Metals 222 (2016) 66-75.
Cheema, et al., Harnessing Photovoltage: Effects of Film Thickness, TiO2 Nanoparticle Size, MgO and Surface Capping with DSCs; ACS Appl. Mater. Interfaces 2017, 9, 3050-3059.
Delcamp, et al., Modulating dye E(S+/S*) with efficient heterocyclic nitrogen containing acceptors for DSCs; Chem. Commun., 2012, 48, 2295-2297.
Delcamp, et al., The Role of p Bridges in High-Efficiency DSCs Based on Unsymmetrical Squaraines; Chem. Eur. J. 2013, 19, 1819-1827.
Dualeh, et al., Near-infrared sensitization of solid-state dye-sensitized solar cells with a squaraine dye; Applied Physics Letters 100, (2012) 173512.
Dualeh, et al., Solid-State Dye-Sensitized Solar Cells Using a Novel Class of Ullazine Dyes as Sensitizers; Adv. Energy Mater. 2013, 3, 496-504.
Huckaba, et al., A low recombination rate indolizine sensitizer for dye-sensitized solar cells; Chem. Commun., 2016, 52, 8424-8427.
Huckaba, et al., Indolizine-Based Donors as Organic Sensitizer Components for Dye-Sensitized Solar Cells; Adv. Energy Mater. 2015, 5, 1401629.
Huckaba, et al., Molecular Design Principles for Near-Infrared Absorbing and Emitting Indolizine Dyes; Chem. Eur. J. 2016, 22, 15536-15542.
Liyanage, et al., Thieno[3,4-b]pyrazine as an Electron Deficient π-Bridge in D-A-π-A DSCs; ACS Appl. Mater. Interfaces 2016, 8, 5376-5384.
Matthew, et al., Synthesis, characterization and ab initio investigation of a panchromatic ullazine-porphyrin photosensitizer for dye-sensitized solar cells; J. Mater. Chem. A, 2016, 4, 2332-2339.
Yum, et al., Blue-Coloured Highly Efficient Dye-Sensitized Solar Cells by Implementing the Diketopyrrolopyrrole Chromophore; Scientificreports; Aug. 15, 2013; pp. 1-8.

* cited by examiner

*Primary Examiner* — Timothy R Rozof
(74) *Attorney, Agent, or Firm* — Stites & Harbison PLLC; Sean P. Ritchie; Richard S. Myers, Jr.

(57) ABSTRACT

Compounds for use as sensitizer dyes in dye-sensitized solar cells.

17 Claims, 5 Drawing Sheets

US 10,562,913 B2

INDOLIZINE-BASED DYES FOR DYE-SENSITIZED SOLAR CELL

RELATED APPLICATIONS

This application claims priority from International Patent Application No. PCT/US15/42990, filed Jul. 30, 2015, which claims priority to provisional 62/031,031 filed Jul. 30, 2014, the entire disclosures of which are incorporated herein by this reference.

GOVERNMENT SUPPORT

This invention was made with government support under award number EPS-0903787 awarded by the National Science Foundation. The government has certain rights in the invention.

TECHNICAL FIELD

The presently-disclosed subject matter relates to compounds for use as sensitizer dyes in dye-sensitized solar cells. In particular, the presently-disclosed subject matter relates to indolizine-based sensitizers for use in dye-sensitized solar cells.

Thus, the present invention generally relates to visible absorbing or near infrared organic dyes for a dye-sensitized solar cell.

Additionally, the present invention generally relates to an organic dye for a dye-sensitized solar cell that comprises a donor-π-bridge acceptor configuration.

Additionally, the present invention relates to DCS devices with a fully conjugated planar nitrogen-containing donor, indolizine, in model visible light absorbing systems.

Additionally, the present invention relates to a dye-sensitized solar cell that comprises a dye of the present invention.

Additionally, the present invention related to efficient D-π-A dyes.

BACKGROUND AND SUMMARY OF THE INVENTION

Dye-sensitized solar cells (DSCs) have undergone continuous improvements since their introduction in 1991. DSCs have already extended into the solar energy conversion market due to their high solar-to-electric power conversion efficiencies (PCEs) and relative affordability. Despite their success so far, several key aspects of DSCs could benefit from additional improvements, including conversion of near-IR (NIR) photons and price of sensitizers. Often cited as cost-effective alternatives to metal-based sensitizers, organic sensitizers have been a key focus within DSC development. These sensitizers have tunability and have been demonstrated to productively utilize NIR photons up to 1000 nm. Organic sensitizers have seen continuous improvements leading to PCEs of >12% since the inception of DSCs.

The most common organic dye structure is the donor-π bridge-acceptor (D-π-A) configuration. Research with regard to the donor fragment has proven instrumental in increasing organic sensitizer-based DSC PCE values to >10%. High-efficiency NIR absorbing D-π-A dyes require balanced donor and acceptor strengths to avoid non-beneficial energy level perturbations. Frequently, strongly electron deficient motifs (acceptors) result in excited-state oxidation potentials that are too stabilized for electron injection into the $TiO_2$ conduction band (CB) rendering these dyes non-functional. Accordingly, there is a need for stronger organic electron-donor materials to be matched with many of the common electron deficient DSC π-bridge-acceptor motifs. Embodiments of the present invention help meet these needs with fully-conjugated planar nitrogen-containing donor, indolizine, in model visible light absorbing systems (FIG. 1).

Nearly all organic sensitizers with >10% PCE utilize arylamine donors, either as triphenylamine, diphenylamine, or indoline. However, these donor systems are not ideal since the electron donation strength is mitigated by three main factors: (1) weak donation directionality to the dye acceptor, (2) large energy barriers to charge transfer due to the breaking of phenyl resonance stabilization energy to access the dye excited-state, and (3) non-optimal nitrogen lone pair orbital alignment with the dye π-conjugated system due to sterically induced twist angles. These mitigating factors can be substantially reduced through designing planar, fully-conjugated nitrogen-containing donor building blocks for dyes, such as indolizine-based donors. When compared computationally to triphenylamine (TPA) and diphenylamine (or indoline) based donors, dramatic improvements in nitrogen-substituent twist angles are observed. TPA shows a substantial 43° dihedral angle and indoline shows a significantly improved 23° dihedral angle. However, indolizine shows an ideal planar nitrogen-substituent bond angle. Additionally, the nitrogen lone-pair of indolizine may donate either into the 6 or 5-member ring and productively deliver the donated electron pair to the π-bridge according to valence bond theory which improves donor directionality. Given these desirable properties and a remarkably rapid, high-yielding donor synthesis (1-step in many cases), embodiments of the present invention include dyes with indolizine donors for comparison to the properties of TPA and indoline donor-based dyes with identical simple π-bridges and acceptors to clearly illustrate the effects of changing donor functionality.

DESCRIPTION OF THE INVENTION

Figure 1:
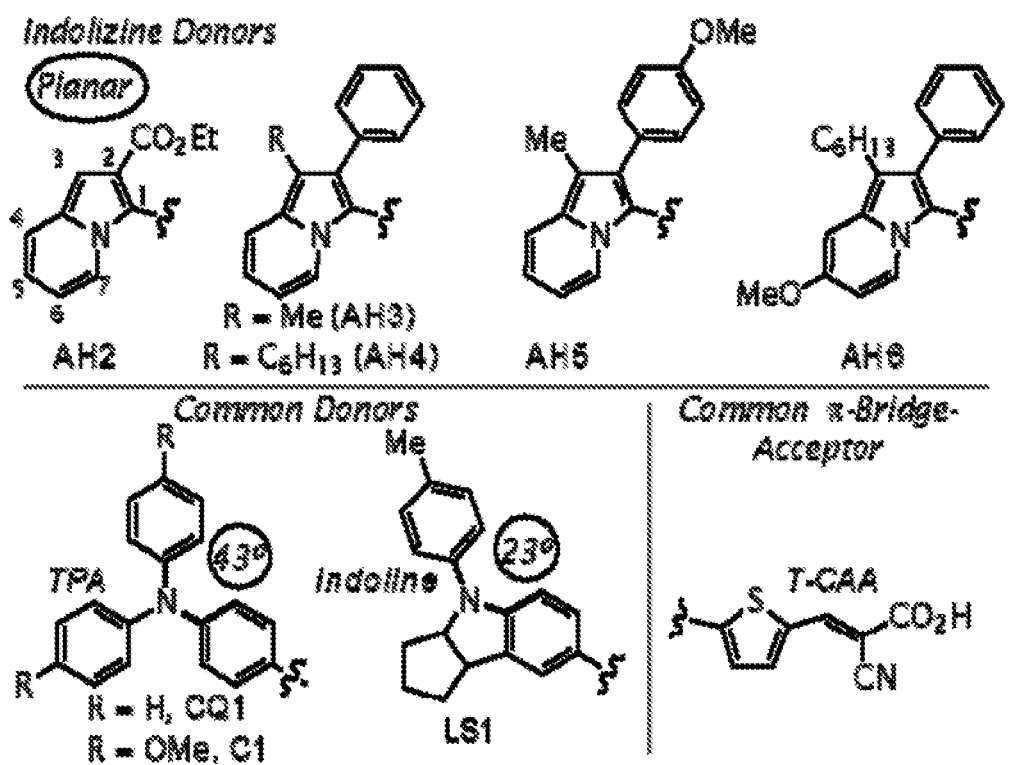
FIG. 1 shows examples indolizine-based donors of the present invention with D-π-A dye components (top) with a common thiophene π-bridge-cyanoacrylic acid acceptor (T-CAA, bottom right). Common all-organic donor functionality (bottom left) with nitrogen-aryl bond dihedral angles calculated after DFT geometry optimization with a B3LYP functional and 6-311G(d,p) basis set.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes novel organic dyes (as sensitizer components, for example) for dye-sensitized solar cells. Embodiments of the present dyes have relatively facile synthesis, a high electron donation strength when compared with state-of-the-art organic donors, and exhibit excellent DSC device performance.

Embodiments of the present dyes are donor molecules that are indolizine-based. Indolizine is a fully conjugated, planar donor, which can be coarse or fine-tuned through electronically active substituents. Accordingly, embodiments of the present dyes include characteristics that can be tuned by altering the substituents bound to a dye's subunits.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds.

Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "alkoxyalkyl" specifically refers to an alkyl group that is substituted with one or more alkoxy groups, as described below. When "alkyl" is used in one instance and a specific term such as "alkoxy" is used in another, it is not meant to imply that the term "alkyl" does not also refer to specific terms such as "alkoxy" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term. The term "alkyl" is inclusive of "cycloalkyl."

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The terms "amine" or "amino" as used herein are represented by a formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein. In specific embodiments amine refers to any of NH$_2$, NH(alkyl), NH(aryl), N(alkyl)$_2$, N(alkyl)(aryl), and N(aryl)$_2$.

The term "aryl" as used herein is a group that contains any carbon-based aromatic group including, but not limited to, benzene, naphthalene, phenyl, biphenyl, phenoxybenzene, thiophene, furan, pyrrole, and the like. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

As used herein, the term 'donor' is defined as a region of a dye which is electron rich in relation to the rest of the dye. A donor is typically attached to either a pi-bridge or an acceptor. Upon light absorption, a donor will transfer charge as electron density either through a pi-bridge or directly to an acceptor. After charge transfer the donor region contains the majority of the positive charge. Within a DSC device, donors are typically the region primarily interacting with the redox shuttle during dye regeneration.

As used herein, the term 'acceptor' or 'electron acceptor' is defined as a region of a dye which is electron deficient in relation to the rest of the dye. An acceptor is typically attached to either a pi-bridge or a donor. Upon light absorption an acceptor will transfer charge as hole density either through a pi-bridge or directly to a donor. After charge transfer the acceptor region contains the majority of the negative charge. Within a DSC device, acceptors are typically in contact with or anchored directly to the semiconducting oxide.

As used herein, the term 'π-bridge' is defined as a region of a dye which is electron neutral in relation to the rest of the dye. A pi-bridge is typically attached in conjugation with both a donor and an acceptor region of a dye. Upon light absorption a pi-bridge allows a charge transfer event to occur by allowing charge to pass between the donor and acceptor regions. After charge transfer, the pi-bridge region may contain either a positive or negative charge.

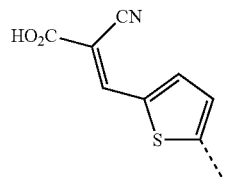

The presently-disclosed subject matter also includes derivatives of any of the compounds described herein. As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds.

The compounds described herein can contain one or more double bonds and, thus, potentially can give rise to cis/trans (E/Z) isomers, as well as other conformational isomers. Unless stated to the contrary, the invention includes all such possible isomers, as well as mixtures of such isomers. Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The present compounds donate electrons upon being activated by electromagnetic radiation. In some embodiments the compounds are activated by radiation that is in the near-infrared spectrum, in the visible spectrum, in the ultra-violet spectrum, or a combination thereof.

The presently-disclosed subject matter also includes methods for making the present compounds. The present compounds exhibit the superior ability to be synthesized in relatively few chemical steps. For instance, some embodiments of the present compounds can be synthesized by about three, four, or five steps. This represents a simpler, and consequently more cost-effective, synthesis method when compared to synthesis methods of known solar cell dyes.

Further still, the presently-disclosed subject matter also includes dye-sensitized solar cells (DSCs) that comprise any of the compounds described herein. The structures of the present DSCs are not particularly limited so long as they permit the dyes to function for their intended purpose. For instance, an exemplary DSC is described in International Patent Application Publication No. WO 2011/0118375 to Jin et al., which is incorporated herein in its entirety. In some embodiments the dye-sensitized solar cell comprises a first electrode, a second electrode that includes one of the presently-disclosed compounds, and an electrolyte disposed between the first electrode and the second electrode. In some embodiments the first electrode includes a cathode and the second electrode includes an anode. In some embodiments the second electrode includes $TiO_2$ particles that are coated and/or embedded with the presently-disclosed dye compounds.

In some embodiments the electrolyte is selected from MeCN or valeronitrile solutions that comprise $I^-/I_3^-$ or $Co^{+2}/Co^{+3}$ redox shuttles present. In other embodiments the electrolyte is selected from poly(ethylene oxide) (PEO), poly(propylene oxide) (PPO), poly(ethylene imine) (PEI), poly(ethylene sulphide) (PES), poly(vinyl acetate) (PVAc), poly(ethylene succinate) (PESc) and combinations thereof.

Embodiments of the presently-described dye-sensitized solar cells can exhibit superior and unexpected power conversion efficiencies (PCEs) when compared to known solar cells. Specific embodiments of the present solar cells exhibit PCEs of about 4%, 5%, 6%, 7%, 8%, 9%, 10%, 11%, 12%, 13%, 14%, 15%, 16%, 17%, 18%, 19%, or 20%. Other embodiments include PCEs of greater than about 20%.

One embodiment of the present invention is visible absorbing or near infrared dyes of the following formula:

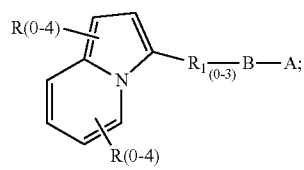

wherein each R is optionally substituted and independently selected from halogen, H, alkyl, amino, O(alkyl), $CO_2$alkyl, aryl, aryl-$R_{2(0-2)}$, or alkyl-$R_{2(0-2)}$;

$R_1$ is alkyl, cycloalkyl, phenyl, alkene or alkyne; wherein when $R_1$ is aryl it can optionally cyclize with one R to form an additional ring;

$R_2$ is halogen, H, alkyl, amino, O(alkyl), aryl, aryl-$R_{3(0-2)}$, or alkyl-$R_{3(0-2)}$;

$R_3$ is halogen, H, alkyl, amino, O(alkyl), or aryl;

B is a π-bridge; and A is an acceptor.

These dyes are useful as organic sensitizer components for dye-sensitized solar cells.

In other embodiments of the present invention, aryl in $R_1$ is substituted or unsubstituted phenyl.

In other embodiments of the present invention, the dye is of the following formula:

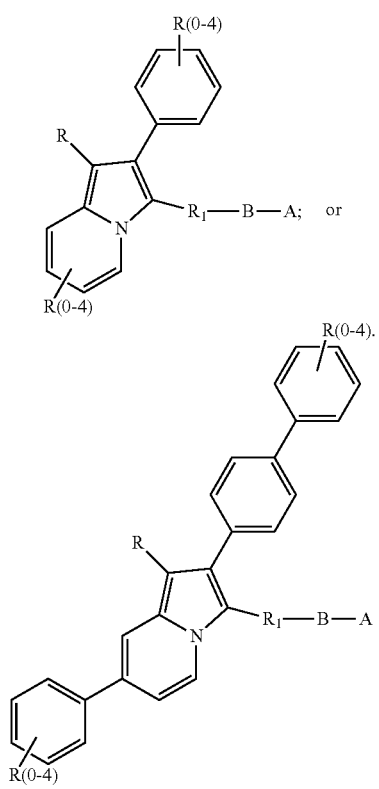

In other embodiments of the present invention, the dye may be tetracyclic. For example, the dye may be of the following formula:

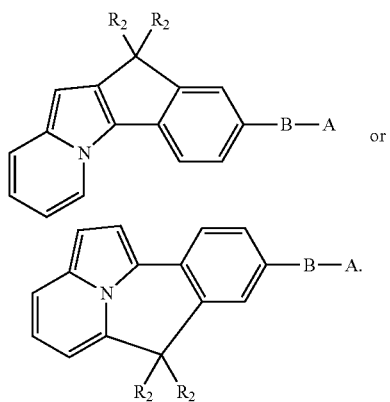

In other embodiments of the present invention, the R groups are independently selected from CO$_2$Et, phenyl, hexyl, pentyl, methyl, O(methyl), and

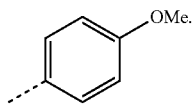

In other embodiments of the present the dye is of the following formula:

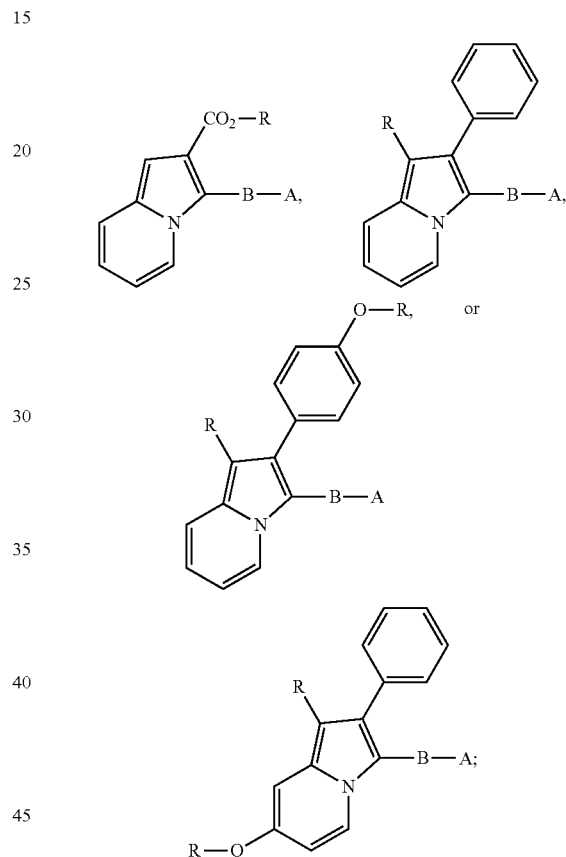

wherein R is alkyl.

Examples of the electron acceptor specifically includes the following:

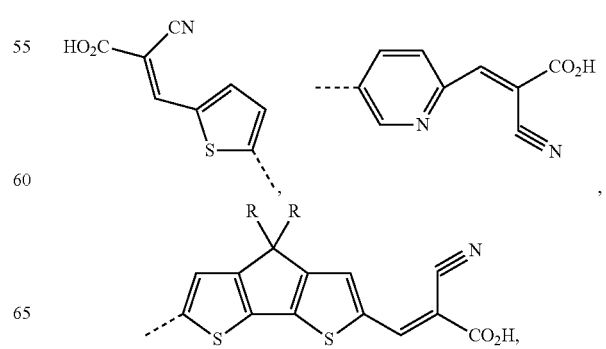

-continued
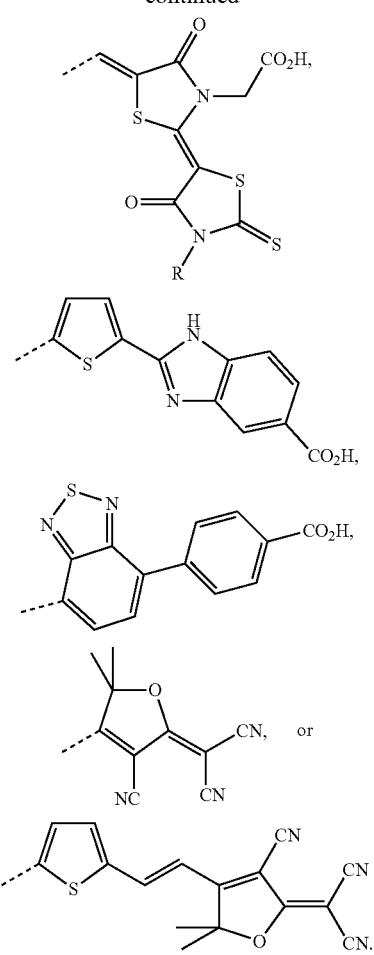
The following are acceptor examples, which can be used in accordance with the present invention:
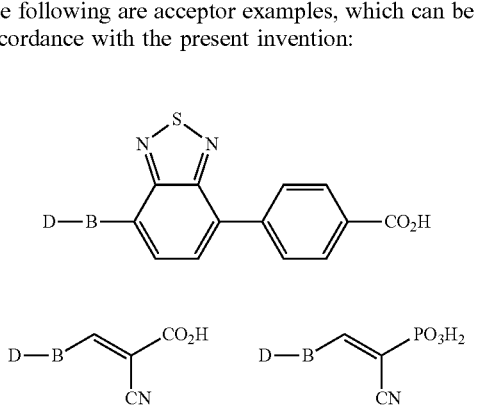
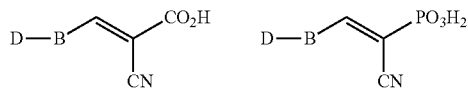
D = donor
B = n-bridge
The following are non-limiting examples of the π-bridge:
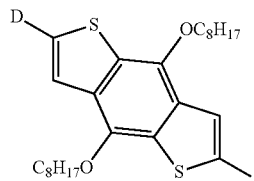
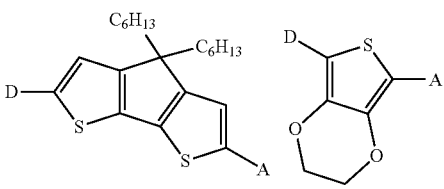
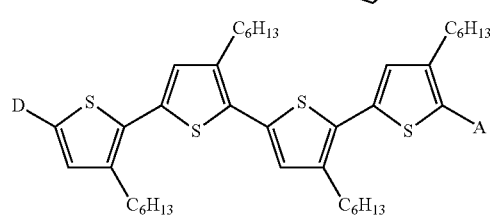
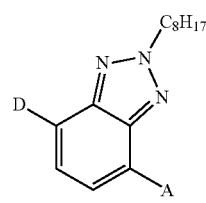
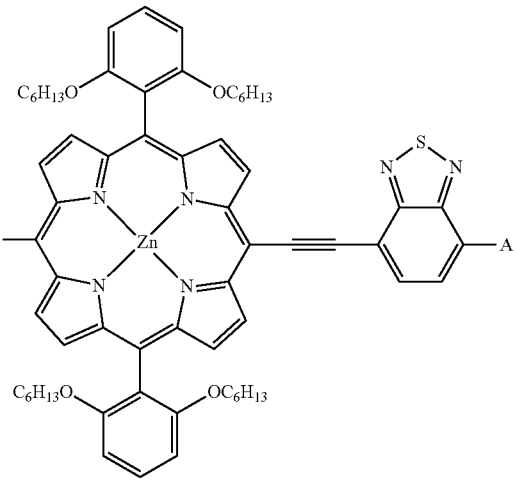
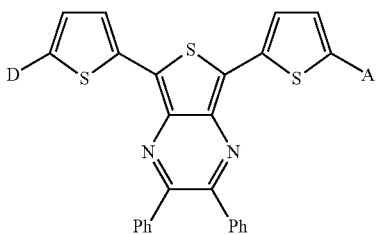

-continued

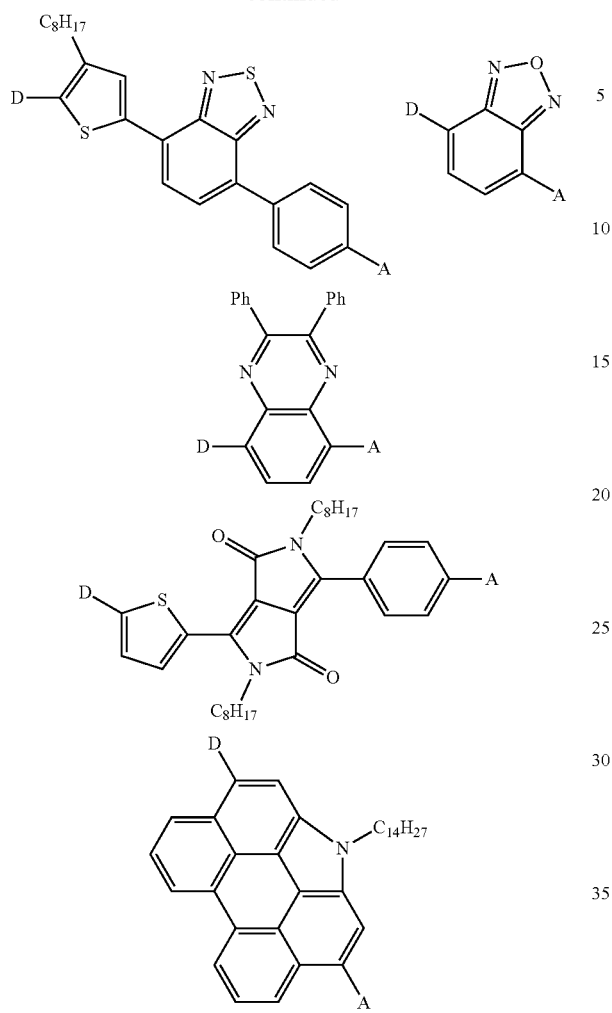

D = donor
A = acceptor

With respect to the dyes of the present invention, the π-bridge and the acceptor are not known to be critical. That is, even though many examples are given in the specification, any π-bridge and acceptor known in the dye-sensitizing solar cell art can be used in connection with the present invention.

Examples of dyes of the present invention specifically include the following:

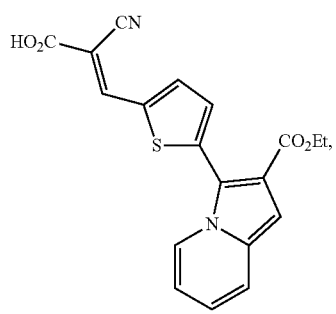

-continued

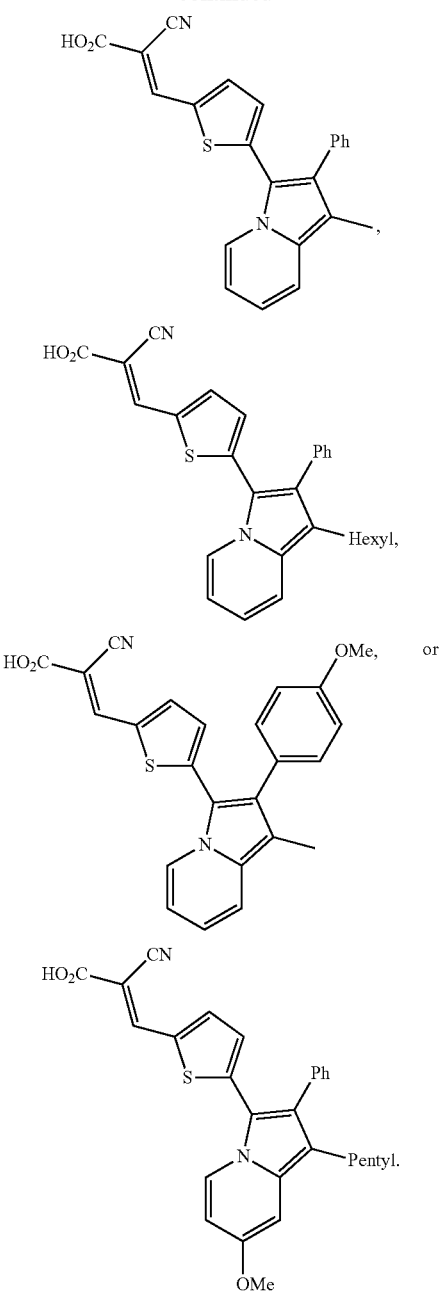

Further examples of dyes of the present invention include the following:

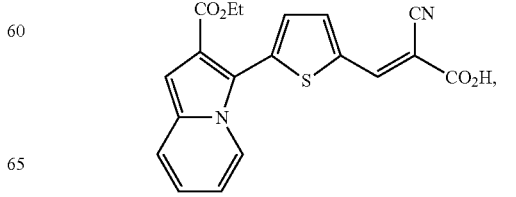

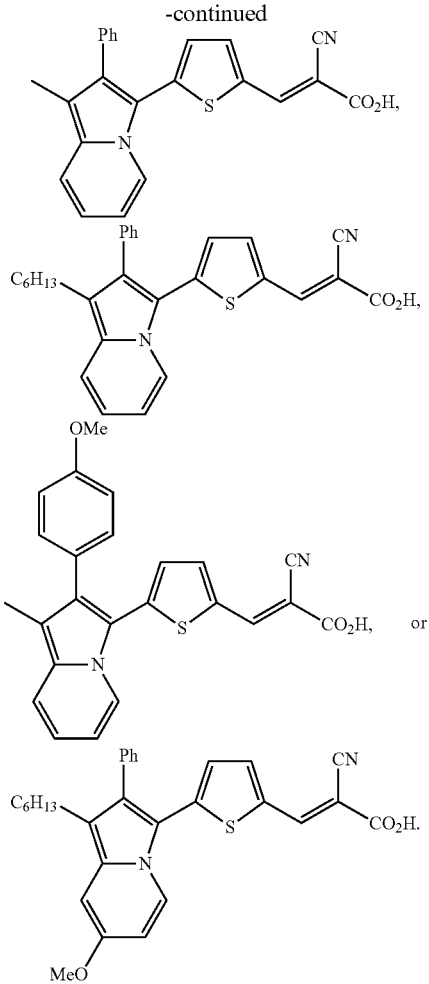
Even further examples of the dyes of the present invention include the following:
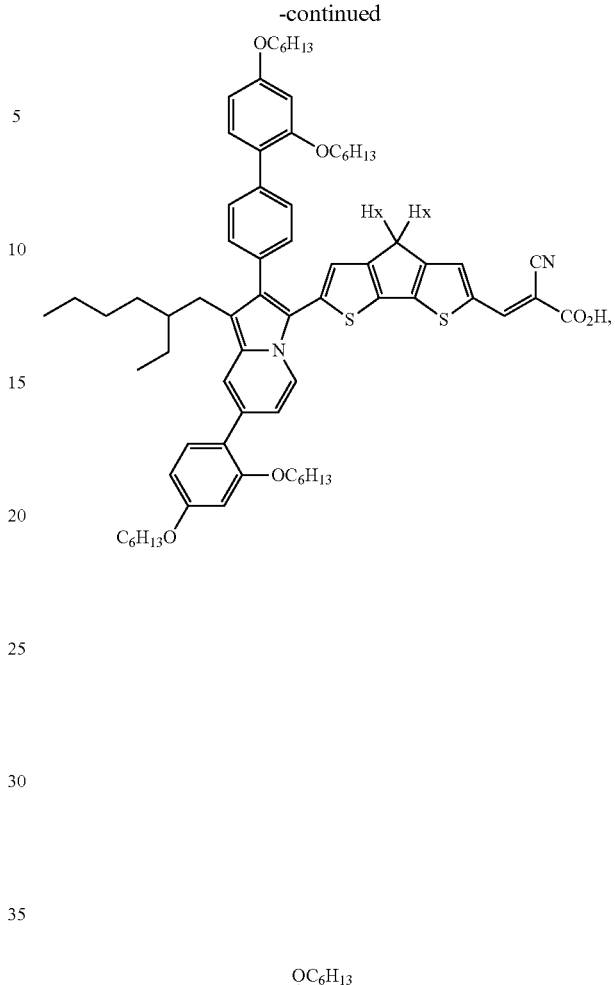
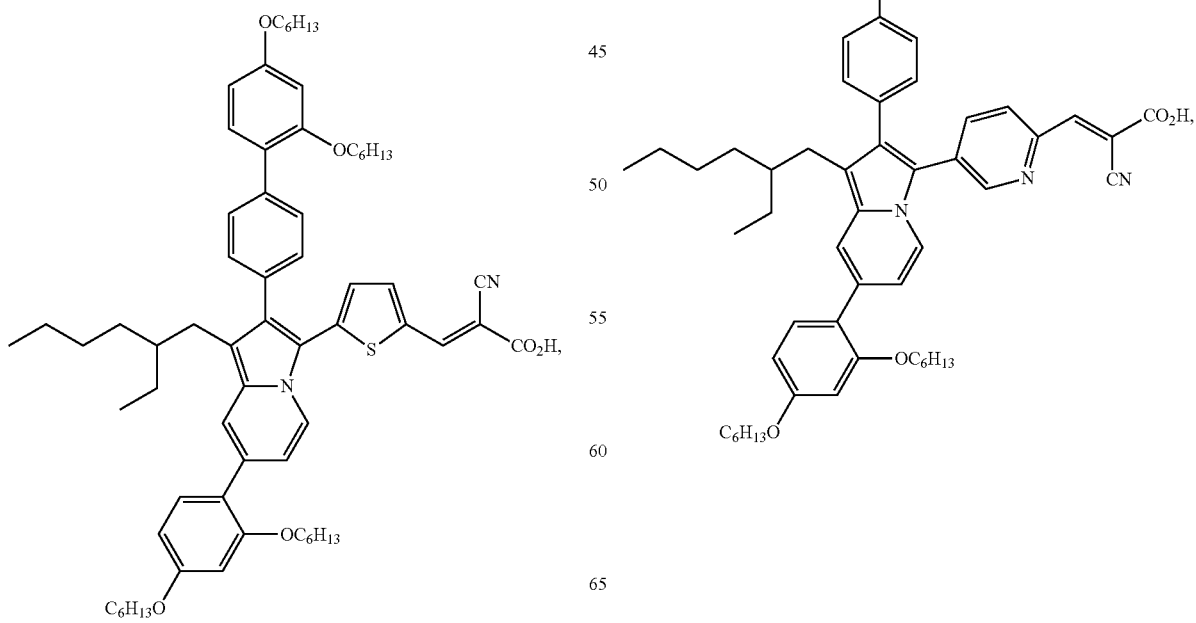

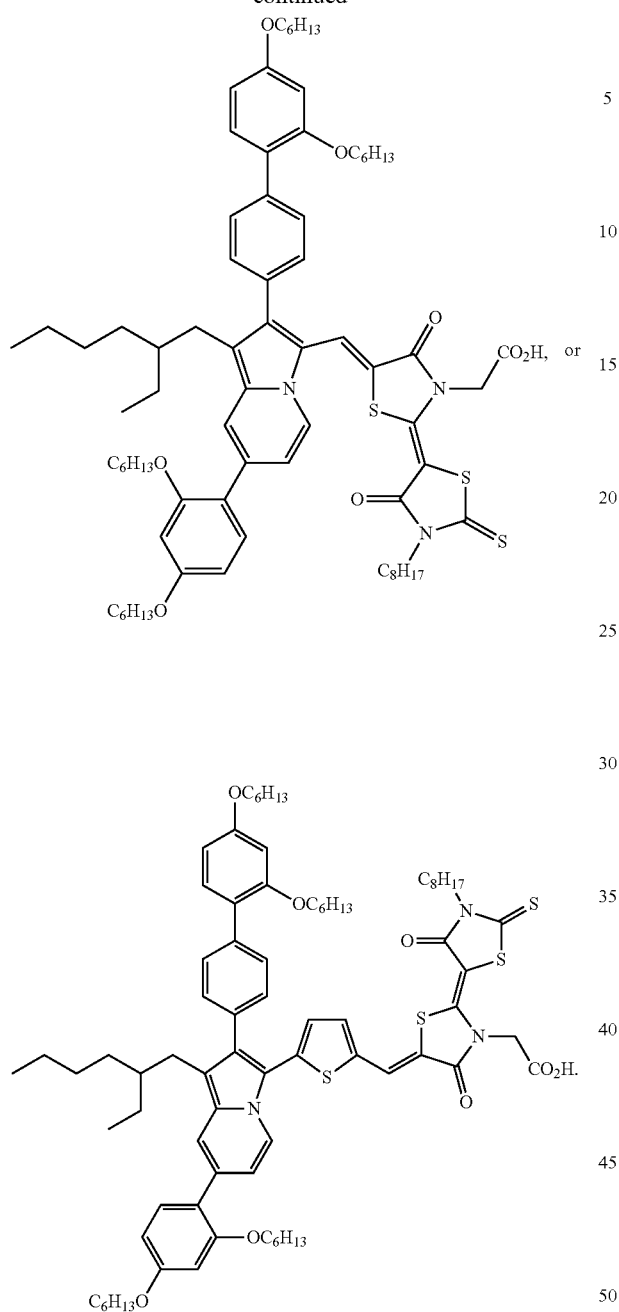
Further examples include the following:
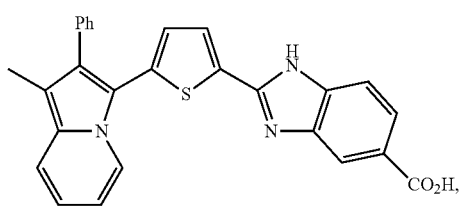
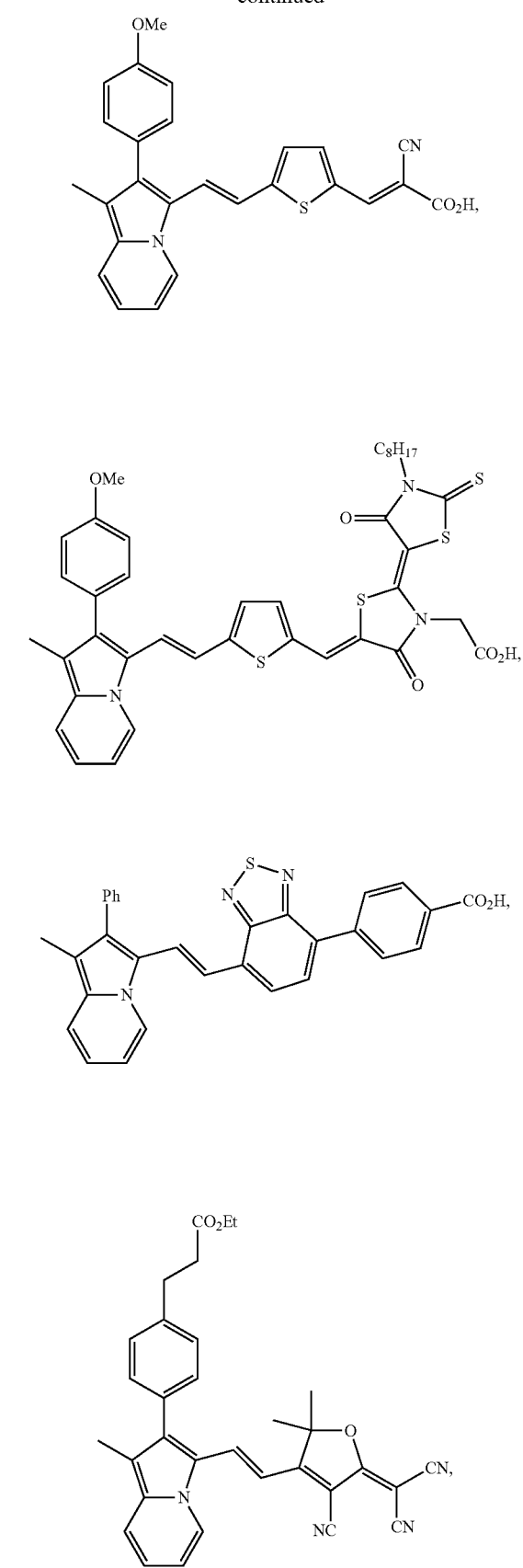
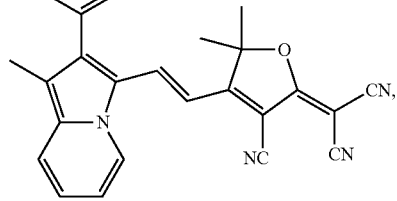

-continued

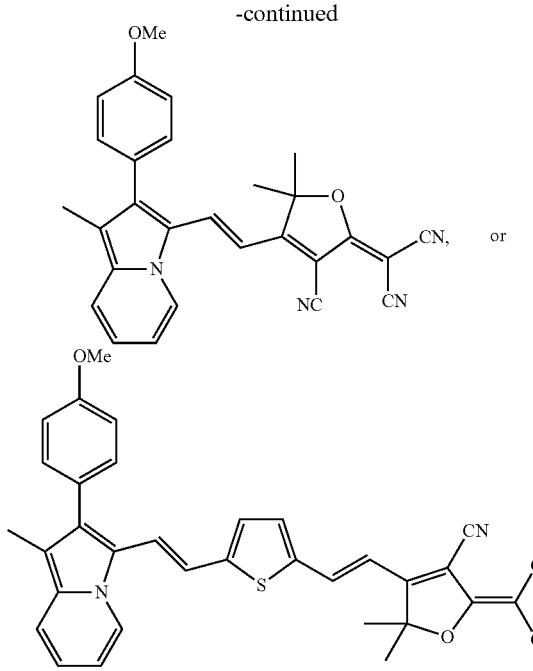

Further embodiments of the present invention include dye-sensitized solar cells that incorporate dyes of the present invention. For example, embodiments of the present invention include dye-sensitized solar cells that comprise an anode plate and a cathode plate, a dye of the present invention, a semiconducting oxide, and a redox couple or charge transport material.

Examples of the semiconducting oxide include $TiO_2$, ZnO, or $SnO_2$-based semiconducting oxides. However, the semiconducting oxide is not known to critical, so any semiconducting oxide known in the dye-sensitizing solar cell art can be used in connection with the present invention.

A preferred embodiment of the present invention is a dye-sensitizing solar cell that includes the following dye as an organic sensitizer component:

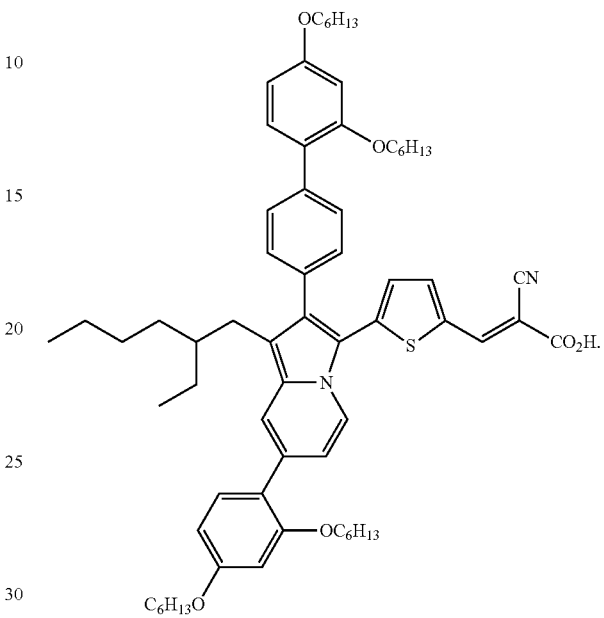

In other embodiments, the dye may be the following:

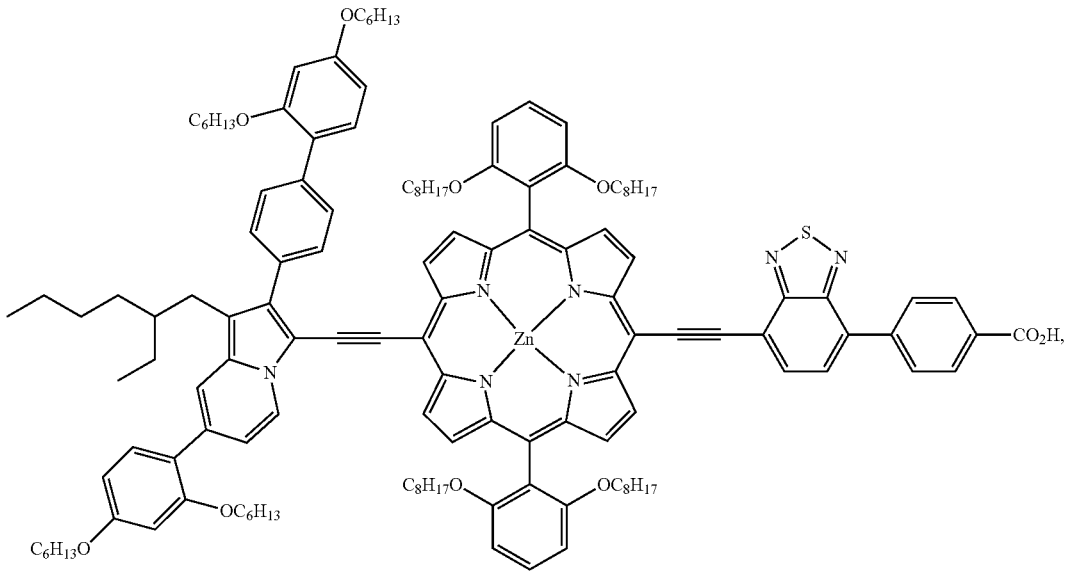

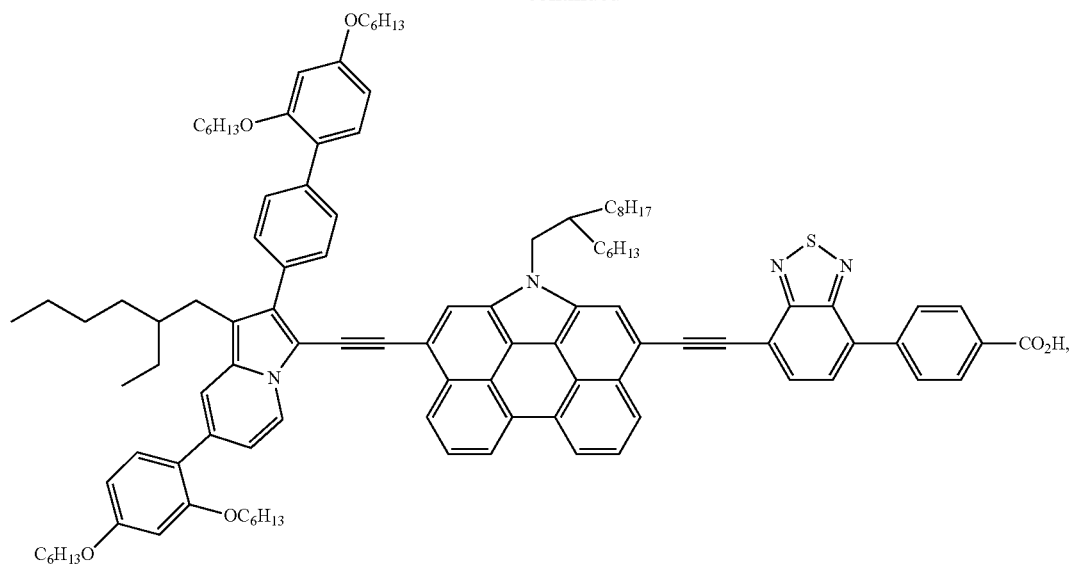
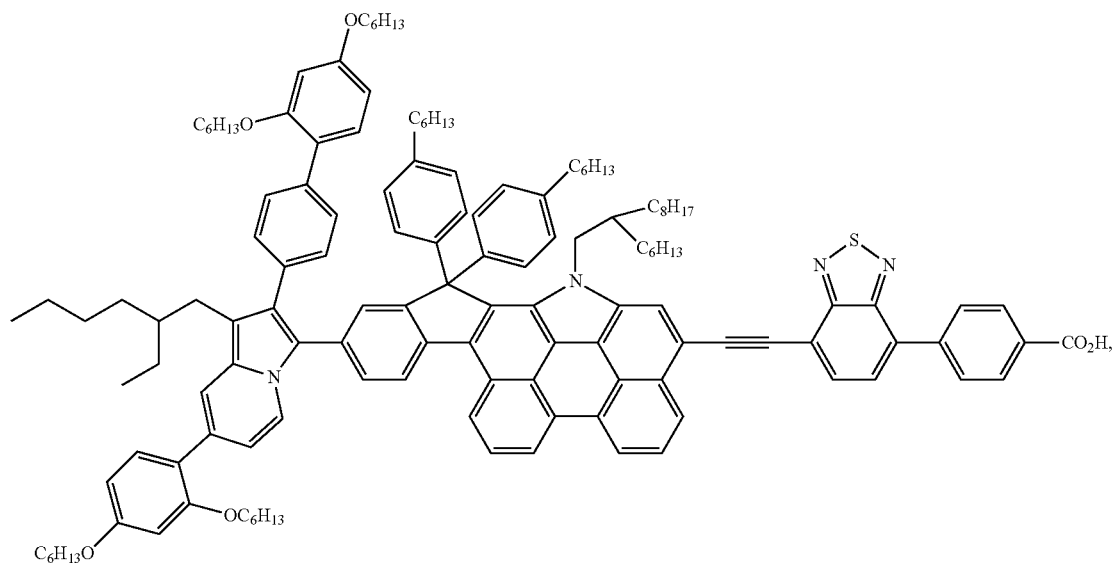
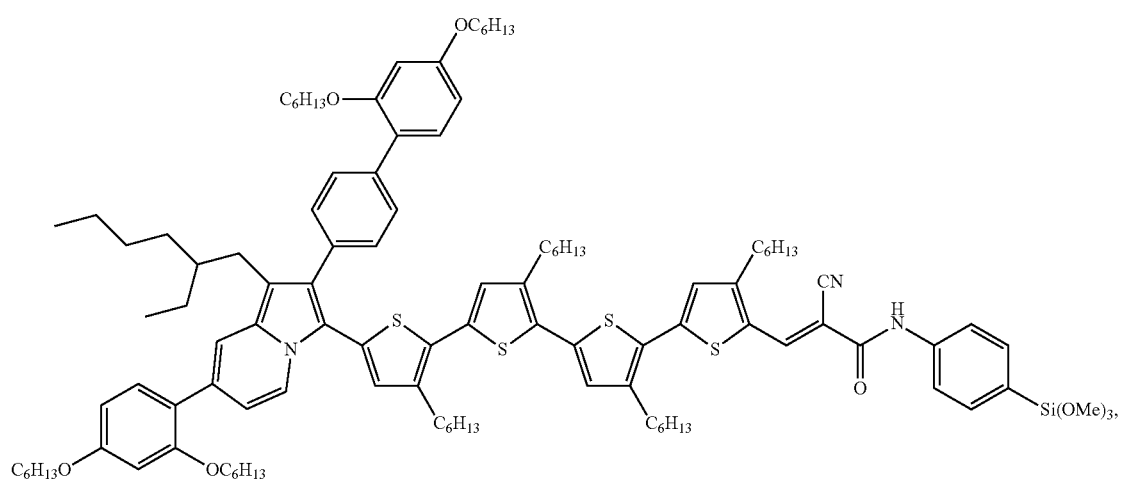

-continued
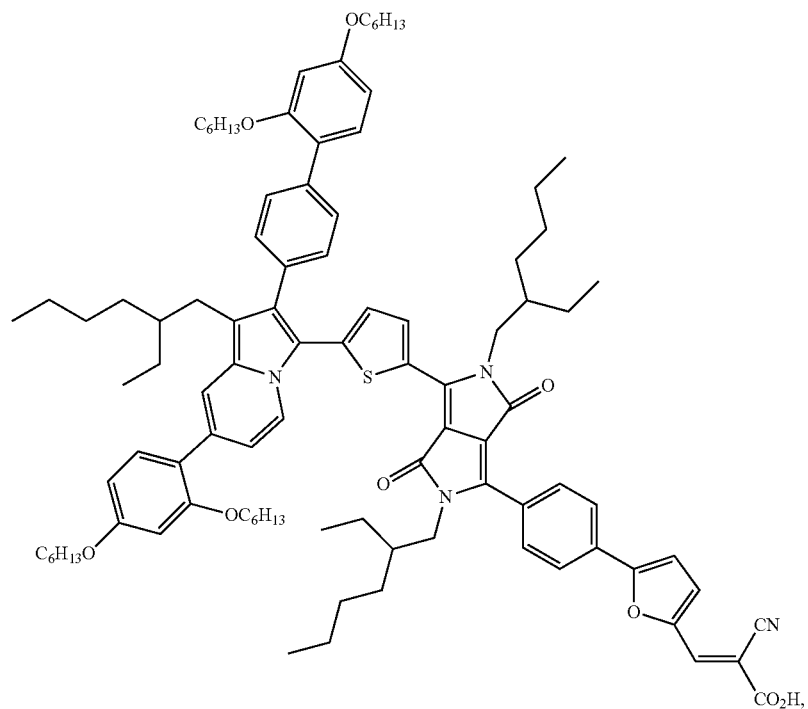
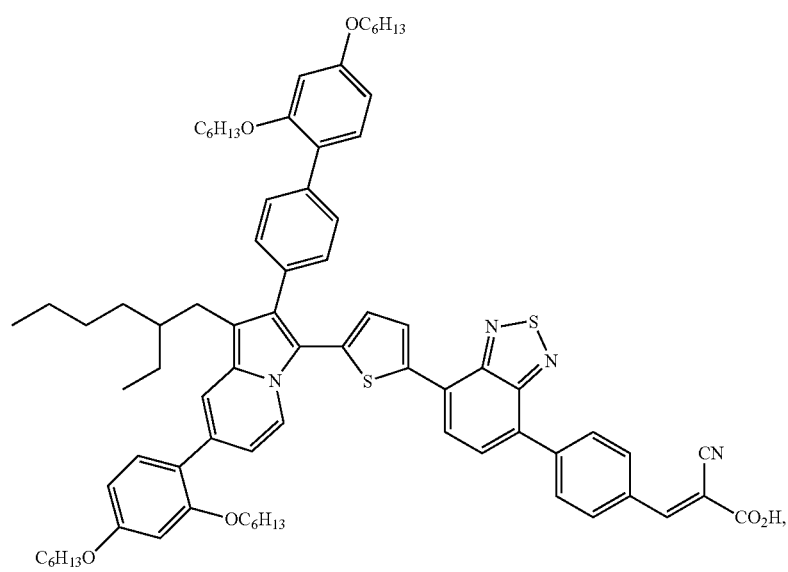

-continued
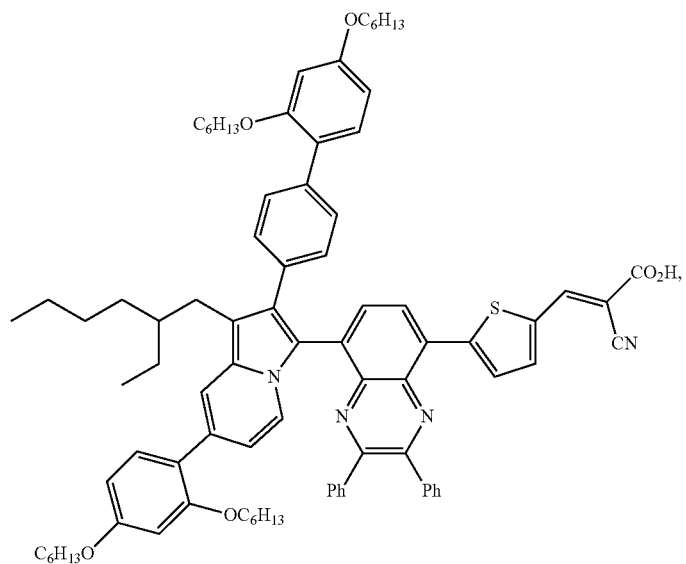
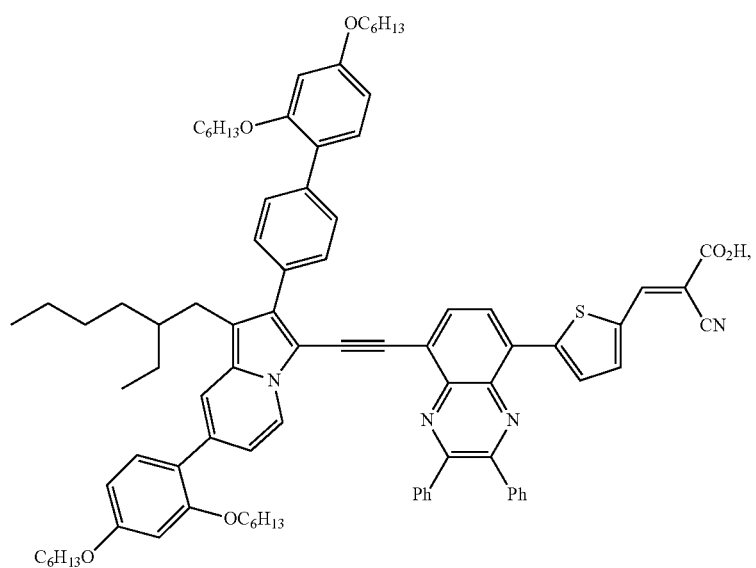
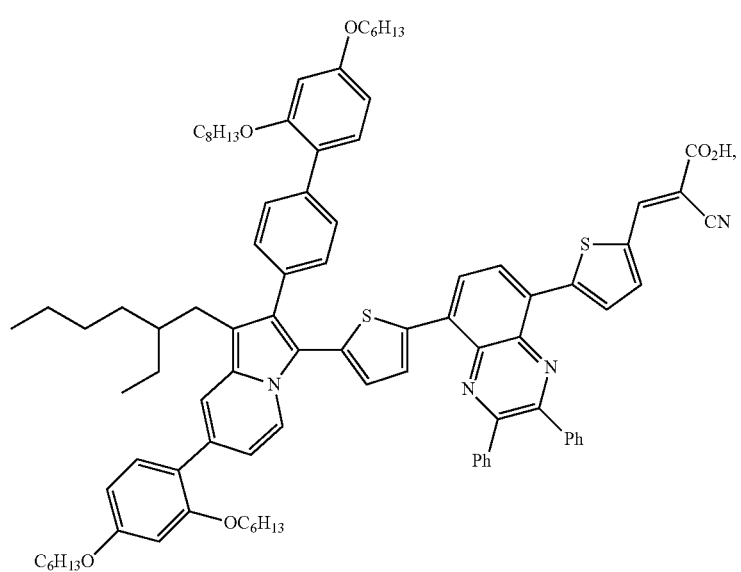

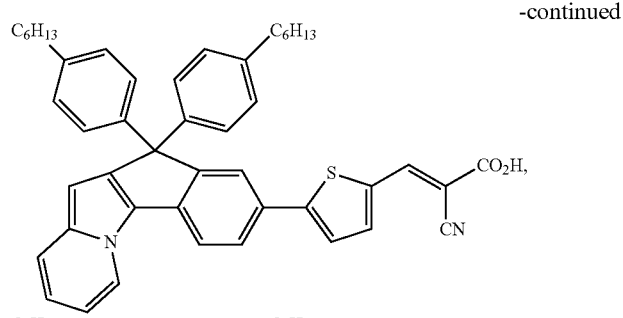
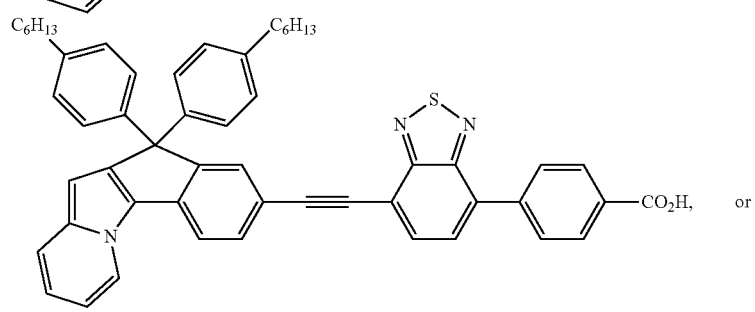
or
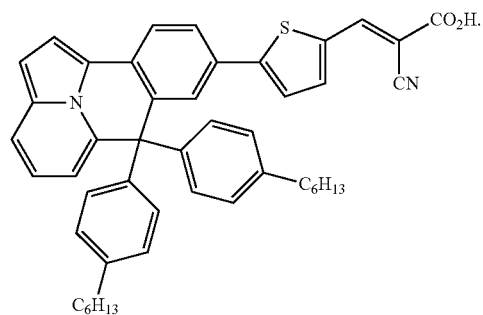
Non-limiting examples indolizine donors of the present invention:
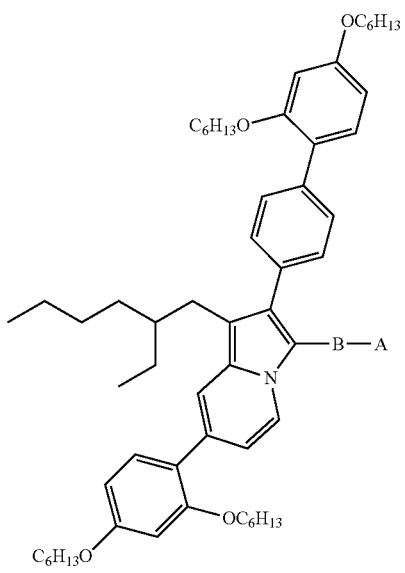
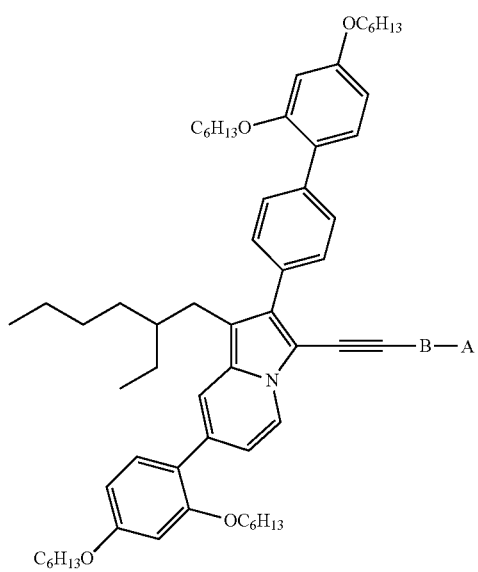

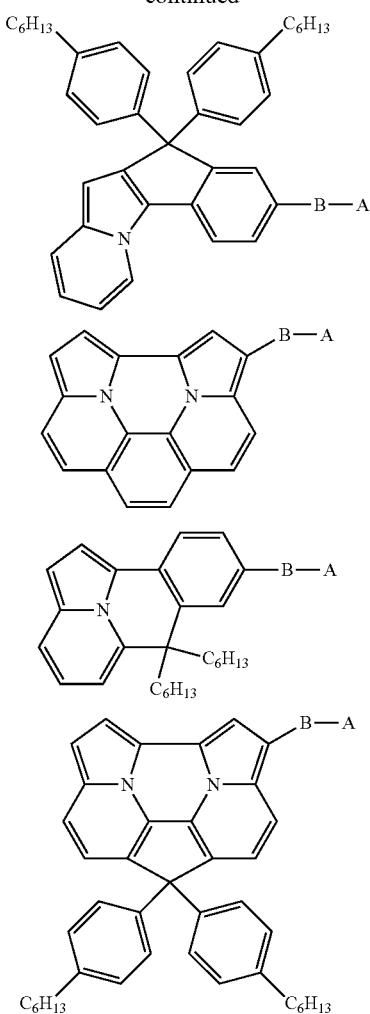
B = π-bridge
A = acceptor
In some embodiments of the presently-disclosed subject matter, a compound can be of the following formula:
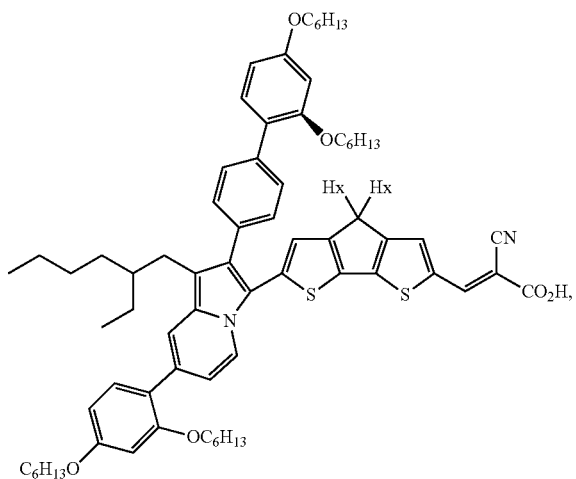
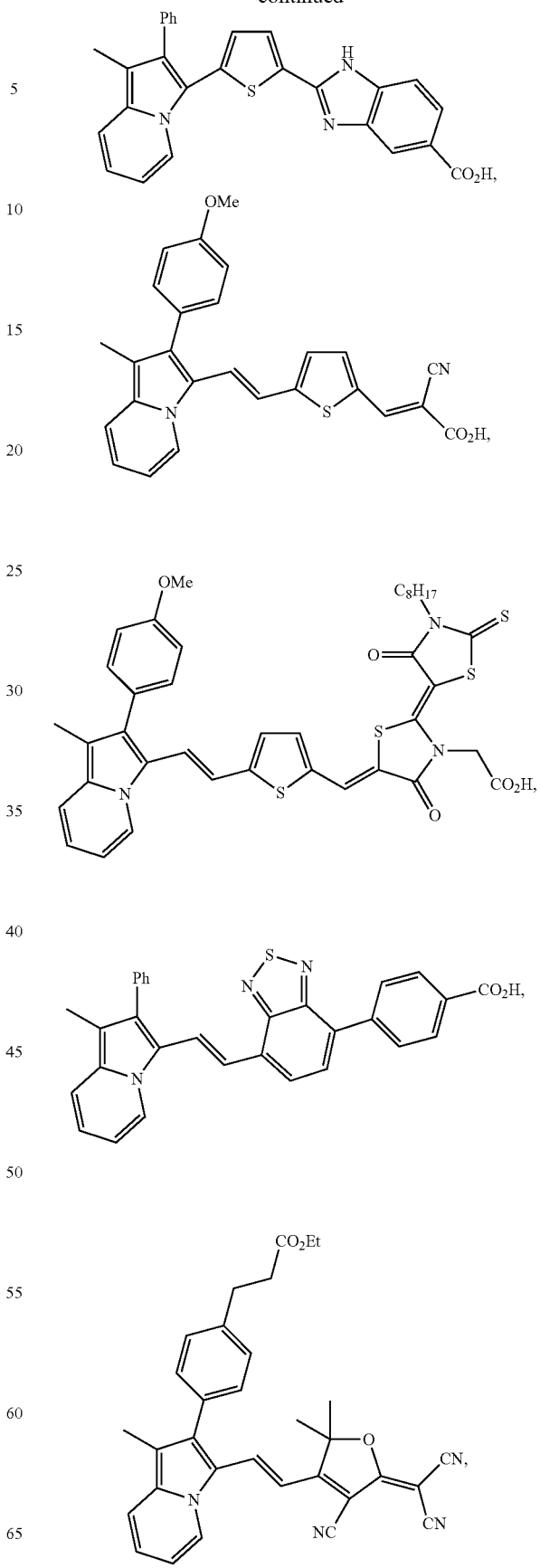

-continued
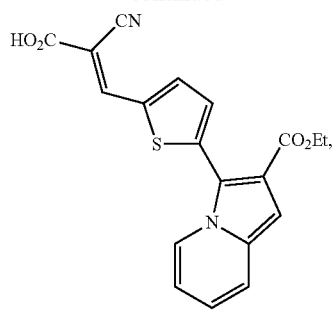
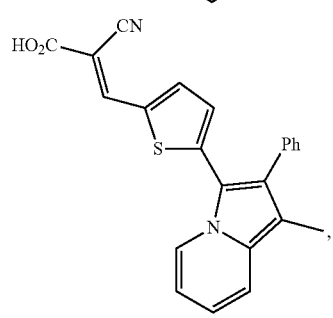
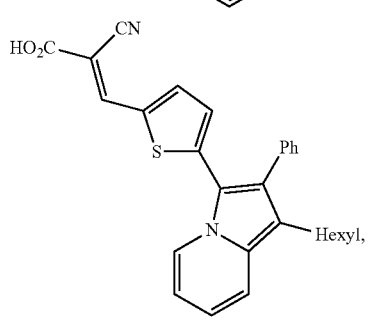
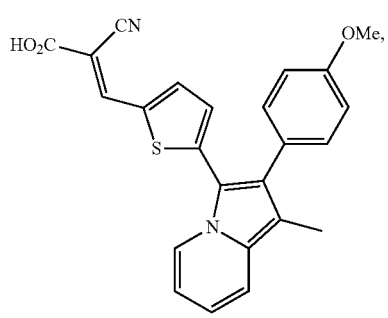
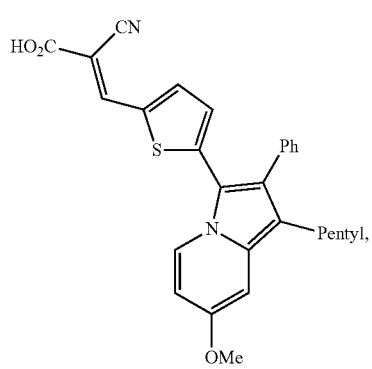
-continued
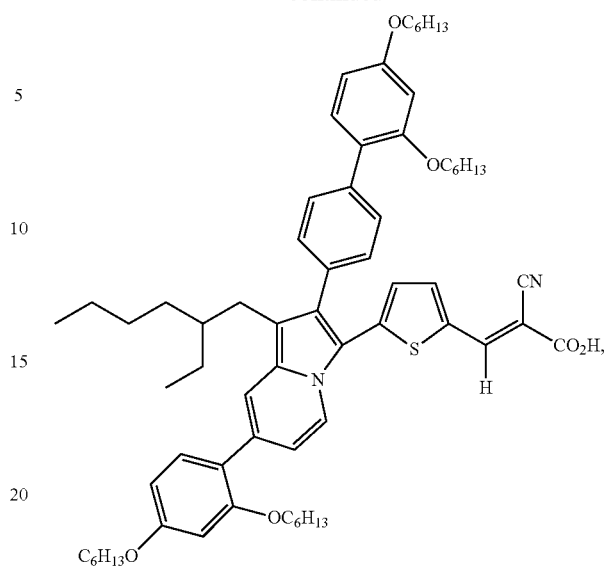
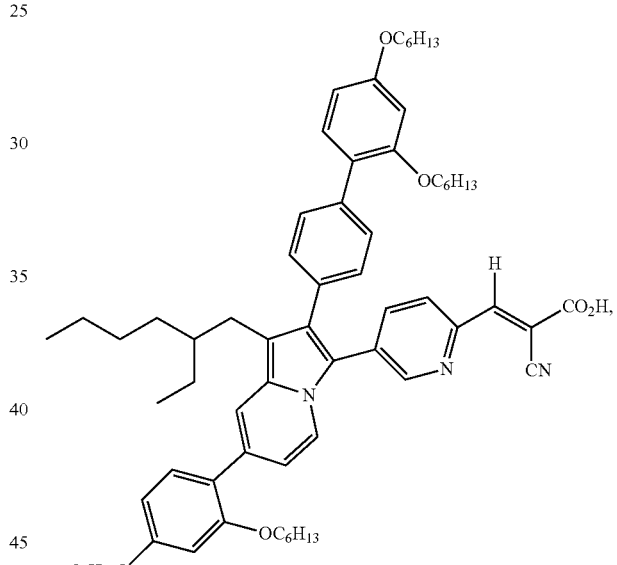
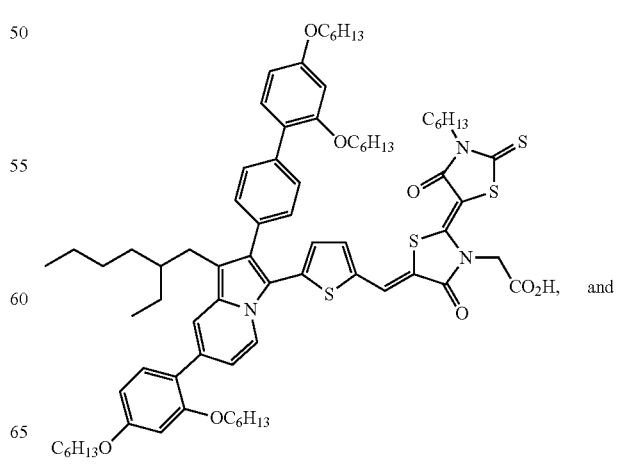
and -continued

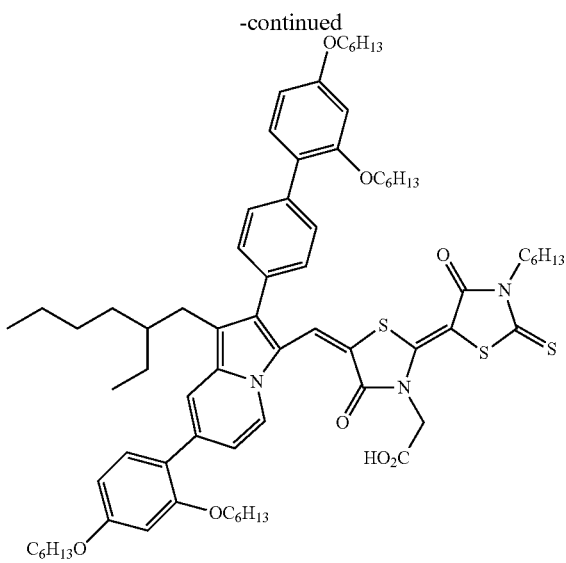

EXAMPLES

The presently-disclosed subject matter is further illustrated by the following specific but non-limiting examples. The following examples may include compilations of data that are representative of data gathered at various times during the course of development and experimentation related to the present invention.

Example 1

This Example describes the synthesis and characterization of embodiments of sensitizers in accordance with embodiments of the presently-disclosed subject matter. See FIG. 1. The selected DSC target indolizine-based dyes keep the π-bridge and acceptor regions constant as thiophene-cyanoacrylic acid (T-CAA) throughout the series for simple donor effect comparison (FIG. 1). The indolizine donors differ in electron-donating group (EDG) strength at the 2-position, substituent choice on the 6-member ring at the 5-position, and in varying alkyl chain length at the 3-position. For practical synthetic purposes, we found the 2-position may be substituted with either electron-withdrawing functionality (which adversely effects charge transfer based absorptions) or with aryl substituents to yield air-stable electron-rich intermediates.

The synthetic route employed for all dyes began with donor formation followed by palladium-catalyzed direct C—H arylation at the indolizine 2-position, then Knovenagle condensation. Concerning donor formation, indolizine 3 was prepared according to literature precedent. Synthesis of indolizine-based dyes AH3, AH4, AH5 and AH6 began with 2-alkylated pyridines which were either purchased (2-ethylpyridine), prepared through lithiation-alkylation (4), or prepared through Kumada coupling (6). The 2-alkyl pyridines were then N-alkylated with α-bromoacetophenones and underwent subsequent base-induced cyclization to form intermediates 7-10. The alkylation/cyclization sequence may be conducted in a single step to generate the parent polycyclic donor or as a two-step sequence with simple filtrations to purify the intermediate pyridinium salts (Scheme 1). It is noteworthy that indolizine 10 decomposes significantly within minutes when exposed to air which suggests the indolizine parent system for AH6 is near the maximum electron donating potential available for handling under ambient conditions. Palladium catalyzed C—H activation of the indolizine donors (3, 7-10) with 5-bromo-2-formylthiophene led to aldehyde intermediates 11-15, which underwent Knovenagle condensation with cyanoacetic acid to give the desired dyes AH2-AH6. These dyes are accessible in remarkably few synthetic steps (3-5 steps total) in up to 39% overall yield.

Scheme 1, above shows examples of synthetic routes to dyes AH2-AH6.

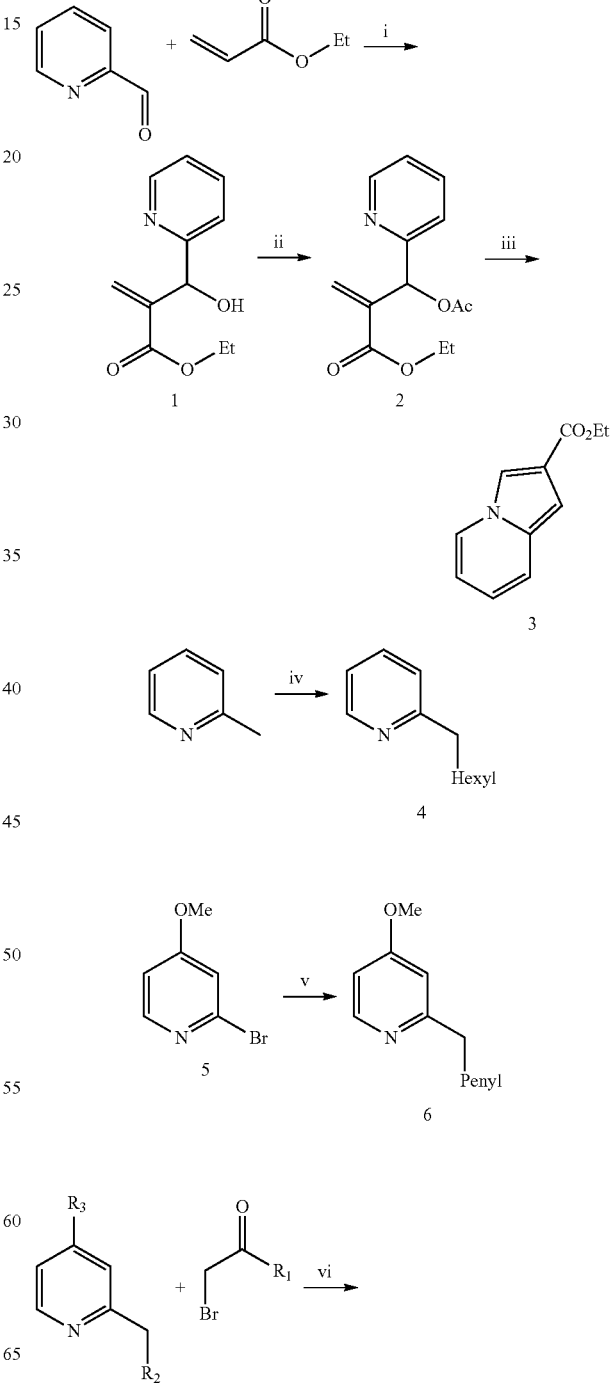

-continued

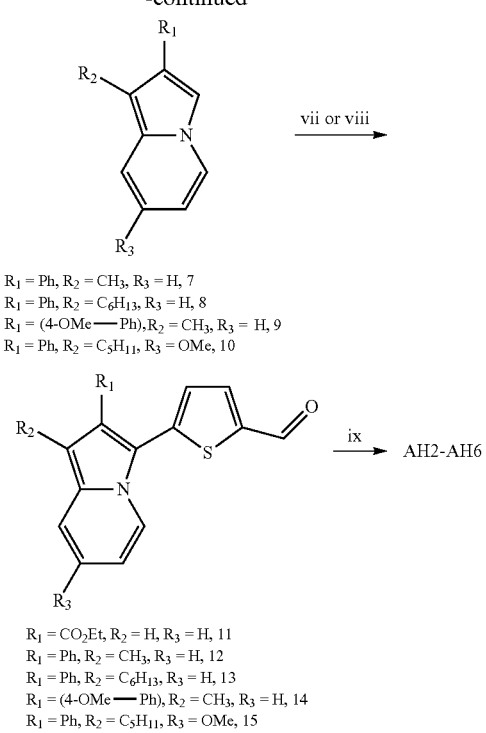

R₁ = Ph, R₂ = CH₃, R₃ = H, 7
R₁ = Ph, R₂ = C₆H₁₃, R₃ = H, 8
R₁ = (4-OMe—Ph), R₂ = CH₃, R₃ = H, 9
R₁ = Ph, R₂ = C₅H₁₁, R₃ = OMe, 10

R₁ = CO₂Et, R₂ = H, R₃ = H, 11
R₁ = Ph, R₂ = CH₃, R₃ = H, 12
R₁ = Ph, R₂ = C₆H₁₃, R₃ = H, 13
R₁ = (4-OMe—Ph), R₂ = CH₃, R₃ = H, 14
R₁ = Ph, R₂ = C₅H₁₁, R₃ = OMe, 15

In this example, reaction Conditions: i) DABCO, CHCl₃, rt, 91% 1; ii) Ac₂O, 100° C., 86% 2; iii) 120° C., neat, 76% 3; iv) t-BuLi, THF, −78° C., then C₆H₁₃Br, 50% 4; v) Mg, I₂, THF, rt to reflux, then Ni(dppp)Cl₂, pentylbromide, 0° C. to reflux, 92% 6; vi) acetone, reflux, then NaHCO₃, H₂O, reflux, 92%-16% intermediates 7-10; vii) R₃ = H, 5-bromothiophene-2-carboxaldehyde, Pd(PPh₃)₂Cl₂, KOAc, NMP, 80° C., 92-44% intermediates 11-14; viii) R₃ = OMe, Pd(OAc)₂, PCy₃, Cs₂CO₃, toluene, 130° C., 19% intermediate 15: ix) piperidine, cyanoacetic acid, CHCl₃, 90° C., 84-14%, AH2-AH6.

Example 2

This example demonstrates optical and electrochemical properties for near infrared compounds of the present invention.

Figure 2:
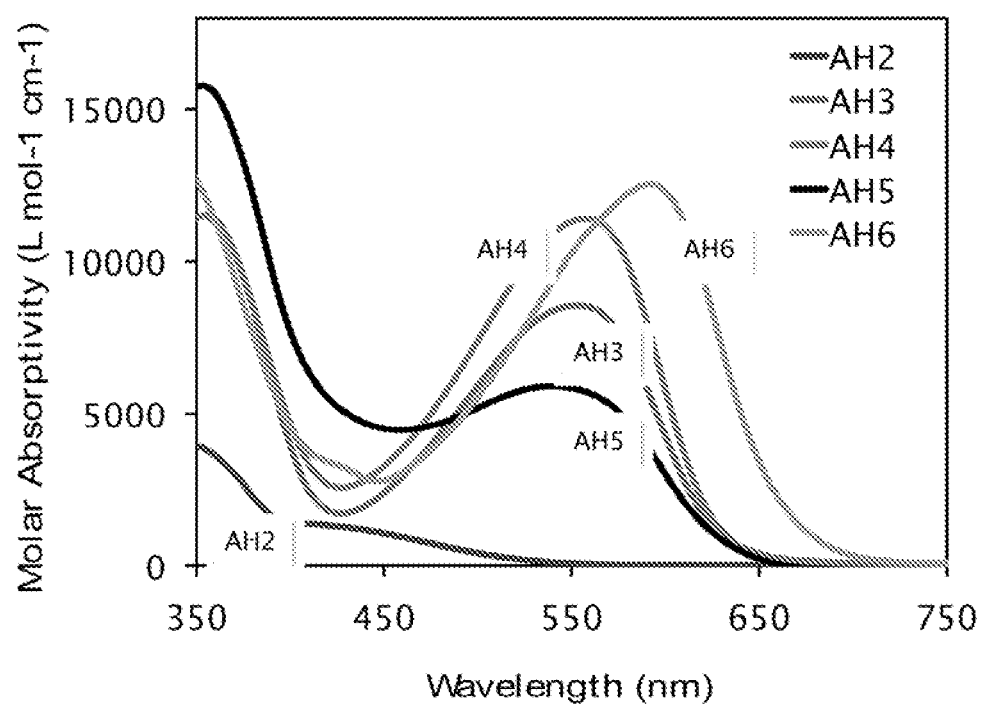
FIG. 2 shows absorption spectra of dyes AH2-AH6 measured in 0.05% AcOH and $CHCl_3$.

The optical properties of AH2-AH6 were analyzed to understand the effect of the indolizine substituents on the UV-Vis absorption properties (see Table 1, below, and FIG. 2).

TABLE 1

Optical and electrochemical properties of AH2-AH6 in dichloromethane solutions.

| dye | $\lambda_{max}$ [nm] [a] | $\lambda_{onset}$ [nm] [a] | $\varepsilon$ [$M^{-1}cm^{-1}$] [a] | $E_g^{opt}$ [eV] [b] | $E_{(S+/S)}$ [V] [c] | $E_{(S+/S^*)}$ [V] [d] |
|---|---|---|---|---|---|---|
| AH2 | 419 (sh) | 535 | 1,250 | 2.32 | 1.22 | −1.10 |
| AH3 | 553 | 633 | 8,500 | 1.96 | 0.99 | −0.97 |
| AH4 | 558 | 633 | 11,300 | 1.96 | 0.99 | −0.97 |
| AH5 | 562 (sh) | 640 | 5,800 | 1.94 | 0.97 | −0.97 |
| AH6 | 592 | 675 | 12,500 | 1.84 | 0.85 | −0.99 |
| CQ1[e] | 442 | 540 | 25,000 | 2.30 | 1.16 | −1.14 |
| C1[f] | 499 | 590 | 27,500 | 2.10 | 1.04[g] | −1.06 |
| LS1[h] | 523 | 600 | 20,000 | 2.07 | 1.01 | −1.06 |

[a] Measured in CH₂Cl₂ and 0.5% AcOH.
[b] Estimated from the intercept of an absorption curve tangent line intercept with the baseline on the low energy side of the maximum absorption curve in CH₂Cl₂. Conversion from nanometers to eV was calculted by $E_g^{opt} = 1240/\lambda_{onset}$. $E_{(0-0)}$ for dyes (for which emissions were observed) were measured at the intercept of the absorption and emission curves is CH₂Cl₂ and is available in the experimental section.
[c] Measured in a 0.1M Bu₄NPF₆ in CH₂Cl₂ solution with glassy carbon working electrode, Pt reference electrode, and Pt counter electrode with ferrocene as an internal standard. Values are reported versus NHE.
[d] Calculated from $E_{(S+/S^*)} = E_{(S+/S)} − E_g^{opt}$.
[e] Triphenylamine-thiophene-cyanoacrylic acid dye, CQ1. See ref. 11.
[f] p-Dimethoxytriphenylamine-thiophene-CAA dye, C1. See ref. 12.
[g] Estimated from the CV curve in CH₂Cl₂.
[h] Indoline-thiophene-CAA dye, LS1.

Substituents at the 2-position of indolizine were found to be electronically active whereas the dyes AH2. AH3 and AH5 exhibited red-shifted $\lambda_{max}$ values progressing from electron withdrawing groups (EWGs) to EDGs (ester<pH-phenyl<pMeO-phenyl) over a range of ~150 nanometers (nm) (FIG. 2). Additionally, substituents on the 5-position of indolizine were found to give a significant red-shift (~50 nm) when comparing H-substituted AH4 to OMe-substituted AH6. The large red-shifted absorptions (75-135 nm $\Delta\lambda_{onset}$ AH6 vs. CQ1,[12] C1[13] & LS1[14]) observed with the indolizine dye series when compared to other common donor-based dyes illustrates the strong electron donation strength of the indolizine building blocks. The molar absorptivities ranged from 1,000-13,000 $M^{-1}cm^{-1}$ with the short alkyl chain length dyes at the 3-position (AH2, AH3 and AH5) yielding the lowest molar absorptivities. AH2 has a lower molar absorptivity than the remaining indolizine-based dyes, which may be the result of a weakened charge transfer transition due to the addition of an electron deficient ester on the indolizine donor. The indolizine donors are more sterically congested at the donor-π bridge bond than phenyl amine based donors and computational analysis indicates larger twist angles (32' vs. ~20°) about this bond, which correlate to diminished molar absorptivities.

Figure 3:
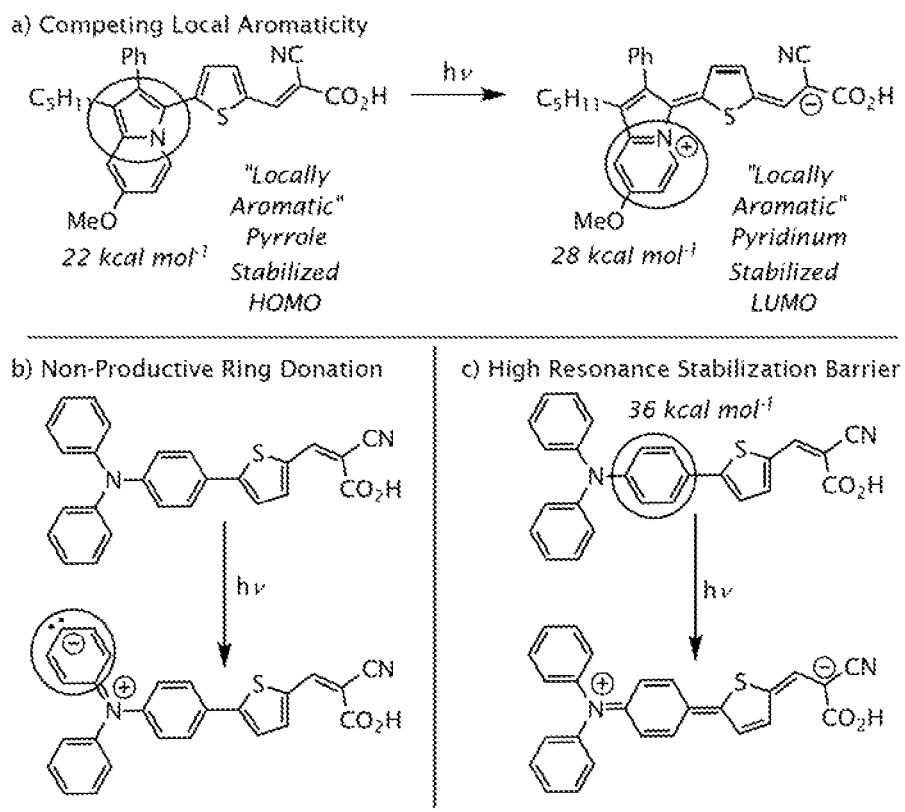
FIG. 3 shows a) structures a dye of the present invention in the ground- and excited-state, illustrating the competing local aromaticity between the pyrrole and pyridinium substructures; b) structure of CQ1 with a non-productive conjugated pathway illustrated; and c) structure of CQ1 in the ground- and excited-state illustrating a high-resonance stabilization barrier, which must be overcome for charge transfer to occur.

The increase in wavelength absorption breadth of indolizine donors when compared with triaryl- and diarylamine donors can be rationalized through several factors including amine planarity (FIG. 1), the generation of an aromatically stabilized pyridinium excited-state region upon electron donation (FIG. 3a), less competing electron donation directionality due to indolizine being a fully conjugated donor system (FIG. 3b), and a lower inherent resonance stabilization energy for the amine donor to overcome than the common benzene resonance stabilization energy (FIG. 3c). The excited-state generated pyridinium substructure has a larger aromatic stabilization energy than the ground-state locally aromatic pyrrole (28 kcal mol⁻¹ vs. 22 kcal mol⁻¹) which likely leads to a substantially lower charge-transfer energy barrier. Proaromatic substructures (i.e. substructures with competing local aromaticity) are rare in donor functionality and are most commonly observed with π-bridges and acceptors.

The electrochemical properties of the D-π-A dyes AH3-AH6 were analyzed with regard to DSC device components to evaluate if the dyes are energetically suitable for regeneration from the I⁻/I₃⁻ redox shuttle and electron injection into a mesoporous TiO₂ semiconductor (Table 1). Through cyclic voltammetry (CV), the ground-state oxidation potentials ($E_{(S+/S)}$) of AH3-AH6 are established to range from 0.99 to 0.85 V versus normal hydrogen electrode (NHE) which indicates regeneration from the I$^-$/I$^-_3$' redox shuttle is favorable ($\Delta G_{reg}$=500-640 mV). According to the equation $E_{(S+/S^*)} = E_{(S+/S)} - E_{(0-0)}$ the excited-state oxidation potentials ($E_{(S+/S^*)}$) are determined based on $E_{(S+/S)}$ and the intercept of the absorption and emission curves ($E_{(0-0)}$) (see supporting information for emission plots). The $E_{(S+/S^*)}$ values were found to be favorable for electron injection into the TiO$_2$ conduction band ($\Delta G_{inj}$=470-490 mV). The oxidation potential of indolizine dyes AH3-AH6 were found to be significantly higher in energy when compared with triphenyl amine and indoline based dye derivatives. The fully conjugated indolizine donors enhance electron donation strengths leading to a significant destabilizing of the oxidation potential relative to typical donors, and the proaromatic pyridinium substructure leads to a unique donor-induced stabilization of the excited-state oxidation potential. Because the optical band-gap is concomitantly narrowed, longer absorption wavelengths may be accessed with an atypically low number of conjugated π-bonds relative to typical DSC D-π-A dyes with absorptions reaching ~700 nm.

While $E_{(S+/S)}$, is a good measure of a one-electron donation strength and the ability of the molecule to stabilize a radical cation, we sought to also examine the two-electron donation strengths through a comparison of the CAA carbonyl vibrational stretches between dyes. The CAA carbonyl stretch shifts to smaller wavenumbers with increasing donor strength and allows for a comparison of a variety of donor groups with identical 2-bridges and acceptors. The TPA-based dyes L1 (identical to CQ1) and C213 (a C1 analogue) give similar values for this stretch (1683 cm$^{-1}$ for L1,[15] 1682 cm$^{-1}$ for C213, Table 2).[16] An indoline-based dye gave only a slightly smaller carbonyl vibrational frequency value (1680 cm$^{-1}$).[17] In comparison, indolizine-based dyes gave an average value of 1646 cm$^{-1}$, which is a significantly lower wavenumber (~35 cm$^{-1}$) than the other donors examined. Additionally, the C—N bond stretch of the CAA cyano group was compared between the four donors (Table 2). Both TPA donors (L1 and C213) have the same value (2216 cm$^{-1}$), while indoline is estimated to be near identical (~2220 cm$^{-1}$). The indolizine dyes again demonstrated the lowest C—N bond stretch value (2203 cm$^{-1}$) further illustrating an enhanced two-electron donation strength.

TABLE 2

Electrochemical and spectroscopic vibrational analysis of dyes with varying donor functionalities (with T-CAA as bridge and acceptor) as they pertain to electron donation strength.

| Dye | asymmetric CO [cm$^{-1}$] | CN [cm$^{-1}$] | $E_{(S+/S)}$ [V] |
|---|---|---|---|
| L1 (CQ1) | 1683 | 2216 | 1.16 |
| C213 (C1) | 1682 | 2216 | 1.04 |
| LS1 | 1680 | 2220[a] | 1.01 |
| AH3 | 1646 | 2203 | 0.99 |

[a]Estimated from IR absorption figure in Ref. 18.

Example 3

Figure 4:
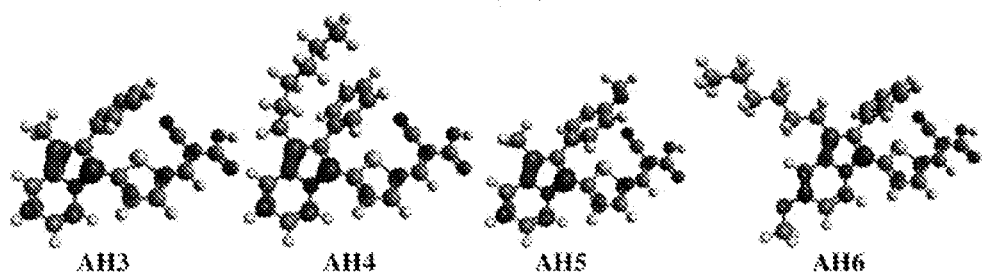
FIG. 4. HOMO (top) and LUMO (bottom) orbitals for dyes of the present invention with a set contour value of 0.065.
Figure 4:
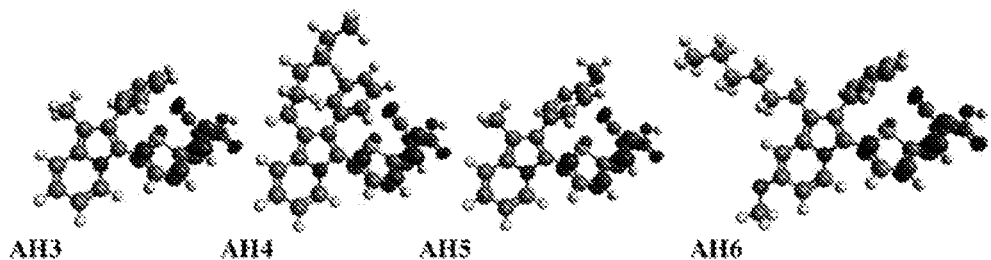

For dyes to efficiently inject electrons into the TiO$_2$ conduction band with minimal back electron transfer from TiO$_2$ to the oxidized dye, the LUMO should be positioned near the dye anchor and significantly separated from the dye HOMO. To examine the orbital geometries, AH3-AH6 were computationally evaluated using a variety of density functional theory (DFT) methods (B3LYP, VSXC, MN12L, N12, M11L, VSXC, M06L, LC-PBE, PBE0, CAM-B3LYP) and basis sets (6-31G(d,p), 6-311G(2df,2pd)) in vacuum and in dichloromethane polar continuum model (PCM). The HOMO and LUMO orbitals for each of the dyes show the HOMO primarily localized on the indolizine donor and the LUMO primarily localized on the T-CAA motif (FIG. 4). The dye LUMO and HOMO orbital arrangements are well situated for efficient electron injection from the dye into the TiO$_2$ conduction band and diminished back electron transfer from the TiO$_2$ semiconductor to the oxidized dye, respectively.

A tremendous number of organic dye building blocks are available to tune dye properties. An experimentally accurate computational method for predicting dye absorption spectrum can have a dramatic impact on prioritizing future synthetic dye targets and on the wise utilization of chemical resources. To establish an accurate computational method, time-dependent DFT (TD-DFT) computations were performed to analyze the dye vertical transitions and oscillator strengths (Table 3, FIG. 4, ESI). After extensive calibration (Table 3, ESI), DFT/TD-DFT protocols were identified for the computation of the vertical transitions of AH3-AH6 that could reliably reproduce the experimental $\lambda_{max}$ (within 10 nm). TD-DFT computations performed in vacuum with the VSXC functional and 6-31G(2df,2pd) basis set gave very good agreement when using geometries optimized with either the VSXC or B3LYP functionals (within 10 nm or 20 nm respectively). While these results were highly accurate, we sought to examine the effects of solvent on the structures and vertical transitions of AH3-AH6 through the use of an implicit solvation model for dichloromethane. We compared results with a PCM applied to only the TD-DFT analysis in addition to a PCM applied to both the geometry optimization and TD-DFT calculations (Table 3). When TD-DFT calculations were coupled with PCM only, the B3LYP functional provided better agreement with the experimental $\lambda_{max}$ values regardless of whether the VSXC or B3LYP functional was employed for the geometry optimizations in vacuum (within 20 nm of AH3-AH6). Application of a PCM to both TD-DFT and geometry optimizations gave similar results with agreement to within 25 nm of experimental results. These results are consistent with a recent review of TD-DFT benchmarks for vertical transitions.[18] This level of agreement is encouraging given the relative simplicity of these computational models, and it suggests the predictive computational analysis of extended conjugation π-bridges could play an important role in the design and development of second generation dye targets based on indolizine donors.

TABLE 3

Deviations ($\Delta\lambda$ in nm where + indicates an overestimation of the experimental $\lambda_{max}$) from experimental $\lambda_{max}$ values for the most intense vertical transition computed with two different functionals and the 6-311G(2df, 2pd) basis set.

| | | AH3 | AH4 | AH5 | AH6 |
|---|---|---|---|---|---|
| Experimental Reference ($\lambda_{max}$ in nm) | | 553 | 558 | 562 (sh) | 592 |
| TD-DFT | Geometry Optimization | $\Delta\lambda$ in nm | | | |
| Vacuum | Vacuum | | | | |
| B3LYP | B3LYP | −44 | −52 | −62 | −63 |
| B3LYP | VSXC | −40 | −38 | −44 | −47 |

TABLE 3-continued

Deviations (Δλ in nm where + indicates an overestimation of the experimental $\lambda_{max}$) from experimental $\lambda_{max}$ values for the most intense vertical transition computed with two different functionals and the 6-311G(2df, 2pd) basis set.

|  |  | AH3 | AH4 | AH5 | AH6 |
|---|---|---|---|---|---|
| VSXC | B3LYP | +17 | +5 | −18 | −12 |
| VSXC | VSXC | +4 | +9 | −4 | +1 |
| PCM[a)] | Vacuum |  |  |  |  |
| B3LYP | B3LYP | +2 | −6 | −19 | −11 |
| B3LYP | VSXC | +2 | +3 | −7 | 0 |
| VSXC | B3LYP | +68 | +53 | +29 | +40 |
| VSXC | VSXC | +49 | +52 | +46 | +48 |
| PCM[a)] | PCM[a)] |  |  |  |  |
| B3LYP | B3LYP | 0 | −8 | −10 | −18 |
| B3LYP | VSXC | +3 | +4 | −1 | −24 |
| VSXC | B3LYP | +57 | +43 | −10 | +21 |
| VSXC | VSXC | +44 | +49 | +49 | +7 |
| Experimental Reference ($\lambda_{max}$ in nm) |  | 553 | 558 | 562 (sh) | 592 |

[a)]Default solvent parameters for dichloromethane.

Example 4

Figure 5:
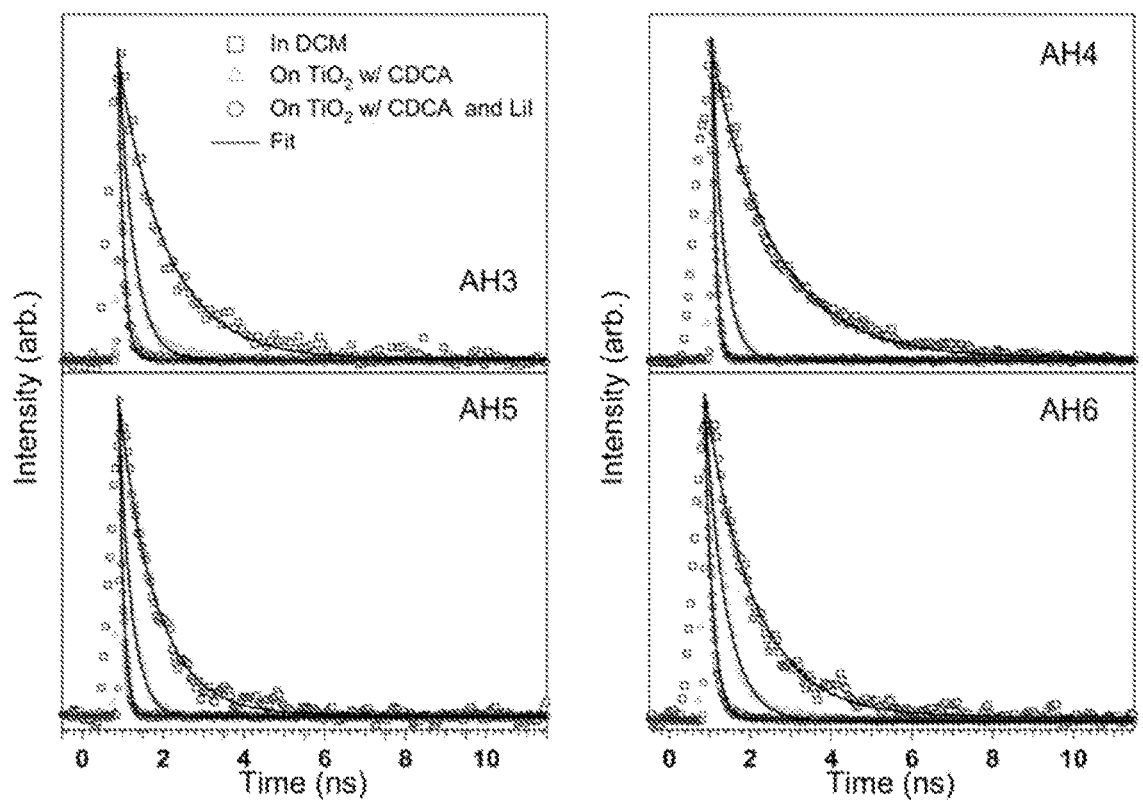
FIG. 5. Excited-state fluorescence decay curves for dichlormethane solutions and $TiO_2$ films sensitized with dyes of the present invention. Square markers are dichloromethane dye solutions, triangle markers are dyes on $TiO_2$ films with CDCA under air, circle markers are dyes on $TiO_2$ films with CDCA and mock-device electrolyte 0.002 M LiI in acetonitrile.

This Examples shows fluorescence lifetime measurements of embodiments of the present invention Electron injection from each of the dyes into the $TiO_2$ conduction band was found to be geometrically favorable through computational analysis of HOMO/LUMO orbital positions as well as thermodynamically favorable through electrochemical, UV-Vis and emission spectrum analysis. To examine the kinetics for electron injection, fluorescence lifetime studies were undertaken for each of the dyes in solution and on $TiO_2$ films to evaluate electron injection efficiencies ($\eta_{eff}$, where $\eta_{eff} = 1 - \tau_{TiO2}/\tau_{sol}$). Lifetimes of the dyes in dichloromethane solutions ($\tau_{sol}$) were found to be on the order of nanoseconds ranging from 1.6 ns to 0.9 ns (FIG. 5, Table 4). Excited-state lifetimes of the dyes on $TiO_2$ films ($\Sigma_{TiO2}$) are predicted to be significantly shorter whereas electrons may be injected from the dye into the $TiO_2$ CB effectively quenching the fluorescence. Dye-$TiO_2$ film fluorescence lifetimes were measured under three environmental conditions: (1) with dye and $TiO_2$ under air, (2) with dye, $TiO_2$ and known deaggreation agent chenodeoxycholic acid (CDCA) under air, and (3) with dye, $TiO_2$ and CDCA in a filled acetonitrile cell containing a typical device electrolyte lithium iodide concentration of 0.002 M. $\tau_{TiO2}$ was found to be dramatically shorter for all dyes on $TiO_2$ regardless of environment. Without any additives, $\eta_{eff}$ was found to vary between 45-82% according to the following order: AH4>AH3>AH5>AH6. Upon introduction of CDCA, a substantial increase in $\eta_{eff}$ a is observed for AH5 and AH6 leading to a range of injection efficiencies from 70-82%. The increase in efficiency is likely due to the reduction of intermolecular energy transfer between aggregated dyes on the $TiO_2$ film, which decreases the rate of electron injection into the $TiO_2$ conduction band. Upon the addition of an electrolyte containing MeCN and 0.002 M LiI to give mock-device conditions, $\eta_{eff}$ increased even further to >84% for each of the dyes where $\tau_{TiO2}$ was found to be beyond measurable limits. To understand the relative influence of the indolizine donor-based dyes AH3-AH6 on $\eta_{eff}$, we also measured $\tau_{sol}$ and $\tau_{TiO2}$ for the reference dyes CQ1, C1 and LS1 (Table 4). Solution fluorescence excited-state lifetimes were found to range from 2.24-1.88 ns for the reference series, which is only moderately lengthened when compared with AH3-AH6 (1.59-0.93 ns). $\tau_{TiO2}$ for the reference dyes was found to be <0.15 ns for each of the dyes on TiO2 films without the addition of any additives resulting in $\eta_{eff}$ values ranging from >93% to >92%. Indolizine dyes AH3-AH5, which show $\tau_{TiO2}$ values ranging from 0.30-0.26 ns without additives. Similar $\eta_{eff}$ values (>91% to >84%) to the reference dyes were obtained after addition of CDCA and LiI to the indolizine-based dye films.

TABLE 4

Excited-state lifetime measurements for dyes indolizine dyes AH3-AH6 as well as reference dyes CQ1, C1 and LS1.

| dye | $\tau_{sol}$ [ns][a)] | $\tau_{TiO2}$ [ns][b)] | $\eta_{eff}$ [%][b)] | $\tau_{TiO2}$ [ns][c)] | $\eta_{eff}$ [%][c)] | $\tau_{TiO2}$ [ns][d)] | $\eta_{eff}$ [%][d)] |
|---|---|---|---|---|---|---|---|
| AH3 | 1.14 | 0.30 | 74 | 0.30 | 74 | <0.15 | >86 |
| AH4 | 1.59 | 0.29 | 82 | 0.29 | 82 | <0.15 | >91 |
| AH5 | 0.93 | 0.34 | 63 | 0.26 | 72 | <0.15 | >84 |
| AH6 | 1.18 | 0.65 | 45 | 0.35 | 70 | <0.15 | >87 |
| CQ1 | 1.88 | <0.15 | >92 | <0.15 | >92 | <0.15 | >92 |
| C1 | 2.24 | <0.15 | >93 | <0.15 | >93 | <0.15 | >93 |
| LS1 | 2.18 | <0.15 | >93 | <0.15 | >93 | <0.15 | >93 |

[a)]Measurement made using dye dissolved in $CH_2Cl_2$.
[b)]Measurement made using dye-sensitized $TiO_2$ film in air with no additive.
[c)]Measurement made using dye-sensitized $TiO_2$ film with added CDCA.
[d)]Measurement made using dye-sensitized $TiO_2$ films with added CDCA and 0.002M LiI in MeCN electrolyte.

Example 5

Photovoltaic Performance

Having established the indolizine dye series exhibits suitable characteristics for productive photon-to-electric conversion, dyes AH3-AH6 were examined in DSC devices with a $TiO_2$ semiconductor and $I^-/I_3^-$ redox shuttle. From the equation PCE ($\eta$) % = $(J_{sc}V_{oc}FF)/I_{(sun)}$ where $J_{sc}$ = short-circuit current, $V_{oc}$ is the open-circuit voltage, FF is the fill factor and $I_{(sun)}$ is the incident light intensity, the device performances under AM 1.5 irradiation were analyzed (Table 5).

TABLE 5

Photovoltaic parameters measured under AM 1.5 incident light.[a)]

| dye | $J_{SC}$ [mA/cm$^2$] | $V_{OC}$ [mV] | FF | $\eta$ [%] |
|---|---|---|---|---|
| AH3 | 10.0 | 680 | 0.74 | 5.10 |
| AH4 | 8.06 | 560 | 0.69 | 3.10 |
| AH5 | 9.75 | 668 | 0.76 | 4.97 |
| AH6 | 10.8 | 670 | 0.74 | 5.36 |
| CQ1 | 10.3 | 707 | 0.69 | 4.99 |
| C1 | 9.72 | 787 | 0.71 | 5.45 |
| LS1 | 10.6 | 650 | 0.69 | 4.72 |

[a)]Devices were fabricated with the Z960 electrolyte which is comprised of: 1.0M 1,3-dimethylimidazolium iodide (DMII), 50 mM LiI, 30 mM $I_2$, 0.5M tert-butylpyridine, 0.1M guanidinium thiocyanate (GNCS) in acetonitrile and valeronitrile (v/v, 85/15)). Additional device fabrication data is in the Experimental Section below.

After device optimization with CDCA loadings to diminish aggregation, dye $J_{sc}$ values ranged from 8.1-10.8 mA/cm$^2$ in the order of AH6>AH3>AH5>AH4. AH6 has the longest wavelength absorption, which led to a significantly larger photocurrent than the remaining dyes. AH3, AH5 and AH6 demonstrated very similar $V_{oc}$ values (680-668 mV) and FF values (0.74-0.76) leading to a close range of PCEs from 5.0%-5.4% with AH6 demonstrating the overall highest PCE of 5.4%. AH4 demonstrated the lowest PCE due to lower performance in all parameters. The model indolizine donors employed in these studies utilized few aggregation controlling substituents and $TiO_2$ surface protecting alkyl chains, which are known to boost $V_{oc}$ values. The $V_{oc}$ values obtained for the indolizine-based dyes are similar to the reference dyes CQ1 and LS1. Superior PCE values were observed for AH6 when compared with these donors despite a potentially PCE-diminishing lower molar absorptivity and significant aggregation on the $TiO_2$ film surface. Among the common donors compared to the AH6 donor, only the bis(methyloxy)triphenylamine donor of C1 gives a similar PCE value due to a significantly higher $V_{oc}$.

Figure 6:
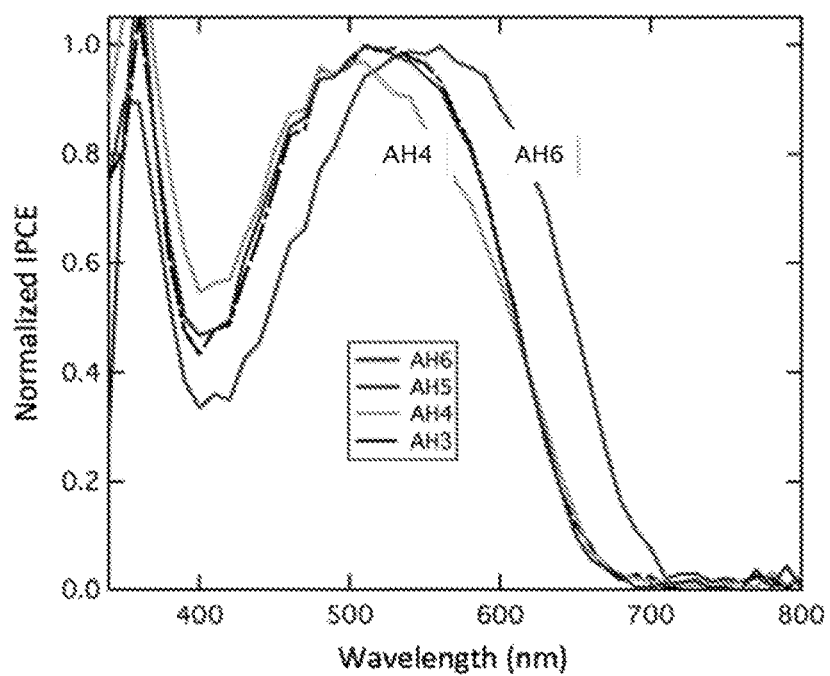
FIG. 6. IPCE curves for devices based on examples of the present invention.
Figure 7:
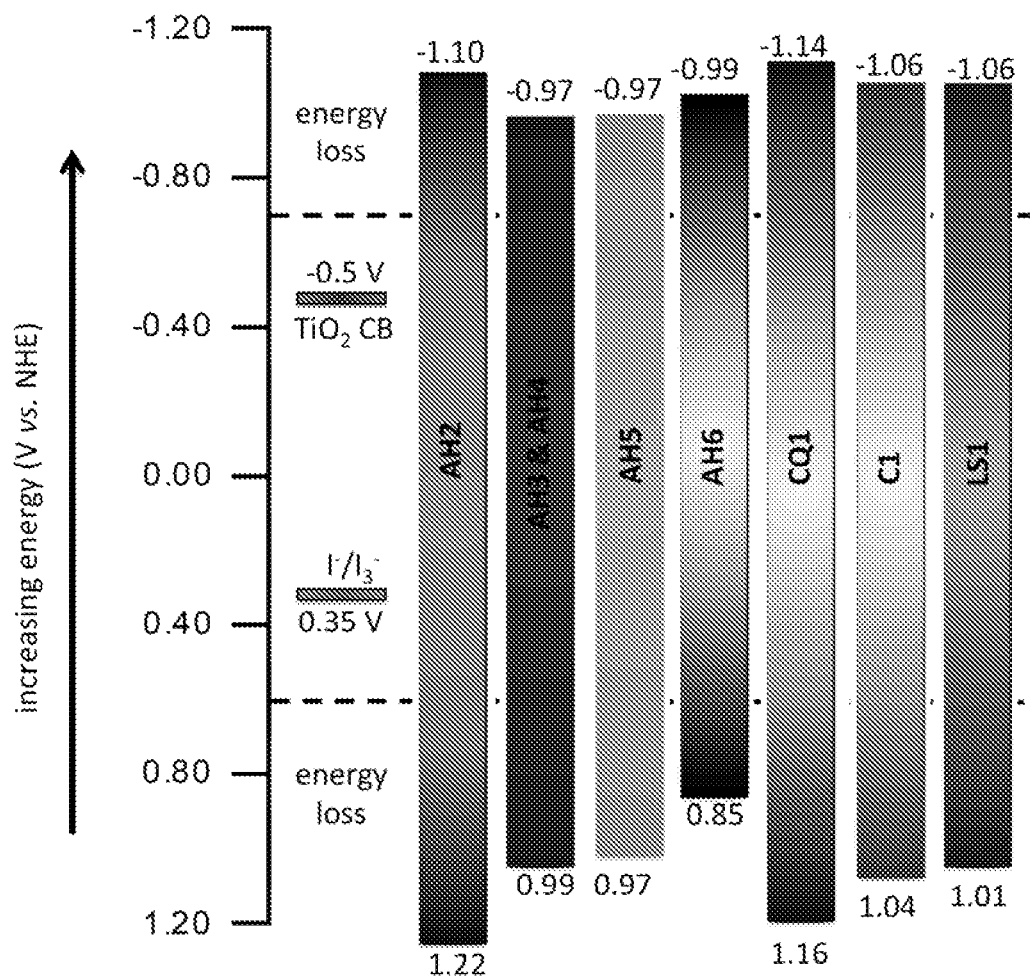
FIG. 7. Energy level schematics comparing the optical bandgaps of indolizine dyes of the present invention, (p-H)$_2$TPA (CQ1), (p-OMe)$_2$TPA (C1) and indoline (LS1) donors on T-CAA.

The incident photon-to-electron conversion efficiency (IPCE) spectra were measured for each of the dyes (FIG. 6). AH6 had the longest wavelength IPCE onset at ~700 nm which coincides with the largest $J_{sc}$ value observed. The remaining dyes (AH3-AH5) all have similar IPCE onset values of ~650 nm. Ranging from ~400-475 nm, a significant depression is observed for each of the dyes which mirrors the absorption spectral profiles of these sensitizers (FIG. 2) due to their low molar absorptivity (~2,000 $M^{-1}cm^{-1}$) in this region. Additionally, dye aggregation on $TiO_2$ films led to apparent lower injection efficiencies when fluorescence lifetime measurements were examined. These factors likely contribute to the observed peak maximum IPCE values reaching 70-75% for each of the dyes rather than >90%. However, the IPCE breadth is increased for the indolizine-based dyes relative to triphenyl amine and indoline-based dyes as a result of absorptions at longer wavelengths (650 nm vs. 700 nm onset). TPAs and indolines are two of the most common DSC donors in organic dye designs which are common to nearly all organic sensitizers with greater than 10% PCE. Indolizine donors exhibit broader solution absorption spectra (narrowed optical band-gap) compared with these donors ($\lambda_{onset}$=675 nm for AH6 versus $\lambda_{onset}$=540 nm for TPA-based CQ1, 590 nm for diMeO-TPA-based C1, and 600 nm for indoline-based LS1, (Table 1, FIG. 7) and increased performance beyond 650 nm in DSC devices (FIG. 6).

Example 6

This Example highlights a feature of the present invention, balanced donor and acceptor strengths. NIR absorbing dyes for use in DSC devices require balanced donor and acceptor strengths. Tunable, strong donors are needed for many electron deficient functionalities. We have synthesized a series of strong electron-donor building blocks based on indolizine which are planar, have reduced energy barriers to access excited-states, and have strong electron donation directionality to the dye acceptor regions. A range of indolizine-based dyes were synthesized in remarkably few steps (3-5) with substituent tunable donation strengths. The π-bridge and acceptor subunits were held constant to facilitate comparison to previously reported dyes from the literature. The dyes AH3-AH6 are observed to absorb further into the visible region than the reference dyes that utilized triarylamine or indoline, which is due to a destabilization of the $E_{(S+/S)}$ and a synergistic stabilization of the $E_{(S+/S^*)}$ energy levels. The cyanoacrylic acid carbonyl and nitrile vibrational stretches are significantly lower in frequency for indolizine dyes than for arylamine dyes, suggesting indolizine is a significantly stronger two-electron donor. Computational investigation of each dye indicates good charge transfer from the HOMO in the donor region to the LUMO in the acceptor region. Furthermore, a method for accurately predicting the $\lambda_{max}$ in $CH_2Cl_2$ was devised based on the inclusion of solvent both in the geometry optimization steps as well as the TD-DFT calculation of the appropriate vertical transitions. The electron injection efficiency of the dyes to the $TiO_2$ conduction band was also investigated. The indolizine dyes were found to have improved electron injection efficiency upon the addition of CDCA, which suggests aggregation is problematic for these model dyes. Through addition of CDCA and Li+ commonly found in the dye electrolyte, the electron injection efficiencies were increased to >91% to >84% for each dye. AH3-AH6 were evaluated in DSC devices using $TiO_2$ semiconductor and the $I^-/I_3^-$ redox shuttle. The dyes exhibited performance ranging from 3.1-5.4% PCE, which compared well to the reference dyes with arylamine donors. Low photon absorption in the 450-500 nm range and aggregation were observed to play key roles in diminishing the device photocurrent. The in-device $\lambda_{onset}$ reached near 700 nm for AH6, which incorporates significantly more photons in the visible spectrum than the reference dyes. The IPCE spectrum onset of the low molecular weight indolizine dye AH6 is within ~25 nm of high performance dyes (10-12.5% PCEs) such as Y123, YA422, C259 and ADEKA-1.

Example 7

This example demonstrates a method of making certain dyes of the present invention. All commercially obtained reagents were used as received. Thin-layer chromatography (TLC) was conducted with Sigma T-6145 pre-coated TLC Silica gel 60 $F_{254}$ polyester sheets and visualized with UV and potassium permanganate staining. Flash column chromatography was performed as described by Still using Sorbent Tech P60, 40-63 μm (230-400) mesh). $^1$H NMR spectra were recorded on a Bruker Avance-300 (300 MHz), Bruker Avance DRX-500 (500 MHz spectrometer and are reported in ppm using solvent as an internal standard ($CDCl_3$ at 7.26 ppm). Data reported as: s=singlet, d=doublet, t=triplet, q=quartet, p=pentet, m=multiplet, b=broad, ap=apparent; coupling constant(s) in Hz; integration. UV-Vis spectrum were measured with a Cary 5000 UV-Vis spectrometer. Cyclic voltammetry was measured with a C-H Instruments electrochemical analyzer.

Synthetic Route

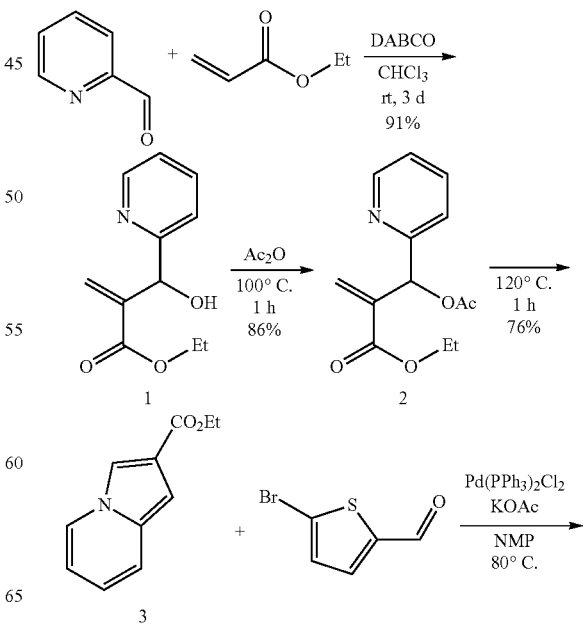

-continued
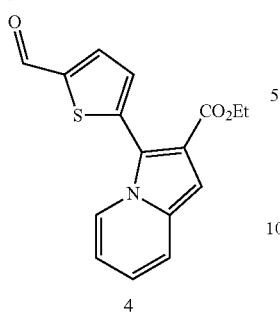
4
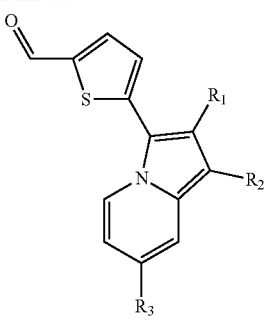
$R_1$ = Ph, $R_2$ = Me, $R_3$ = H, 11, 0.36g. 92%
$R_1$ = Ph, $R_2$ = Hex, $R_3$ = H, 12, 49%
$R_1$ = (4-OMe)Ph, $R_2$ = Me, $R_3$ = H, 13, 44%
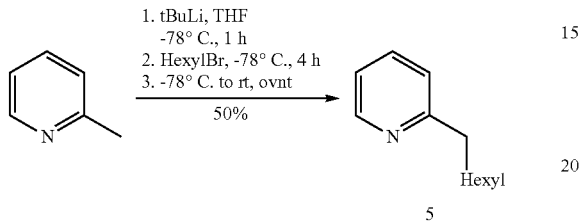
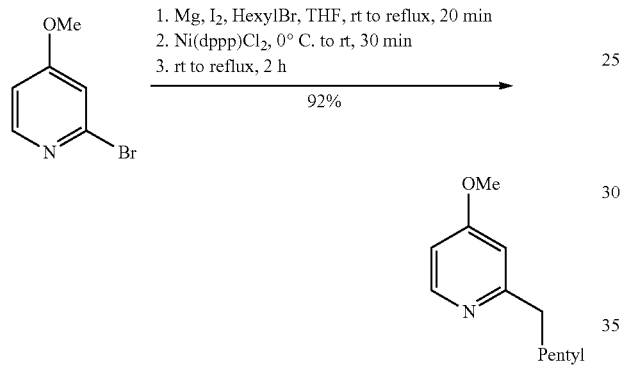
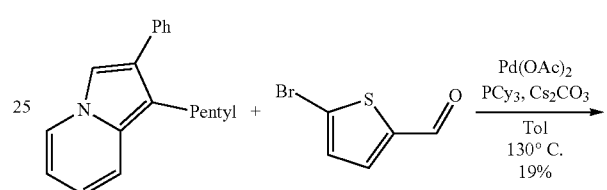
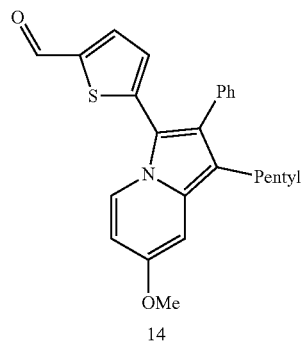
14
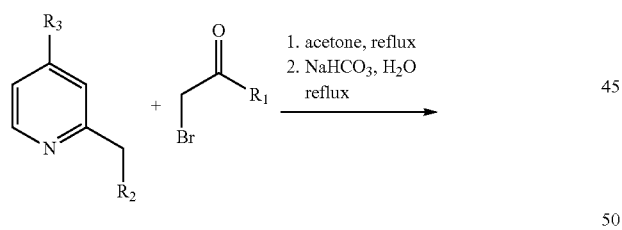
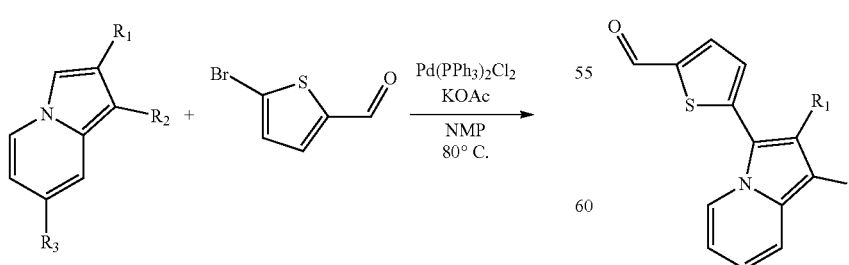
$R_1$ = Ph, $R_2$ = Me, $R_3$ = H, 7, 17.6 g. 92%
$R_1$ = Ph, $R_2$ = Hex, $R_3$ = H, 8, 1.51 g. 74%
$R_1$ = (4-OMe)Ph, $R_2$ = Me, $R_3$ = H, 9, 1.48 g. 78%
$R_1$ = Ph, $R_2$ = Hex, $R_3$ = OMe, 10, 0.10g, 16%
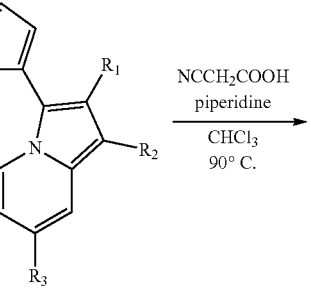

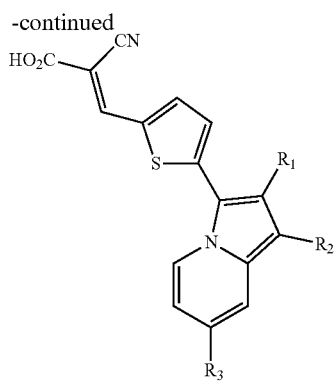

R$_1$ = CO$_2$Et, R$_2$ = H, R$_3$ = H, AH2, 84%
R$_1$ = Ph, R$_2$ = Me, R$_3$ = H, AH3, 25%
R$_1$ = Ph, R$_2$ = Hex, R$_3$ = H, AH4, 14%
R$_1$ = (4-OMe)Ph, R$_2$ = Me, R$_3$ = H, AH5, 49%
R$_1$ = Ph, R$_2$ = Hex, R$_3$ = OMe, AH6, 64%

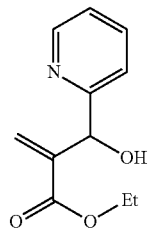

Ethyl 2-(hydroxy(pyridin-2'-yl)methyl)acrylate (1):[1] To a 50 mL round bottom flask was added pyridine-2-carboxaldehyde (5.63 g, 52.6 mmol, 1.0 equiv.), DABCO (0.340 g, 3.00 mmol, 0.05 equiv.), ethyl acrylate (5.52 g, 5.89 mL, 55.1 mmol, 1.05 equiv.), and chloroform (4.0 mL, 13.15 M). The mixture was allowed to stir for 3 d at room temperature. During this time the solution slowly changes colors from yellow to red. An aliquot was removed and the reaction was judged complete by TLC. The mixture was concentrated and subjected to flash chromatography using 350 mL SiO$_2$, 10× 160 mm collection tubes, and EtOAc as eluent. Collected product fractions concentrated to yield a yellow oil. (9.94 g, 48.0 mmol, 91%). $^1$H NMR (300 MHz, CDCl$_3$) δ 8.55 (dt, J=4.4 Hz, 1.0 Hz, 1H), 7.68 (td, J=7.6 Hz, 1.7 Hz, 1H), 7.43 (d, J=8.6 Hz, 1H), 7.23 (ddd, J=7.3 Hz, 5.1 Hz, 1 Hz, 1H), 6.36 (dd, J=2.0 Hz, 0.5 Hz, 1H), 5.95 (t, J=1.1 Hz, 1H), 5.62 (d, J=6.6 Hz, 1H), 4.80 (d, J=2.0 Hz, 1H), 4.18 (q, J=7.1 Hz, 2H), 1.24 (t, J=7.1 Hz, 3H).

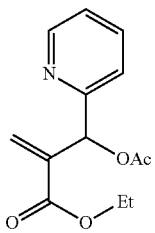 [SMILES: C=C(C(=O)OCC)C(OC(C)=O)c1ccccn1]

Ethyl 2-(acetoxy(pyridin-2'-yl)methyl)acrylate (2):[1] To a 25 mL flask was added Ethyl 2-(hydroxy(pyridin-2-yl)methyl)acrylate (7.00 g, 33.8 mmol, 1.0 equiv) and acetic anhydride (20 mL, 1.7 M). The mixture was heated to 100° C. with stirring. After 1 h, cooled to room temperature and diluted with EtOAc (100 mL). Washed sequentially with saturated NaHCO$_3$ (2×100 mL), H$_2$O (1×100 mL), and brine (2×100 mL). Dried organic solution with MgSO$_4$ and passed through thick pad of SiO$_2$ using 5% MeOH:EtOAc. Concentrated to yield a dark oil (7.20 g, 28.9 mmol, 86%). $^1$H NMR (300 MHz, CDCl$_3$) δ 8.59 (d, J=4.5 Hz, 1.0 Hz, 1H), 7.69 (td, J=7.5 Hz, 1.7 Hz, 1H), 7.45 (d, J=7.8 Hz, 1H), 7.22 (ddd, J=7.3 Hz, 3.8 Hz, 1.2 Hz, 1H), 6.74 (s, 1H), 6.49 (t, J=0.9 Hz, 1H), 5.94 (t, J=1.3 Hz, 1H), 4.15 (qd, J=7.0 Hz, 1.0 Hz, 2H), 2.16, (s, 3H), 1.21 (t, J=6.8 Hz, 3H).

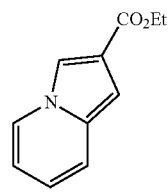

Ethyl(indolizine-2-carboxylate) (3):[1a] To a 25 mL flask was added ethyl 2-(acetoxy(pyridin-2-yl)methyl)acrylate (7.0 g, 28 mmol). The acrylate was set to stir at 120° C. under a nitrogen atmosphere. After 55 min, the reaction was judged complete by TLC. The reaction mixture was diluted in 50 mL 5% MeOH: EtOAc and passed through a thick pad of SiO$_2$ using 5% MeOH: EtOAc as eluent. Concentrated to give a dark solid (4.02 g, 21.2 mmol, 75%). $^1$H NMR (300 MHz, CDCl$_3$) δ 7.85 (d, J=6.3 Hz, 1.0 Hz, 1H), 7.80 (s, 1H), 7.36 (d, J==9.2 Hz, 1H), 6.83 (s, 1H), 6.68 (dd, J=9.0 Hz, 6.3 Hz 1H), 6.53 (td, J=6.9 Hz, 1.2 Hz, 1H), 4.35 (q, J=7.1 Hz, 2H), 1.38 (t, J=7.1 Hz, 3H).

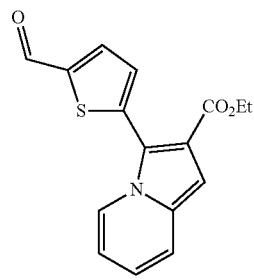 [SMILES: CCOC(=O)c1cc2ccccn2c1-c1ccc(C=O)s1]

Ethyl (1-(thiophen-2'-yl-5'-carboxaldehyde)indolizine)-2-carboxylate (4):[1] To a 25 mL flask was added Ethyl(indolizine-2-carboxylate) (0.12 g, 0.64 mmol), PdCl$_2$(PPh$_3$)$_2$ (0.037 g, 0.053 mmol), 5-bromo-2-thiophenecarboxaldehyde (0.30 g, 0.19 mL, 1.6 mmol), KOAc (0.21 g, 2.12 mmol), NMP (2.5 mL) under a nitrogen atmosphere. Set to stir at 80° C. After 20 h, subjected material to column chromatography using 10% EtOAc:Hexanes. Concentrated product spot to yield an orange solid (0.15 g, 0.50 mmol, 47%). $^1$H NMR (300 MHz, CDCl$_3$) δ 9.95 (s, 1H), 7.96 (d, J=8.1 Hz, 1H), 7.84 (d, J=4.0 Hz, 1H), 7.42 (d, J=8.5 Hz, 1H), 7.34 (d, J=3.7 Hz, 1H), 7.0 (s, 1H), 6.8 (t, J=7.3 Hz, 1H), 6.59 (t, J=7.0 Hz, 1H), 4.25 (q, J=7.2 Hz, 2H), 1.25 (t, J=7.3 Hz, 3H).

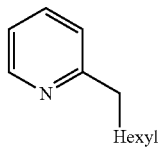

2-Heptylpyridine (5):[2] To a 100 mL flame-dried flask was added 2-picoline (2.0 g, 2.12 mL, 21.44 mmol), and THF (50 mL). This solution was cooled to −78° C. and t-Butyl lithium (15.12 mL, 1.7M) was added dropwise to yield a red-orange solution. Set to stir at −78° C. After 1 h, Hexylbromide (7.5 mL, 55.6 mmol) added dropwise at −78° C. Allowed reaction to warm to rt slowly with stirring. After 20 h. passed reaction mixture through thin pad of $SiO_2$ and concentrated to give a pale yellow liquid (1.90 g, 10.72 mmol, 50%). $^1$H NMR (300 MHz, $CDCl_3$) δ 8.51 (dq, J=5.0 Hz, 1.0 Hz, 1H), 7.57 (td, J=7.9 Hz, 1.8 Hz, 1H), 7.13 (d, J=7.8 Hz, 1H), 7.08 (dm, J=7.0 Hz, 1H), 2.77 (t, J=6.2 Hz, 2H), 1.72 (q, J=7.2 Hz, 2H), 1.38-1.21 (m, 9H), 0.87 (t, J=7.5 Hz, 3H).

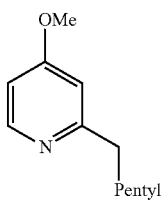

2-Hexyl-4-methoxypyridine (6):[3] To a 50 mL flame dried flask was added Mg (0.54 g, 22.16 mmol), THF (25 mL) and one crystal of $I_2$ under a nitrogen atmosphere. A drop of Hexyl bromide was added and once the reaction started the remaining was added via addition funnel (2.48 mL, 2.92 g, 17.7 mmol). Set to stir at reflux. After 20 min, the reaction was allowed to cool to rt. In a separate flame dried flask was added Ni(dppp)$Cl_2$ (0.29 g, 0.53 mmol), 2-bromo-4-methoxypyridine (1.0 g, 5.3 mmol), THF (25 mL) and the flask was cooled to 0° C. The Grignard solution was added to the pyridine solution via cannula at 0° C. and the reaction allowed to warm to rt with stirring. After 30 min, the reaction mixture was set to stir at reflux. After 2 h, the reaction mixture was diluted with 50 mL EtOAc, washed sequentially with sat'd $NaHCO_3$ (50 mL), brine (50 mL), and dried with $MgSO_4$. Filtered the solution and concentrated. Subjected crude product to flash chromatography using a gradient of Hexanes (500 mL) and EtOAc to yield an orange red oil (0.934 g, 4.85 mmol, 92%). $^1$H NMR (500 MHz, $CDCl_3$) δ δ 8.31 (dd, J=6.3 Hz, 0.7 Hz, 1H), 6.63 (t, J=2.5 Hz, 1H), 6.61 (t, J=3.1 Hz, 1H), 2.70 (t, 7.9 Hz, 2H), 1.69 (q, J=7.8 Hz, 2H), 1.34-1.22 (m, 6H), 0.88 (t, J=7.0 Hz, 3H).

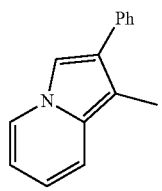 [SMILES: Cc1c(-c2ccccc2)cn2ccccc12]

2-Phenyl-3-methylindolizine (7):[4] To a 100 mL flask was added 2-ethylpyridine (10.0 g, 93.37 mmol), bromoacetophenone (18.58 g, 93.37 mmol), acetone (50 mL). Set to stir open to air at reflux. After 21 h, the reaction mixture was cooled to rt and the resulting white precipitate filtered and washed with acetone. The white solid was then added to a 250 mL flask, along with $NaHCO_3$ (31.00 g, 370.0 mmol). Set to stir open to air at reflux. After 1.5 h, a biphasic reaction mixture was observed and upon cooling the flask to rt, the top layer crystallized into a dark mass. Filtered the dark crystals and dissolved them in $CH_2Cl_2$. Passed through a thin pad of $SiO_2$ and concentrated to yield an off white solid (17.64 g, 85.11 mmol, 92%). $^1$H NMR (500 MHz, $CDCl_3$) δ δ 7.85 (dt, J=7.0 Hz, 0.9 Hz, 1H), 7.54 (d, J=7.7 Hz, 1H), 7.45 (t, 7.4 Hz, 1H), 7.39 (s, 1H), 7.35-7.29 (m, 2H), 6.61 (ddd, J=7.1 Hz, 6.4 Hz, 1.0 Hz, 1H), 6.42 (t, 6.8 Hz, 1H), 2.45 Hz (s, 3H). $^{13}$C NMR (125 MHz, $CDCl_3$) δ 136.3, 131.3, 129.4, 129.0, 128.7, 126.5, 125.1, 117.8, 115.9, 110.5, 110.1, 105.9, 9.9. IR (neat, $cm^{-1}$): 3067.7, 2919.3, 2862.0, 1602.8, 1457.6, 736.1. HRMS (ESI) m/z calculated for $C_{15}H_{13}N$ [M+H]$^+$: 208.1126, found 208.1182.

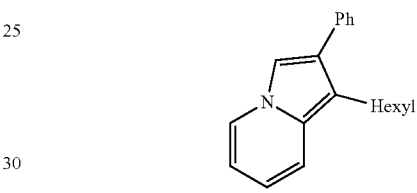

2-Phenyl-3-hexylindolizine (8): To a 50 mL flask was added 2-heptylpyridine (0.87 g, 4.9 mmol), bromoacetophenone (0.98 g, 4.9 mmol), acetone (10 mL). Set to stir open to air at reflux. After 21 h, the reaction mixture was cooled to rt and the solution concentrated. To the flask was added $NaHCO_3$ (1.64 g, 20. mmol). Set to stir open to air at reflux. After 8 h, the reaction mixture was cooled to rt and extracted with $CH_2Cl_2$ (3×15 mL) and passed through a thin pad of $SiO_2$. Concentrated to yield a dark green oil (1.0 g, 3.6 mmol, 74%). $^1$H NMR (300 MHz, $CDCl_3$) δ δ 7.85 (d, J=6.9 Hz, 1H), 7.48 (d, 6.8 Hz, 2H), 7.41 (t, J=7.0 Hz, 2H), 7.34 (d, J=7 Hz, 1H), 7.33 (s, 1H), 7.30 (m, 1H), 6.60 (ddd, J=7.8 Hz, 6.5 Hz, 1.0 Hz, 1H), 6.41 (t, J=6.6 Hz, 1H), 2.85 (t, 7.9 Hz, 2H), 1.57 (q, 7.3 Hz, 2H), 1.31 (q, J=6.6 Hz, 2H), 1.24 (m, 6H), 0.85 (t, J=7.0 Hz, 3H). $^{13}$C NMR (125 MHz, $CDCl_3$) δ 136.6, 131.0, 129.3, 129.2, 128.7, 126.6, 125.1, 118.0, 116.0, 111.8, 110.4, 110.2, 31.9, 29.7, 24.4, 23.0, 14.4. IR (neat, $cm^{-1}$): 3067.9, 2925.8, 2854.4, 1603.2, 1457.6, 734.6. HRMS (ESI) m/z calculated for $C_{20}H_{23}N$ [M+H]$^+$: 278.1909, found 278.1988.

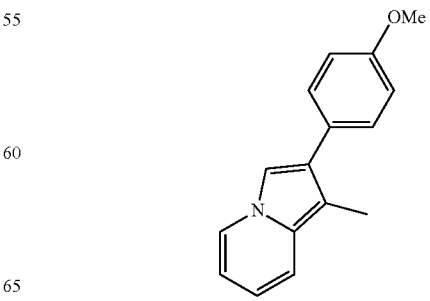

2-(4'-Methoxyphenyl)-3-methylindolizine (9): To a 25 mL flask was added 2-ethylpyridine (1.00 g, 10.7 mmol), bromoacetophenone (2.46 g, 10.7 mmol), acetone (5 mL). Set to stir open to air at reflux. After 16 h, the reaction mixture was cooled to rt and the resulting white precipitate was filtered. To a 25 mL flask was added the white precipitate, NaHCO$_3$ (4.00 g, 43.0 mmol). Set to stir open to air at reflux. After 3 h, reaction mixture was cooled to rt and the resulting dark precipitate filtered. The solid was dissolved in CH$_2$Cl$_2$ and through a thin pad of SiO$_2$. Concentrated to yield a yellowish oil that crystallized upon standing (2.0 g, 8.4 mmol, 78%). $^1$H NMR (500 MHz, CDCl$_3$) δ 7.84 (d, J=7.4 Hz, 1H), 7.46 (d, J=6.8 Hz, 2H), 7.34 (s, 1H), 7.32 (dd, J=8.4 Hz, 1.2 Hz, 1H), 6.99 (d, J=7.8 Hz, 2H), 6.60 (ddd, J=6.2 Hz, 6.4 Hz, 1.0 Hz, 1H), 6.40 (t, J=6.6 Hz, 1H), 3.85 (s, 3H), 2.42 (s, 3H). $^{13}$C NMR (125 MHz, CDCl$_3$) δ 158.6, 131.2, 130.0, 129.1, 128.8, 125.0, 117.7, 115.9, 114.3, 114.2, 110.2, 110.0, 105.7, 55.6, 9.9. IR (neat, cm$^{-1}$): 3069.4, 2997.9, 2833.6, 1610.6, 1246.6, 741.4. HRMS (ESI) m/z calculated for C$_{16}$H$_{15}$NO [M+H]$^+$: 238.1232, found 238.1251.

1-(thiophen-2'-yl-5'-carboxaldehyde)-2-phenyl-3-methylindolizine (11): To a 25 mL flame dried flask was added 2-Phenyl-3-methylindolizine (0.25 g, 1.2 mmol), PdCl$_2$(PPh$_3$)$_2$ (0.043 g, 0.061 mmol), 5-bromo-2-thiophenecarboxaldehyde (0.35 g, 0.22 mL, 1.8 mmol), KOAc (0.24 g, 2.4 mmol), NMP (2.5 mL) under a nitrogen atmosphere. Set to stir at 80° C. After 6.5 h, subjected material to column chromatography using 10% EtOAc:Hexanes. Concentrated product spot to yield an orange oil that crystallized upon standing (0.35 g, 1.1 mmol, 92%). $^1$H NMR (300 MHz, CDCl$_3$) δ 9.72 (s, 1H), 8.34 (d, J=6.8 Hz, 1H), 7.55 (d, J=4.0 Hz, 1H), 7.37-7.25 (m, 4H), 7.17 (d, J=6.0 Hz, 2H), 6.88 (d, J=4.0 Hz, 1H), 6.72 (ddd, J=7.8 Hz, 6.8 Hz, 1.0 Hz, 1H), 6.53 (t, J=6.3 Hz, 1H), 2.20 (s, 3H). $^{13}$C NMR (75 MHz, CDCl$_3$) δ 182.6, 143.5, 141.7, 136.9, 135.0, 132.7, 131.6, 130.8, 128.6, 127.4, 127.4, 123.0, 118.3, 118.0, 114.4, 112.1, 109.6, 9.3. IR (neat, cm$^{-1}$): 3067.5, 2860.9, 1660.2, 1434.8, 1226.6, 734.9. HRMS (ESI) m/z calculated for C$_{20}$H$_{15}$NOS [M]$^+$: 317.0874, found 317.0906.

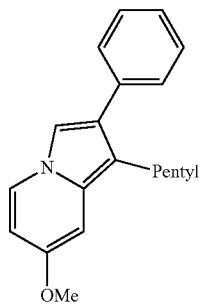

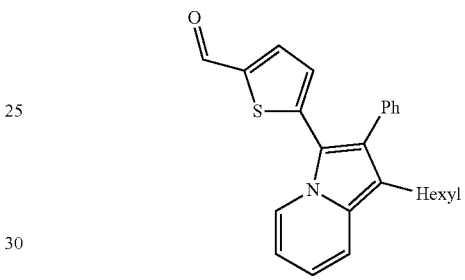

2-Phenyl-3-pentyl-5-methoxyindolizine (10): To a 25 mL flask was added 2-Hexyl-4-methoxypyridine (0.40 g, 2.1 mmol), bromoacetophenone (0.40 g, 2.1 mmol), acetone (15 mL). Set to stir open to air at reflux. After 16 h, the reaction mixture was cooled to rt and concentrated. To the flask was added NaHCO$_3$ (4.00 g, 43.0 mmol). Set to stir open to air at reflux. After 3 h, reaction mixture was cooled to rt and extracted with CH$_2$Cl$_2$ (3×25 mL) and concentrated. The crude product was subjected to column chromatography and the product spot concentrated to yield a dark oil (0.10 g, 0.32 mmol, 16%). $^1$H NMR (300 MHz, C$_6$D$_6$) δ 7.63 (dm, J=7.0 Hz, 2H), 7.33 (tm, J=8.1 Hz, 2H), 7.18 (dt, J=7.4 Hz, 1.3 Hz, 1H), 6.94 (dd, J=7.3 Hz, 0.7 Hz, 1H), 6.73 (s, 1H), 6.08 (d, J=2.5 Hz, 1H), 6.05 (dd, J=8.4 Hz, 2.6 Hz, 1H), 3.30 (s, 3H), 2.94 (t, J=7.6 Hz, 2H), 1.68 (m, 2H), 1.32-1.18 (m, 4H), 0.79 (t, J=7.0 Hz, 3H). $^{13}$C NMR (125 MHz, C$_6$D$_6$) δ 151.9, 137.4, 131.2, 130.3, 129.3, 128.8, 128.4, 126.6, 126.5, 109.7, 109.2, 105.6, 94.0, 54.6, 32.2, 31.5, 24.7, 22.9, 14.3. IR (neat, cm$^{-1}$): 3063.9, 2953.8, 2927.8, 1646.6, 1222.1, 769.7. HRMS (ESI) m/z calculated for C$_{20}$H$_{23}$NO [M+H]$^+$: 294.1858, found 294.1957.

1-(thiophen-2'-yl-5'-carboxaldehyde)-2-phenyl-3-hexylindolizine (11): To a 25 mL flame dried flask was added 2-Phenyl-3-hexylindolizine (0.25 g, 0.90 mmol), PdCl$_2$(PPh$_3$)$_2$ (0.032 g, 0.045 mmol), 5-bromo-2-thiophenecarboxaldehyde (0.26 g, 0.16 mL, 1.4 mmol), KOAc (0.18 g, 1.8 mmol), NMP (2.0 mL) under a nitrogen atmosphere. Set to stir at 80° C. After 20 h, subjected material to column chromatography using gradient of Hexanes to 5% EtOAc:Hexanes. Concentrated product spot to yield an orange oil that crystallized upon standing (0.17 g, 0.44 mmol, 49%). $^1$H NMR (500 MHz, CDCl$_3$) δ 9.80 (s, 1H), 8.45 (dt, J=8.1 Hz, 0.8 Hz, 1H), 7.61 (d, J=5.4 Hz, 1H), 7.45 (dt, J=8.0 Hz, 1.2 Hz, 1H), 7.39-7.32 (m, 3H), 7.25, (m, 2H), 6.94 (d, J=4 Hz, 1H), 6.80 (ddd, J=9.7 Hz, 6.3 Hz, 1.0 Hz, 1H), 6.61 (td, J=7.2 Hz, 1.3 Hz, 1H), 2.68 (t, J=8.0 Hz, 2H), 1.48 (m, 2H), 1.27-1.15 (m, 6H), 0.83 (t, J=6.7 Hz, 3H). $^{13}$C NMR (125 MHz, CDCl$_3$) δ 182.6, 143.7, 141.5, 137.0, 135.2, 132.8, 131.7, 130.9, 128.6, 127.5, 127.2, 127.1, 123.3, 123.2, 118.3, 118.2, 115.5, 114.7, 112.1, 3.8, 31.6, 29.5, 24.2, 22.9, 14.4. IR (neat, cm$^{-1}$): 3067.6, 2925.8, 1661.1, 1435.4, 1225.8, 700.7. HRMS (ESI) m/z calculated for C$_{25}$H$_{24}$NOS [M]$^+$: 387.1657, found 387.1754.

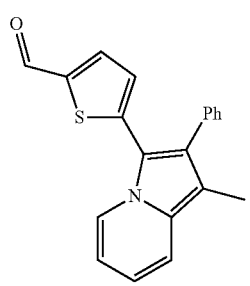 [SMILES: Cc1c(-c2ccccc2)c(-c2ccc(C=O)s2)n2ccccc12]

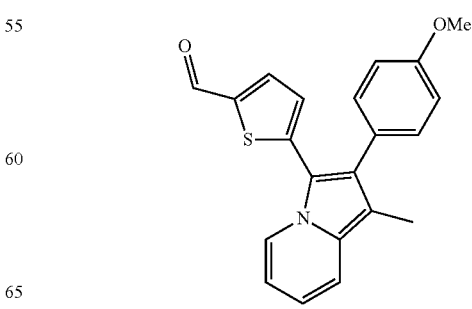

1-(thiophen-2'-yl-5'-carboxaldehyde)-2-(4"-methoxyphenyl)-3-methylindolizine (11): To a 25 mL flame dried flask was added 2-(4'-Methoxyphenyl)-3-methylindolizine (0.25 g, 1.1 mmol), PdCl$_2$(PPh$_3$)$_2$ (0.037 g, 0.053 mmol), 5-bromo-2-thiophenecarboxaldehyde (0.30 g, 0.19 mL, 1.6 mmol), KOAc (0.21 g, 2.1 mmol), NMP (2.0 mL) under a nitrogen atmosphere. Set to stir at 80° C. After 23 h, subjected material to column chromatography using gradient of 5% EtOAc:Hexanes to 20% EtOAc:Hexanes. Concentrated product spot to yield an orange oil that crystallized upon standing (0.16 g, 0.46 mmol, 44%). $^1$H NMR (500 MHz, CDCl$_3$) δ 9.82 (s, 1H), 8.42 (dt, J=7.2 Hz, 1.3 Hz, 1H), 7.63 (d, J=4.2 Hz, 1H), 7.41 (dt, J=8.9 Hz, 0.5 Hz, 1H), 7.17 (dm, J=8.2 Hz, 2H), 6.99 (d, J=3.9 Hz, 1H), 6.91 (dm, J=8.6 Hz, 2H), 6.79 (ddd, J=8.9 Hz, 6.6 Hz, 1.0 Hz, 1H), 6.60 (td, J=6.7 Hz, 1.4 Hz, 1H), 3.85 (s, 3H), 2.26 (s, 3H). $^{13}$C NMR (125 MHz, CDCl$_3$) δ 182.7, 159.2, 143.8, 141.6, 137.0, 132.9, 131.9, 131.4, 127.2, 127.1, 123.1, 118.4, 118.0, 114.5, 114.3, 114.2, 112.0, 109.7, 55.5, 9.4. IR (neat, cm$^{-1}$): 3032.3, 2934.2, 1659.0, 1431.1, 1247.1, 737.0.

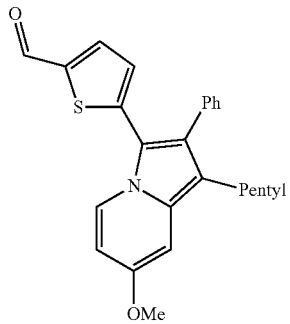

1-(thiophen-2'-yl-5'-carboxaldehyde)-2-phenyl-3-pentyl-5-methoxyindolizine (11): To a 25 mL flame dried flask was added 2-phenyl)-3-pentyl-5-methoxyindolizine (0.25 g, 1.1 mmol), Pd(OAc)$_2$ (0.037 g, 0.053 mmol), 5-bromo-2-thiophenecarboxaldehyde (0.30 g, 0.19 mL, 1.6 mmol). KOAc (0.21 g, 2.1 mmol), NMP (2.0 mL) under a nitrogen atmosphere. Set to stir at 80° C. After 23 h, subjected material to column chromatography using gradient of 5% EtOAc:Hexanes to 20% EtOAc:Hexanes. Concentrated product spot to yield an orange oil that crystallized upon standing (0.16 g, 0.46 mmol, 44%). $^1$H NMR (300 MHz, CDCl$_3$) δ 9.76 (s, 1H), 8.38 (dd, J=7.5 Hz, 0.7 Hz, 1H), 7.57 (d, J=4.0 Hz, 1H), 7.38-7.32 (m, 3H), 7.25-7.22 (m, 2H), 6.85 (d, J=4.0 Hz, 1H), 6.62 (d, J=2.7 Hz, 1H), 6.38 (dd, J=7.1 Hz, 2.7 Hz, 1H), 3.87 (s, 3H), 2.6 (t, J=7.6 Hz, 2H), 1.45 (m, 2H), 1.3-1.2 (m, 4H), 0.85 (t, J=6.4 Hz, 3H).

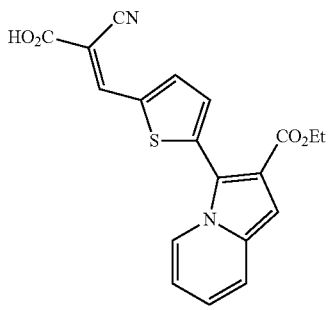 [SMILES: CCOC(=O)c1cc2ccccn2c1-c1ccc(/C=C(\C#N)C(=O)O)s1]

3-(ethyl(thiophen-2"-yl-5"-3-pentyl-indolizine-2-carboxylate)-2-cyano-2-propenoic acid (AH2). To a 10 mL flask added Ethyl (1-(thiophen-2'-yl-5'-carboxaldehyde)indolizine)-2-carboxylate (0.085 g, 0.29 mmol), CHCl$_3$ (4.75 mL). Bubbled with nitrogen for 30 min. Cyanoacetic acid (0.14 g, 1.7 mmol), piperidine (0.33 g, 0.39 mL, 4.0 mmol) added. Sealed flask using a plastic stopper and electrical tape. Warmed to 90° C. After 4.5 h, cooled to rt. Diluted with 150 mL CH$_2$Cl$_2$, acidified with AcOH, washed with H$_2$O (3×100 mL), Concentrated. Passed crude material through thick pad of SiO$_2$ using first CH$_2$Cl$_2$ (500 mL), then 10% MeOH:CH$_2$Cl$_2$ (500 mL), and finally 10% MeOH:5% AcOH:CH$_2$Cl$_2$ (500 mL). Concentrated to yield a dark range powder (0.084 g, 0.23 mmol, 84%). $^1$H NMR (500 MHz, CDCl$_3$). δ 8.35 (d, J=6.3 Hz, 1H), 7.90 (d, J=4 Hz, 1H), 7.84 (s, 1H), 7.4 (d, J=6.0 Hz, 1H), 7.35 (d, J=4.0 Hz, 1H), 7.0 (s, 1H), 6.8 (t, J=6.5 Hz, 1H), 6.6 Hz (t, J=6.6 Hz), 4.25 (q, J=7.0 Hz, 2H), 1.37 (t, J=7.1 Hz, 3H). HRMS (ESI) m/z calculated for C$_{19}$H$_{14}$N$_2$O$_4$S [M]$^+$: 367.0753, found 367.0707. UV-Vis (CHCl$_3$): λ$_{max}$=430 nm (ε= 1,250 M$^{-1}$cm$^{-1}$), λ$_{onset}$=530 nm.

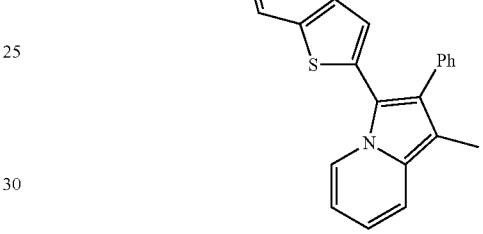

3-(thiophen-2'-yl-5'-2-phenyl-3-methylindolizine)-2-cyano-2-propenoic acid (AH3). To a 10 mL flask added 1-(thiophen-2'-yl-5'-carboxaldehyde)-2-phenyl-3-methylindolizine (0.10 g, 0.32 mmol), CHCl$_3$ (5.3 mL). Bubbled with nitrogen for 30 min. Cyanoacetic acid (0.086 g, 0.95 mmol), piperidine (0.19 g, 0.22 mL, 2.2 mmol) added. Sealed flask using a plastic stopper and electrical tape. Warmed to 90° C. After 20 h, cooled to rt. Diluted with 150 mL CH$_2$Cl$_2$, acidified with AcOH, washed with H$_2$O (3×100 mL), Concentrated. Passed crude material through thick pad of SiO$_2$ using first CH$_2$Cl$_2$ (500 mL), then 10% MeOH:CH$_2$Cl$_2$ (500 mL), and finally 10% MeOH:5% AcOH:CH$_2$Cl$_2$ (500 mL). Washed product fraction with H$_2$O (3×100 mL), dried with MgSO$_4$, filtered and concentrated to yield a dark purple powder (0.032 g, 0.079 mmol, 25%). $^1$H NMR (300 MHz, CDCl$_3$) δ 8.26 (d, J=6.4 Hz, 1H), 8.04 (m, 1H), 7.36 (m, 1H), 7.29 (m, 1H), 7.25 (m, 1H), 7.22 (m, 2H), 7.08 (m, 2H), 6.67 (t, J=7.9 Hz, 1H), 6.55 (m, 1H), 6.42 (m, 1H), 2.15 (s, 3H). IR (neat, cm$^{-1}$): 3429.1, 1645.5, 1394.9, 1199.1. HRMS (ESI) m/z calculated for C$_{23}$H$_{16}$N$_2$O$_2$S [M]$^+$: 385.1011, found 385.0549. UV-Vis (CHCl$_3$): λ$_{max}$=557 nm (ε=8,500 M$^{-1}$cm$^{-1}$), λ$_{onset}$=627 nm.

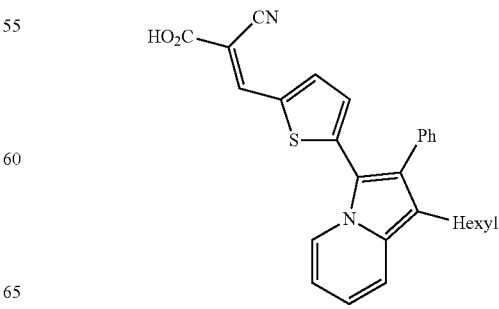

3-(thiophen-2'-yl-5'-2-phenyl-3-hexylindolizine)-2-cyano-2-propenoic acid (AH4). To a 10 mL flask added 1-(thiophen-2'-yl-5'-carboxaldehyde)-2-phenyl-3-hexylindolizine (0.13 g, 0.34 mmol), CHCl$_3$ (5.0 mL). Bubbled with nitrogen for 30 min. Cyanoacetic acid (0.086 g, 0.95 mmol), piperidine (0.19 g, 0.22 mL, 2.2 mmol) added. Sealed flask using a plastic stopper and electrical tape. Warmed to 90° C. After 20 h, cooled to rt. Diluted with 150 mL CH$_2$Cl$_2$, acidified with AcOH, washed with H$_2$O (3×100 mL), Concentrated. Passed crude material through thick pad of SiO$_2$ using first CH$_2$Cl$_2$ (500 mL), then 10% MeOH:CH$_2$Cl$_2$ (500 mL), and finally 10% MeOH:5% AcOH:CH$_2$Cl$_2$ (500 mL). Washed product fraction with H$_2$O (3×100 mL), dried with MgSO$_4$, filtered and concentrated to yield a dark purple powder (0.022 g, 0.048 mmol, 14%). $^1$H NMR (300 MHz, CDCl$_3$). δ 8.58 (d, J=7.3 Hz, 1H), 8.2 (s, 1H), 7.71 (m, 1H), 7.5 (m, 1H), 7.4 (m, 4H), 6.9 (m, 2H), 6.73 (m, 2H), 2.68 (m, 2H), 1.49 (m, 2H), 1.25 (m, 6H), 0.85 (t, J=6.9 Hz, 3H). HRMS (ESI) m/z calculated for C$_{28}$H$_{26}$N$_2$O$_2$S [M]$^+$: 455.1793, found 415.1274. UV-Vis (CHCl$_3$): λ$_{max}$=563 nm (ε=11,300 M$^{-1}$cm$^{-1}$), λ$_{onset}$=627 nm.

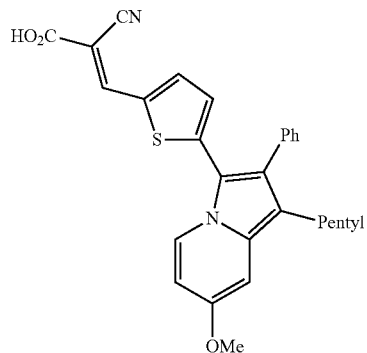

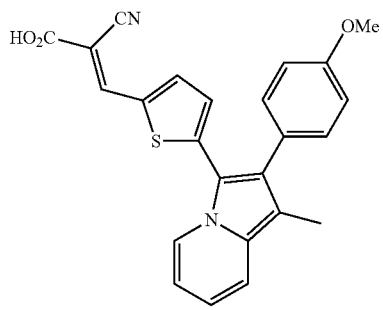 [SMILES: COc1ccc(-c2c(C)c3ccccn3c2-c2ccc(/C=C(\C#N)C(=O)O)s2)cc1]

3-(thiophen-2'-yl-5''-(4'''-methoxyphenyl)-3''-methyl-indolizine)-2-cyano-2-propenoic acid (AH5). To a 10 mL flask added 1-(thiophen-2'-yl-5'-carboxaldehyde)-2''-(4'''-methoxyphenyl)-3''-hexylindolizine (0.16 g, 0.45 mmol), CHCl$_3$ (7.0 mL). Bubbled with nitrogen for 30 min. Cyanoacetic acid (0.11 g, 1.3 mmol), piperidine (0.27 g, 0.31 mL, 3.1 mmol) added. Sealed flask using a plastic stopper and electrical tape. Warmed to 90° C. After 22 h, cooled to rt. Diluted with 150 mL CH$_2$Cl$_2$, acidified with AcOH, washed with H$_2$O (3×100 mL), Concentrated. Passed crude material through thick pad of SiO$_2$ using first CH$_2$Cl$_2$ (500 mL), then 10% MeOH:CH$_2$Cl$_2$ (500 mL), and finally 10% MeOH:5% AcOH:CH$_2$Cl$_2$ (500 mL). Washed product fraction with H$_2$O (3×100 mL), dried with MgSO$_4$, filtered and concentrated to yield a dark purple powder (0.090 g, 0.22 mmol, 49%). $^1$H NMR (300 MHz, CDCl$_3$). δ 8.60 (d, J=6.9 Hz, 1H), 8.25 (s, 1H), 7.75 (d, J=4.0 Hz, 1H), 7.47 (d, J=8.8 Hz, 1H), 7.24 (d, J=6.6 Hz, 2H), 6.9 (d, J=6.6 Hz, 2H), 6.97 (d, J=4.0 Hz, 1H), 6.92 (dd, J=8.2 Hz, 7.0 Hz, 1H), 6.74 (td, J=7.0 Hz, 1.3 Hz, 1H), 3.90 (s, 3H), 2.28 (s, 3H). IR (neat, cm$^{-1}$): 3422.3, 2964.1, 1648.6, 1402.1, 1207.2. HRMS (ESI) m/z calculated for C$_{24}$H$_{18}$N$_2$O$_3$S [M]$^+$: 415.1116, found 415.1130. UV-Vis (CHCl$_3$): λ$_{max}$=554 nm (ε=5,800 M$^{-1}$cm$^{-1}$), λ$_{onset}$=634 nm.

3-(thiophen-2'-yl-5'-2'''-phenyl-3''-pentyl-5''-methoxyindolizine)-2-cyano-2-propenoic acid (AH6). To a 10 mL flask added 1-(thiophen-2'-yl-5'-carboxaldehyde)-2''-(4'''-methoxyphenyl)-3''-hexylindolizine (0.025 g, 0.072 mmol), CHCl$_3$ (1.2 mL). Bubbled with nitrogen for 30 min. Cyanoacetic acid (0.018 g, 022 mmol), piperidine (0.043 g, 0.050 mL, 0.50 mmol) added. Scaled flask using a plastic stopper and electrical tape. Warmed to 90° C. After 45 min, cooled to rt. Diluted with 150 mL CH$_2$Cl$_2$, acidified with AcOH, washed with H$_2$O (3×100 mL), Concentrated. Passed crude material through thick pad of SiO$_2$ using first CH$_2$Cl$_2$ (500 mL), then 10% MeOH:CH$_2$Cl$_2$ (500 mL), and finally 10% MeOH:5% AcOH:CH$_2$Cl$_2$ (500 mL). Washed product fraction with H$_2$O (3×100 mL), dried with MgSO$_4$, filtered and concentrated to yield a dark purple powder (0.018 g, 0.043 mmol, 60%). $^1$H NMR (300 MHz, CDCl$_3$) δ 8.53 (d, J=7.3 Hz, 1H), 8.14 (s, 1H), 7.60 (m, 1H), 7.40 (m, 4H), 7.20 (m, 1H), 6.72 (d, J=4.1 Hz, 1H), 6.65 (m, 1H), 6.51 (m, 1H), 6.48 (m, 1H), 3.91 (s, 3H), 2.57 (t, J=7.1 Hz, 2H), 1.66 (m, 2H), 1.43 (m, 4H), 0.83 (t, J=6.7 Hz, 3H). HRMS (ESI) m/z calculated for C$_{28}$H$_{26}$N$_2$O$_3$S [M]$^+$: 471.1742, found 471.1260. UV-Vis (CHCl$_3$): λ$_{max}$=597 nm (ε=12,500 M$^{-1}$cm$^{-1}$). λ$_{onset}$=665 nm.

Example 8

This example demonstrates discusses certain embodiments of the present invention. As shown below, these examples exhibit excellent light absorption and surface blocking properties. Device efficiencies using either I$^-$/I$_3$$^-$ or Co(bpy)$_3$$^{III/II}$ electrolyte were significantly higher for AH7 (8.10%) than known dye D35. The dyes in this example are of the D-π-A type.

AH3

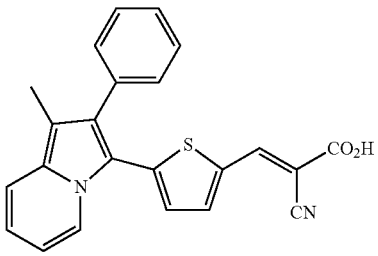

-continued

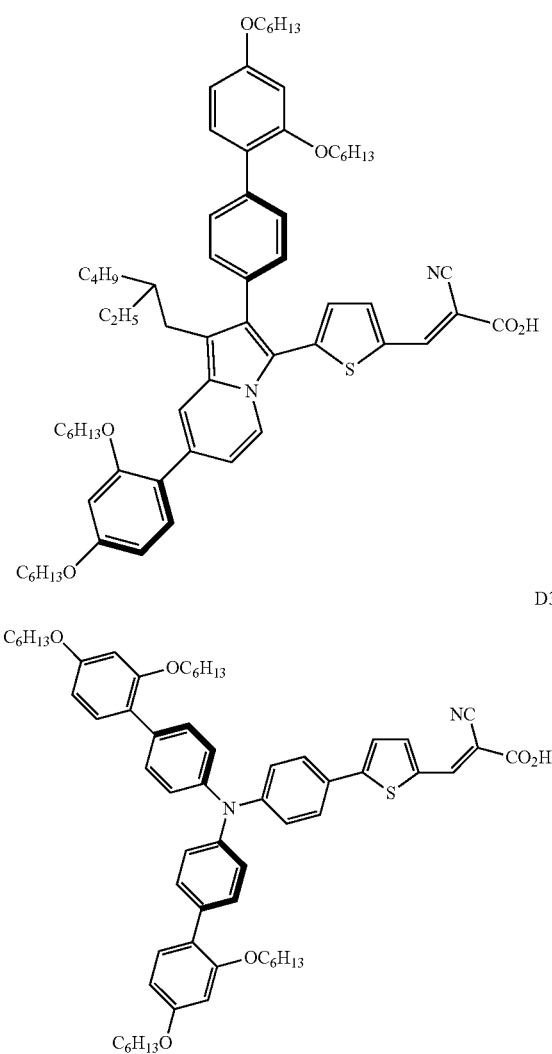

The optical and electronic properties of dye AH7 were then analysed through UV-Vis absorption and cyclic voltammetry (See Table 6, below). Compared to the non-blocking donor present in AH3, the $\lambda_{max}$ and $\lambda_{onset}$ of AH7 are both red-shifted by 50 nm, and the absorption coefficient is slightly increased. Compared to known dye D35, both values for dye AH7 are red-shifted by 160 nm, while the absorption coefficient is much lower.

TABLE 6

Optical and electronic properties.

| Dye | $\lambda_{max}$ (nm)[a] | $\lambda_{onset}$ (nm)[a] | (ε Lmol$^{-1}$ cm$^{-1}$)[a] | $E_g^{opt}$ (eV)[b] | $E_{(S+/S*)}$ (V)[c] | $E_{(S+/S)}$ (V)[d] |
|---|---|---|---|---|---|---|
| AH3 | 553 | 633 | 8,500 | 2.06 | −0.98 | 0.99 |
| AH7 | 605 | 685 | 9,350 | 1.81 | −0.93 | 0.87 |
| D35 | 445 | 525 | 70,100 | 2.36 | −1.32 | 1.04 |

[a]Measured in CH$_2$Cl$_2$ and 0.5% AcOH;
[b]Estimated from maximum absorption curve in CH$_2$Cl$_2$. Conversion from nanometers to eV was calculated by $E_{gopt} = 1240/\lambda_{onset}$. $E_{(0,0)}$;
[c]Measured in a 0.1M Bu$_4$NPF$_6$ in CH$_2$Cl$_2$ solution with glassy carbon working electrode, Pt reference electrode, and Pt counter electrode with ferrocene as an internal standard. Values are reported versus NHE;
[d]Calculated from $EE_{(S+/S*)} = E_{(S+/S)} - E_{gopt}$;

The ground state oxidation potential ($E_{(S+/S)}$) for AH7 was observed to be substantially higher in energy for AH7 than AH3 or D35, which was attributed to a much stronger donor on AH7. The Excited state oxidation potential ($E_{(S+/S*)}$) was also found to be much lower for AH7 than D35 and only somewhat lower than AH3, which was attributed to synergistic band-gap narrowing due to competing local aromaticity present in the indolizine subunit. Thus, AH7 was observed to have suitable energy levels to function as a DSC sensitizer. Dyes AH3, AH7, D35 were examined in DSC devices with a TiO$_2$ semiconductor and I$^-$/I$_3^-$ or Co$^{III/II}$ redox shuttle. From the equation PCE $(\eta)\% = (J_{sc}V_{oc}FF)/I_{(sun)}$ where $J_{sc}$=short-circuit current, $V_{oc}$ is the open-circuit voltage, FF is the fill factor and I(sun) is the incident light intensity, the device performances under AM 1.5 irradiation were analysed (Table 2).

TABLE 2

Device Performance.

| Dye | Electrolyte | $J_{sc}$ (mA/cm$^2$) | $V_{oc}$ (mV) | FF | η (%) |
|---|---|---|---|---|---|
| AH3 | 960[a] | 9.0 | 545 | 0.75 | 3.74 |
| AH7 | 960[a] | 14.7 | 696 | 0.76 | 7.99 |
| D35 | 960[a] | 11.5 | 758 | 0.74 | 6.58 |
| AH3 | Co(bpy)$_3$(II/III)[b] | 6.0 | 630 | 0.78 | 3.04 |
| AH7 | Co(bpy)$_3$(II/III)[b] | 13.5 | 757 | 0.78 | 8.10 |
| D35 | Co(bpy)$_3$(II/III)[b] | 10.2 | 829 | 0.74 | 6.40 |

[a]Devices were fabricated with the Z960 electrolyte that is comprised of: 1.0M 1,3-dimethylimidazolium iodide (DMII), 50 mM LiI, 30 mM I2, 0.5M tert-butyl-pyridine, 0.1M guanidinium thiocyanate (GNCS) in acetonitrile and valeronitrile (v/v, 85/15)). Additional device fabrication data is in the Experimental Section in the Supporting Information.
[b]Co-bpy electrolyte High efficiency DSC sensitizers not only need strong donors balanced with strong acceptors, they need to be sufficiently surface blocking in order to reduce non-productive electron transfer events such as recombination of electrons from TiO$_2$ to the redox shuttle. We have synthesized a surface blocking indolizine donor in 4 steps from commercially available starting materials. The dye AH7 was observed to observe significantly more light than either comparison dyes AH3 or D35, due to the competing local aromaticity inherent to the indolizine subunit and the very strong indolizine donor. In evaluating this series of dyes, the highest performing in devices was AH7. In comparing the performance of devices sensitized with either non-blocking indolizine donor (AH3), surface blocking donor (AH7), or well-known Hagfeldt donor (D35), the recombination rate improved in the order AH3>AH7>D35, with D35 reducing recombination rate to a lavel an order of magnitude lower than AH7. To further improve indolizine dyes, more advanced bridges, such as those incorporated in state-of-the art dyes should be incorporated.[10,14-16] Also, efforts to planarize the donor-bridge dihedral angle would significantly aid photon-to-electric conversion, as the absorption coefficient for AH7 was still quite low.

Example 9

This example described methods of making certain dyes of the present invention.

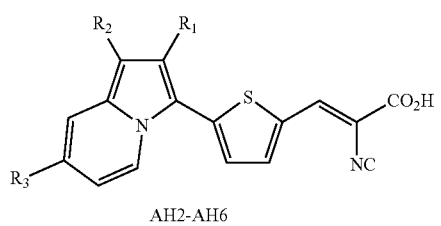
AH2-AH6
R₁ = —CO₂Et  R₂ = —H, R₃ = H AH2
R₁ = Ph  R₂ = —CH₃, R₃ = H AH3
R₁ = Ph  R₂ = —C₆H₁₃, R₃ = H AH4
R₁ = -(4-OMe)Ph, R₂ = —Me, R₃ = H AH5
R₁ = Ph  R₂ = —C₅H₁₈, R₃ = OMe AH6
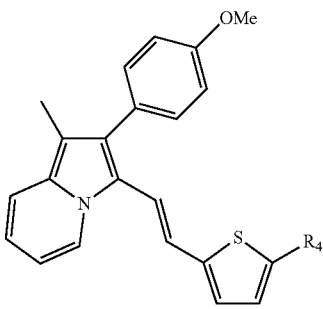
AH13, 14, 25
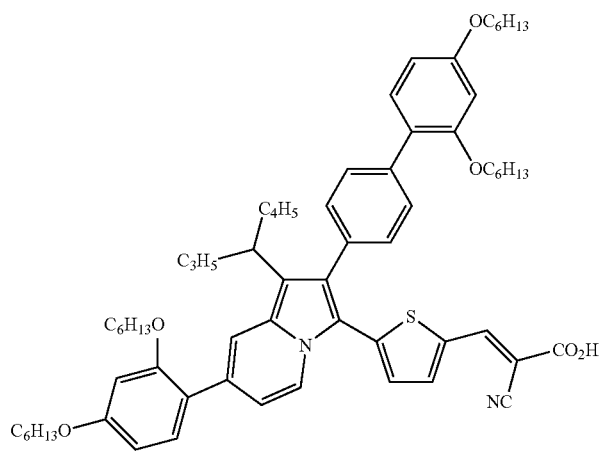
AH7
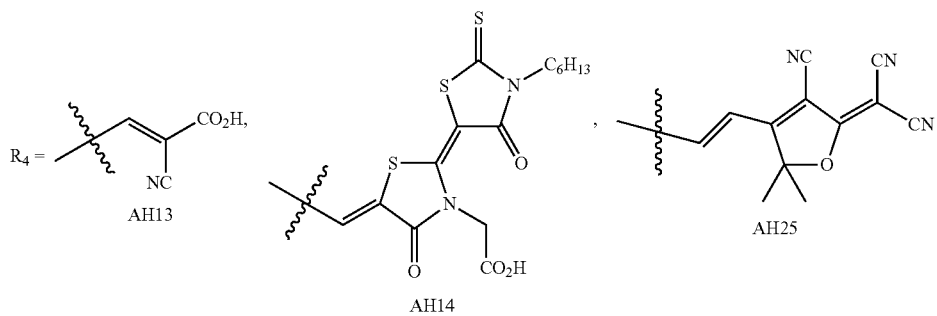
AH13    AH14    AH25
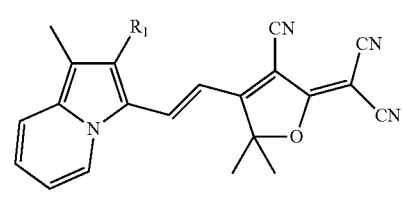
R₁ = —C₆H₄(4-CH₂CH₂CO₂H) DP3
    -(4-OCH₃)Ph DP4
DP3, DP4
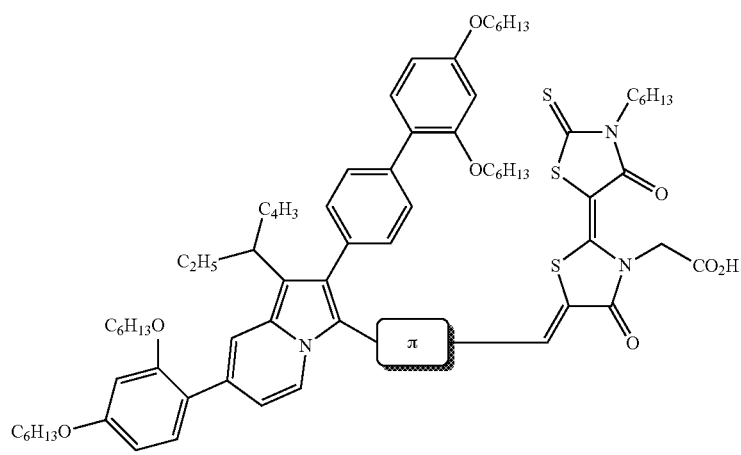
π = Thi, AH10
π = n/a, AH11

-continued
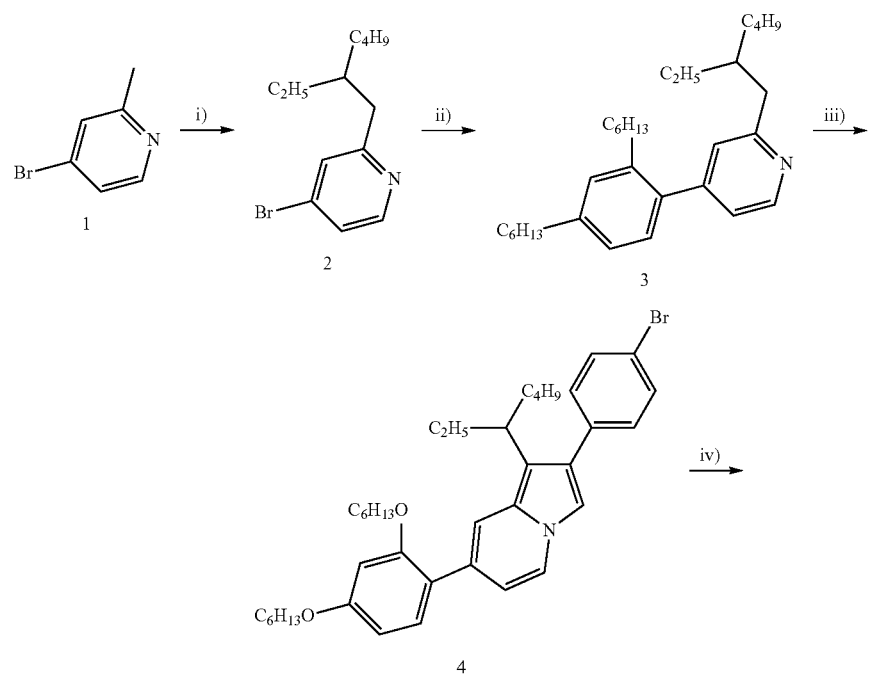
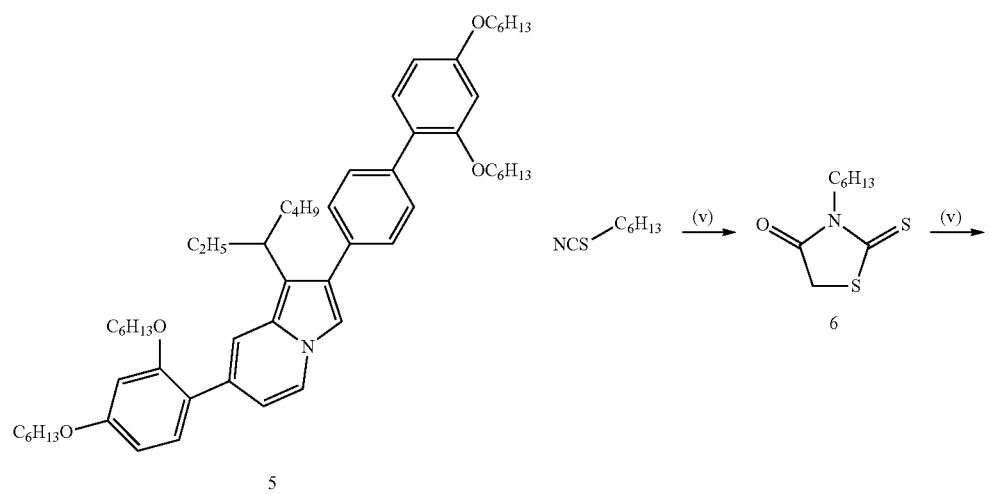
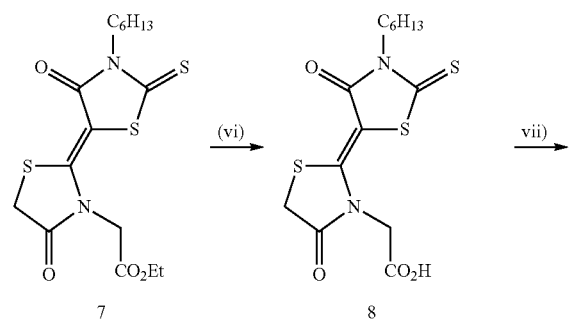

-continued
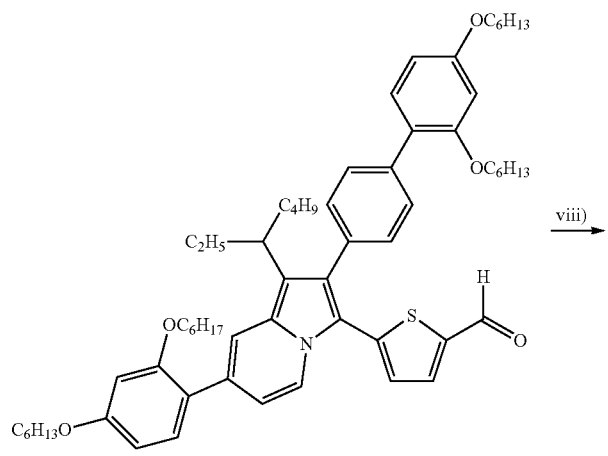
9
viii)
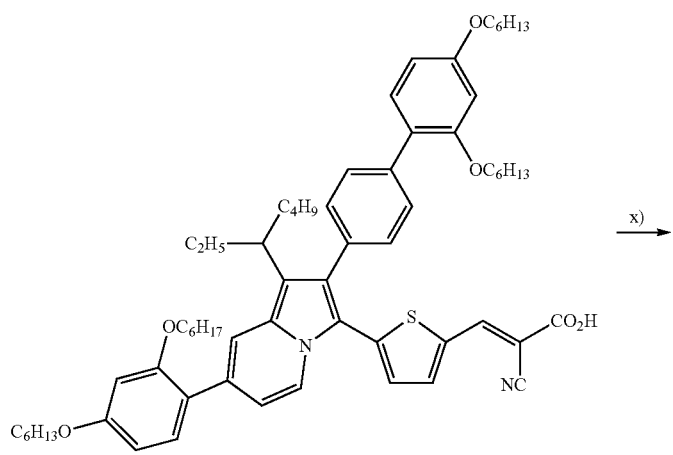
AH7
x)
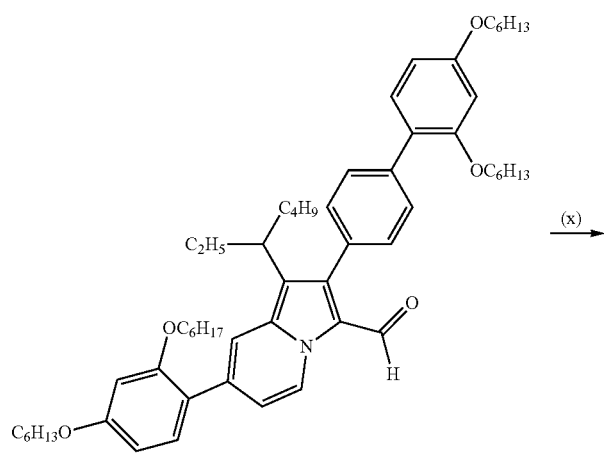
10
(x)

-continued

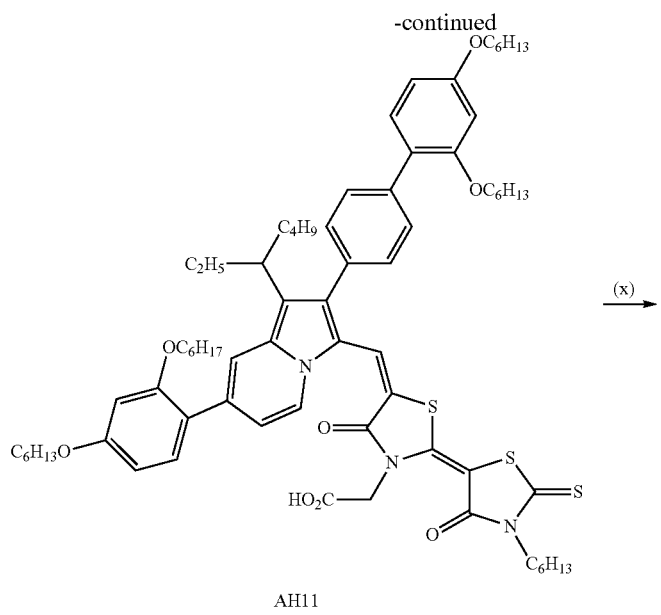

AH11

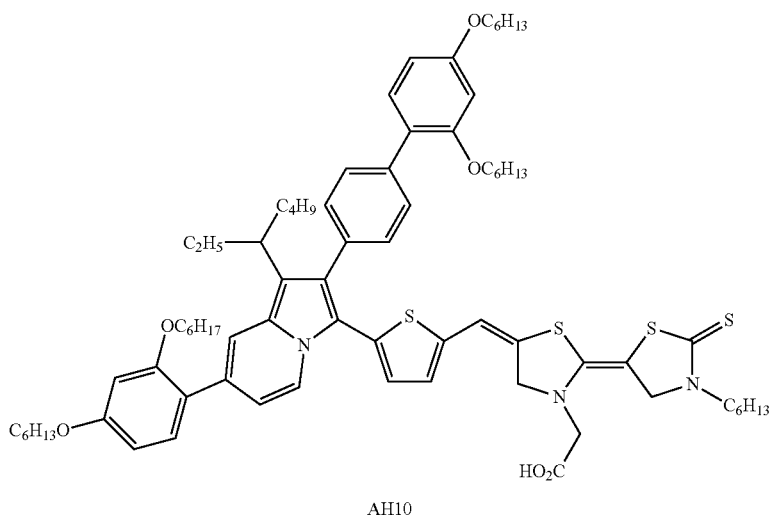

AH10

In the above scheme, examples of synthetic routes to AH10 and AH11 are shown. Conditions: i): a): LDA, THF, −78° C. b): 2-ethylhexylbromide, −78° C. to rt. 1.10 g, 19%, ii): 2,4-bis(hexyloxy)phenylboronic acid, Pd(PPh$_3$)$_4$, Aliquot 336, Na$_2$CO$_3$, H$_2$O, Tol reflux, 3:2.28 g, 69%, 5: 3.30 g, 88%. iii): a): 2,4′-dibromoacetophenone, acetone reflux. b): NaHCO$_3$, HA) reflux, 2.83 g, 79%. iv): thioglycolic acid, MeOH, H$_2$O, 100° C., 1.0 g, 79%, v): a): EtCO$_2$CNS, DBU, rt, MeCN. b): bromoethylacetate, 100° C., 0.56 g 30%, vi): HCl, AcOH, 90° C., 0.035 g, 30%, vii): 5-bromo-2-thiophencarboxaldehyde, PdCl$_2$(PPh$_3$)$_2$, KOAc, NMP, 80° C., 0.086 g, 81%. viii): NCCH$_2$CO$_2$H, piperidine, CHCl$_3$, 90° C. 0.030 g, 67%. ix): 8, piperidine, CHCl$_3$, 90° C., AH10, 0.046 g, 45%, AH11: 0.006 g, 6%. X): DMF, POCl$_3$, DCE, 0° C. to rt, 0.150 g, 50%.

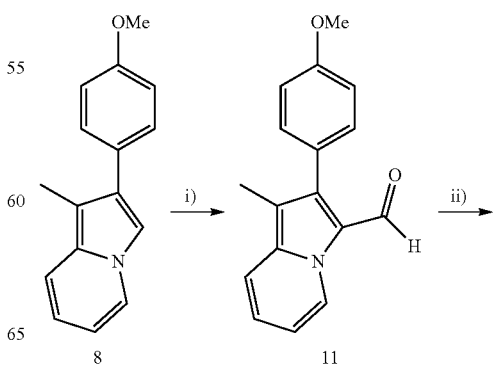

-continued
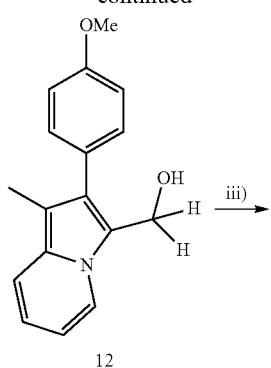
12
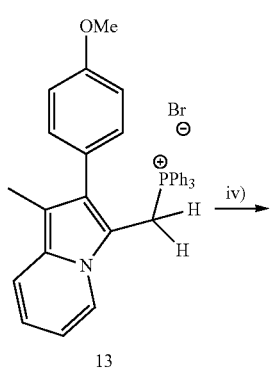
13
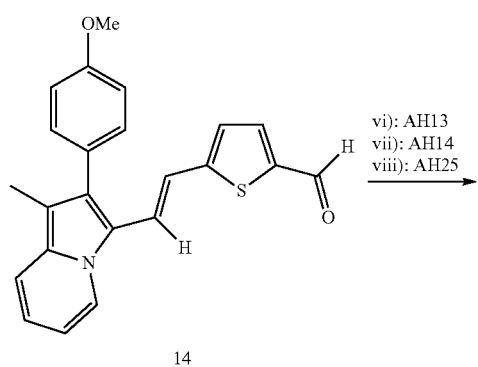
14
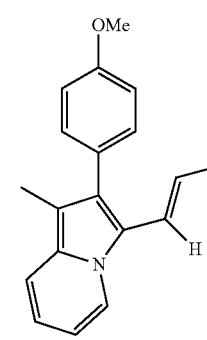
-continued
AH13: R = 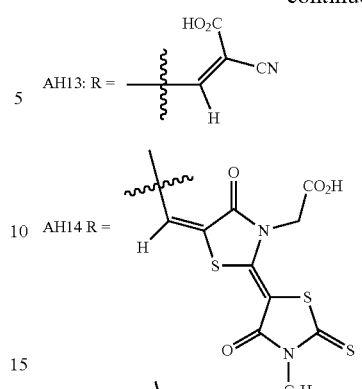
AH14: R =
AH25: R =
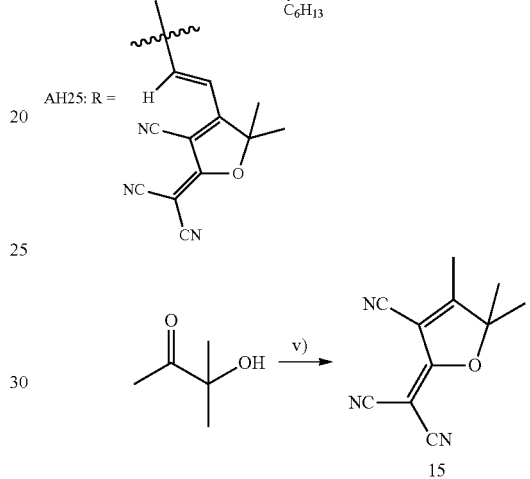
The above scheme shows synthetic route to dyes AH13, AH14, AH25. Conditions: i): DMF, POCl₃, 0.25 g, 90%. ii): LiAlH₄, THF, 0.67 g, 87%. iii): HPPh₃Br, CHCl₃, 0.18 g, quant. iv): 2,5-thiophenebis(carboxaldehyde), LiHMDS, 0.072 g, 80%. v): malonitrile, NaOEt, EtOH, 24 h, 34%. vi): NCCH₂CO₂H, piperidine, CHCl₃, 90° C., 0.005 g, 30%. vii): 8, piperidine, CHCl₃, 90° C., 0.01 g, 10%. viii): 15, 4-aminophenol, toluene, AcOH, 0.051 g, 51%.
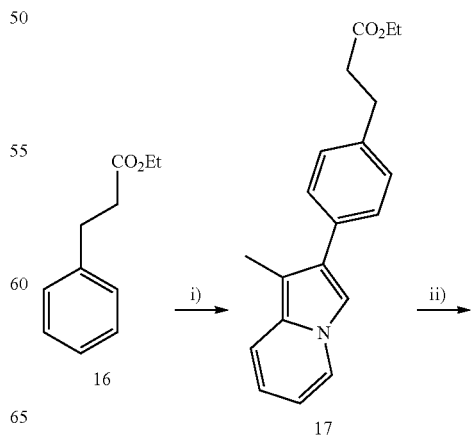

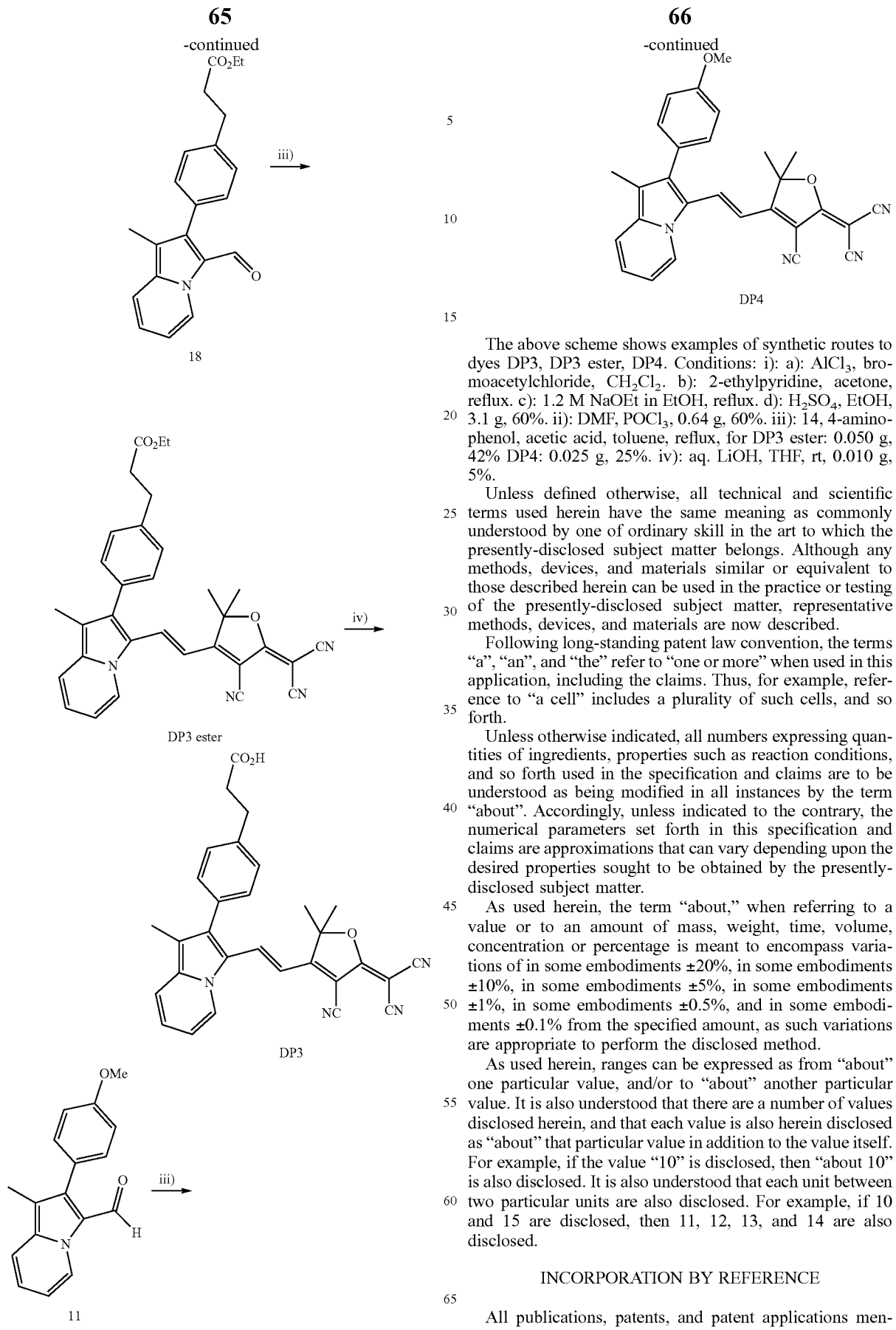

The above scheme shows examples of synthetic routes to dyes DP3, DP3 ester, DP4. Conditions: i): a): $AlCl_3$, bromoacetylchloride, $CH_2Cl_2$. b): 2-ethylpyridine, acetone, reflux. c): 1.2 M NaOEt in EtOH, reflux. d): $H_2SO_4$, EtOH, 3.1 g, 60%. ii): DMF, $POCl_3$, 0.64 g, 60%. iii): 14, 4-aminophenol, acetic acid, toluene, reflux, for DP3 ester: 0.050 g, 42% DP4: 0.025 g, 25%. iv): aq. LiOH, THF, rt, 0.010 g, 5%.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

INCORPORATION BY REFERENCE

All publications, patents, and patent applications mentioned in this specification, including the list below, are herein incorporated by reference to the same extent as if each individual publication, patent, or patent application was specifically and individually indicated to be incorporated by reference.

M. Grätzel et al., *Nature* 1991, 353, 737.
A. Hagfeldt et al., *Chem. Rev.* 2010, 110, 6595
A. Mishra et al., *Angew. Chem. Int. Ed.* 2009, 48, 2474
B. E. Hardin et al., *Nat. Photonics* 2012, 6, 162
J.-Y. Li et al., Wu, *Org. Let.* 2012, 14, 5420
K. Kakiage et al., *Chem. Commun.* 2014, 50, 6379
J. Yang et al., *J. Am. Chem. Soc.* 2014, 136, 5722
J.-H. Yum et al., *Sci. Rep.* 2013, 3, 2446
S. Ahmad et al., *Phys. Chem. Chem. Phys.* 2012, 14, 10631
A. Yella et al., *Chem. Mat.* 2013, 25, 2733
J. H. Delcamp et al., *Angew. Chem. Int. Ed.* 2013, 52, 376.
A. Dualch et al., *Adv. Energy Mater.* 2013, 3, 496.
B. Koszarnma et al., R. C. Matezak, M. Krzeszewski, O. Vakuliuk, J. Klajn, M. Tasior, J. T. Nowicki, D. T. Gryko, *Tetrahedron* 2014, 70, 225.
P. S. Bury et al., WO Patent 055482, 1998.
B. Liu et al., *Chem. Eur. J.* 2012, 18, 1599.
C.-H. Park et al., *Org. Lett.* 2004, 6, 1159.
D. P. Hagberg et al., *J. Org. Chem.* 2007, 72, 9550.
R. Li et al., *J. Phys. Chem. C* 2009, 113, 7469.
T. Dentani et al., *New J. Chem.* 2009, 33, 93.
Q. Chai et al., *ACS Sustainable Chem. & Eng.* 2013, 2, 239.
Q.-Y. Yu et al., *J. Phys. Chem. C* 2011, 115, 22002.
W. Li et al., *ACS App. Mat. Int.* 2012, 4, 1822.
M. Zhang et al., *Energy Environ. Sci.* 2013, 6, 2944.
S. Matthew et al., *Nat. Chem.* 2014, 6, 242.
A. D. Laurent et al., *Int. Quantum Chem.* 2013, 113, 2019.
E. Gabrielsson et al., *Adv. Energy Mater.* 2013, 3, 1647.
S. M. Feldt et al., *J. Am. Chem. Soc.* 2010, 132, 16714.
J. H. Delcamp et al., *Chem. Eur. J.* 2013, 19, 1819.
J. H. Delcamp et al., *J. Chem. Phys.* 1983, 78, 3140.
T. J. Giese et al., *J. Chem. Phys.* 2011, 134, 194103.
A. D. Becke, *J. Chem. Phys.* 1993, 98, 5648.
C. Lee et al., *Phys. Rev. B* 1988, 37, 785.
T. Van Voorhis et al., *J. Chem. Phys.* 1998, 109, 400.
Y. Zhao et al., *J. Chem. Phys.* 2006, 125.
R. Peverati et al., *J. Chem. Theory Comput.* 2012, 8, 2310.
R. Peverati et al., *Phys. Chem. Chem. Phys.* 2012, 14, 13171.
M. Cossi et al., *J. Chem. Phys.* 2001, 115, 4708.
M. M. Mikolajczyk et al., *J. Mol. Model* 2011, 17, 2143.
O. A. Vydrov et al., *J. Chem. Phys.* 2006, 125, 074106.
C. Adamo et al., *J. Chem. Phys.* 1999, 110, 6158.
M. Ernzecrhof et al., *J. Chem. Phys.* 1999, 110, 5029.
J. P. Perdew et al., *Phys. Rev. Lett.* 1996, 77, 3865.
R. D. Bauernschmitt et al., *Chem. Phys. Lett.* 1996, 256, 454.
V. Friedrich et al., *J. Chem. Phys.* 1987, 86, 6425.
M. L. Bode et al., *J. Chem. Soc., Perkin Trans.* 11993, 1809.
J.-F. Soule et al., *J. Am. Chem. Soc.* 2013, 135, 10602.
A. Nuñez et al., *J. Org. Chem.* 2009, 74, 4166.
A. Fürstner et al., *J. Am. Cm. Soc.* 2002, 124, 13856.
O. Bezencon et al., U.S. Pat. No. 7,968,720, 2007.

It will be understood that various details of the presently disclosed subject matter can be changed without departing from the scope of the subject matter disclosed herein. Furthermore, the foregoing description is for the purpose of illustration only, and not for the purpose of limitation.

We claim:

1. A visible absorbing or near infrared dye of the following formula:

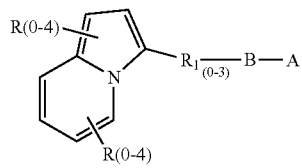

wherein each R is optionally substituted and independently selected from halogen, H, alkyl, amino, O(alkyl), aryl, aryl-$R_{2(0-2)}$, or alkyl-$R_{2(0-2)}$;

$R_1$ is cycloalkyl, phenyl, alkene or alkyne;

wherein when $R_1$ is phenyl it can optionally cyclize with one R to form an additional ring;

$R_2$ is halogen, H, alkyl, amino, O(alkyl), aryl, aryl-$R_{3(0-2)}$, or alkyl-$R_{3(0-2)}$;

$R_3$ is halogen, H, alkyl, amino, O(alkyl), or aryl;

B is a π-bridge; and

A is an acceptor including at least one terminal group consisting of $CO_2H$ or $PO_3H_2$.

2. The dye of claim 1, wherein $R_1$ is a substituted or unsubstituted phenyl.

3. The dye of claim 1, of the following formula:

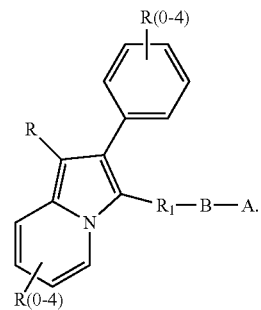

4. The dye of claim 1, of the following formula:

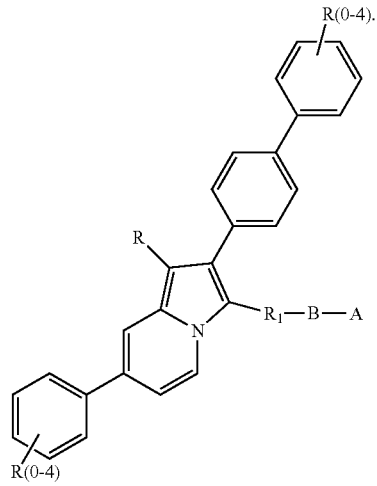

5. The dye of claim 1, of the following formula:

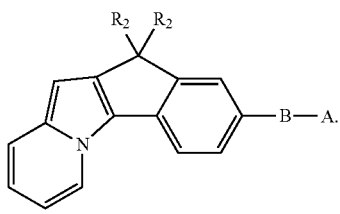

6. The dye of claim 1, of the following formula:

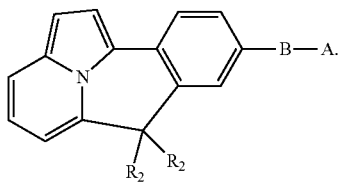

7. The dye of claim 1, wherein one or more R groups are independently selected from phenyl, hexyl, pentyl, methyl, O(methyl),

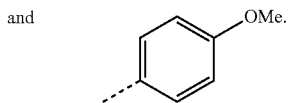

8. The dye of claim 1, of the following formula:

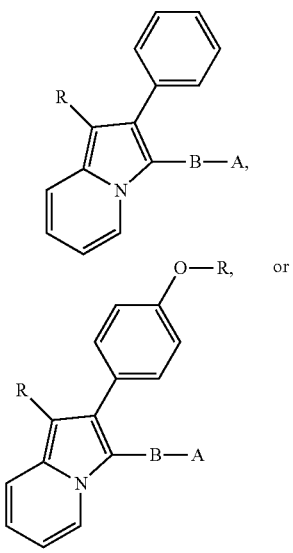

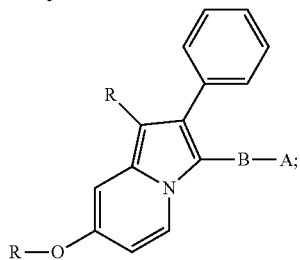

wherein R is alkyl.

9. The near infrared dye of claim 8, of the following formula:

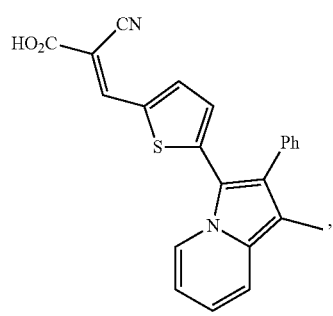

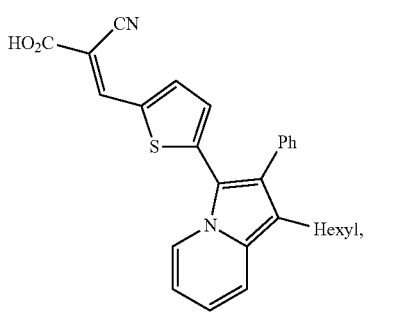

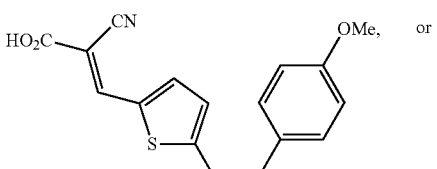

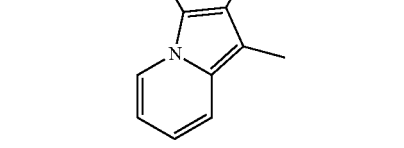

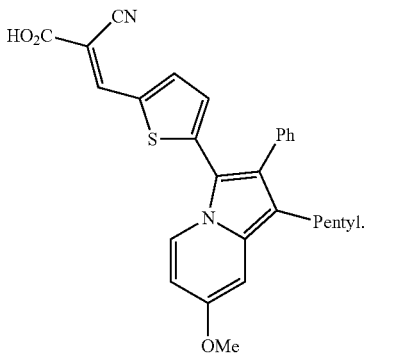

10. The dye of claim 1, wherein the electron acceptor includes the formula:

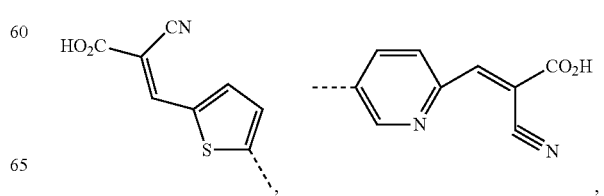

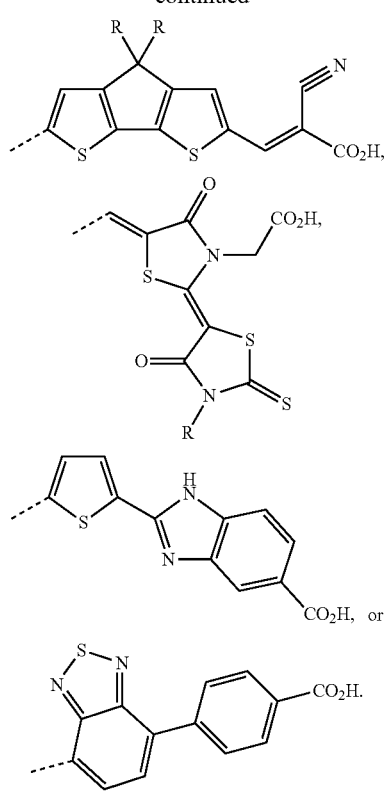
11. A compound of the following formula:
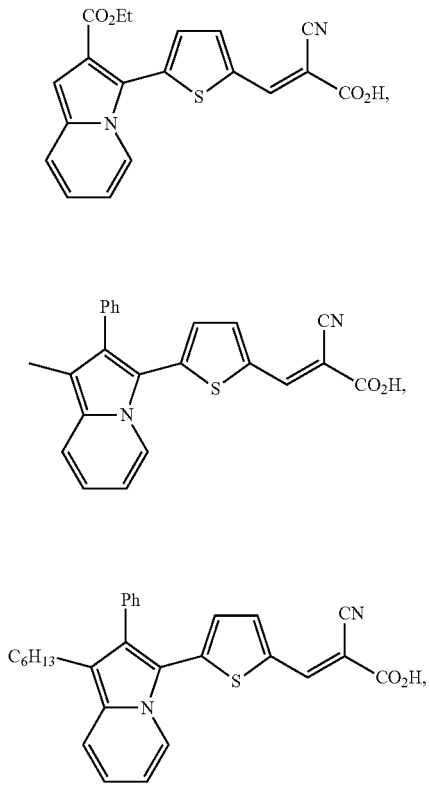
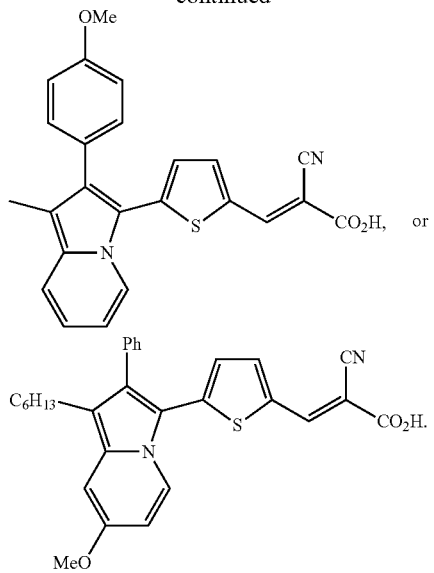
12. A compound of the following formula:
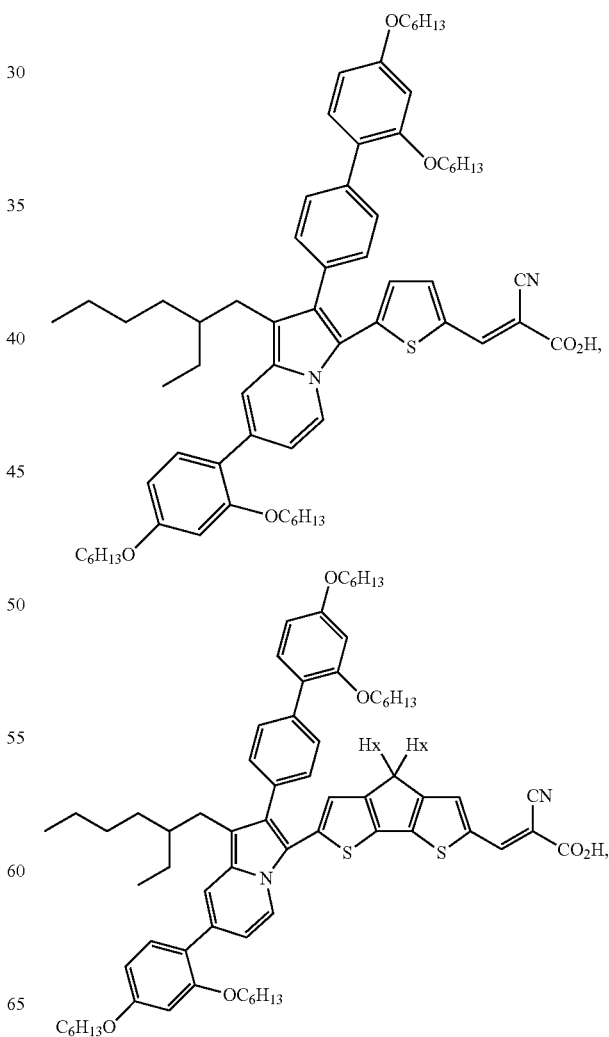

-continued
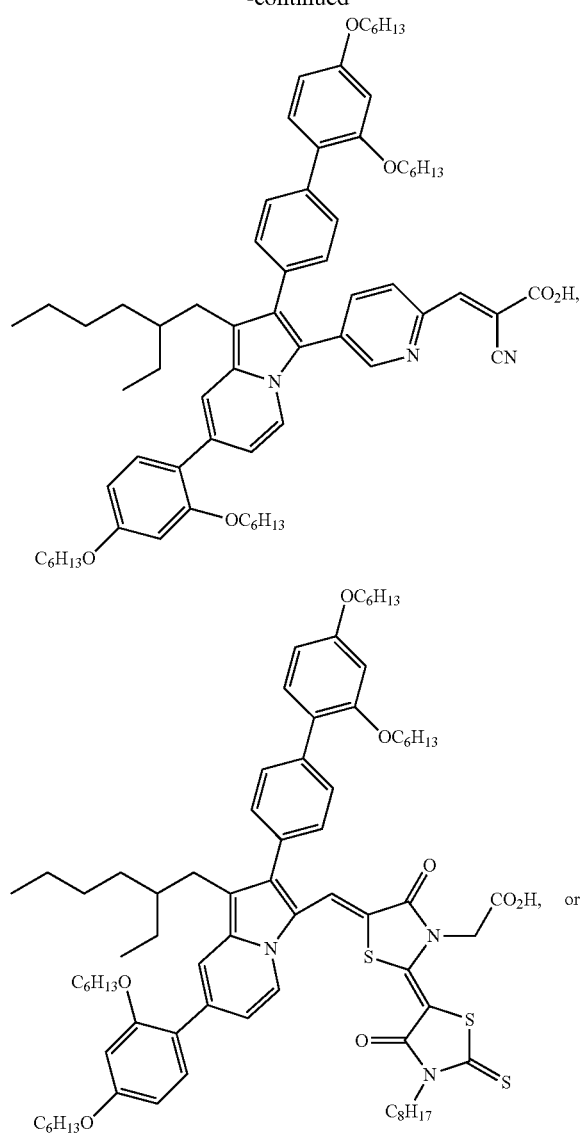
13. A compound of the following formula:
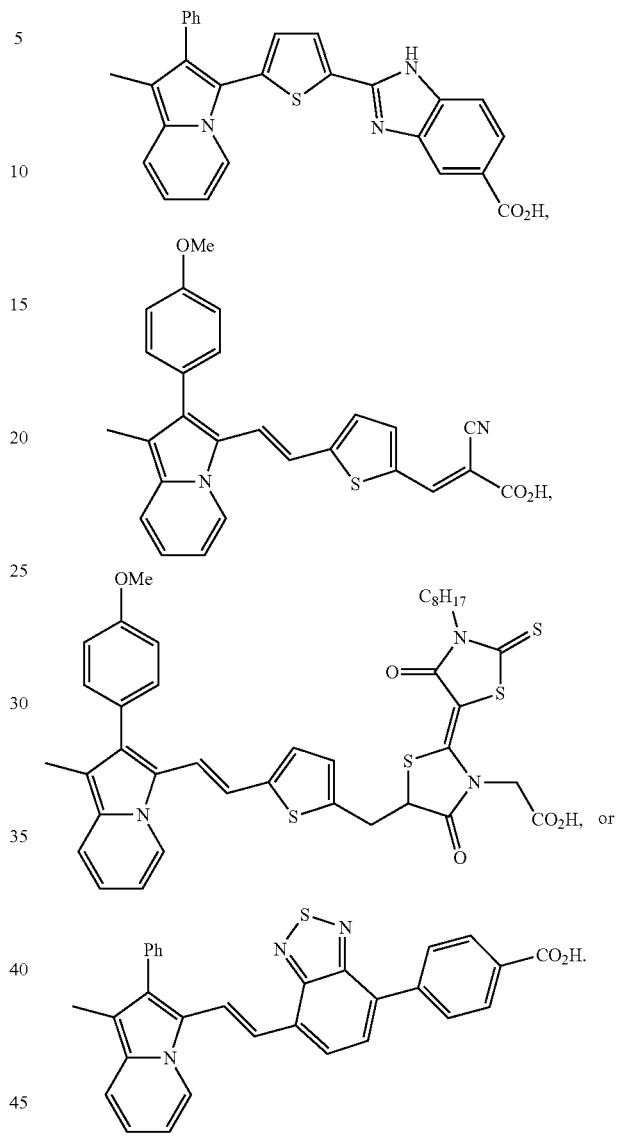
14. A compound of the following formula:
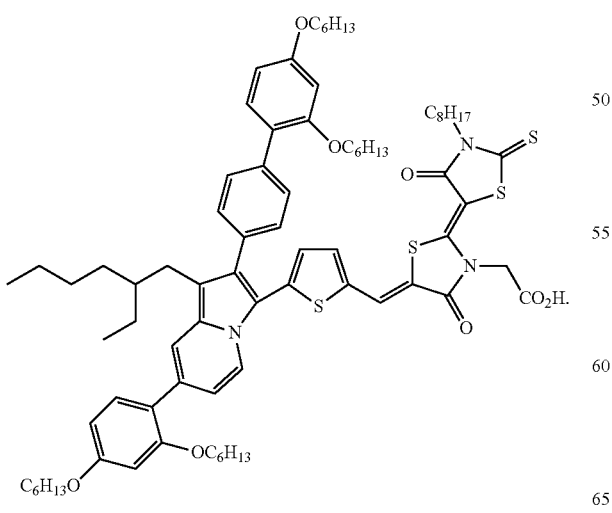
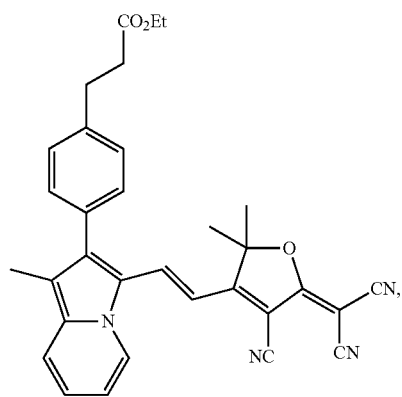

-continued
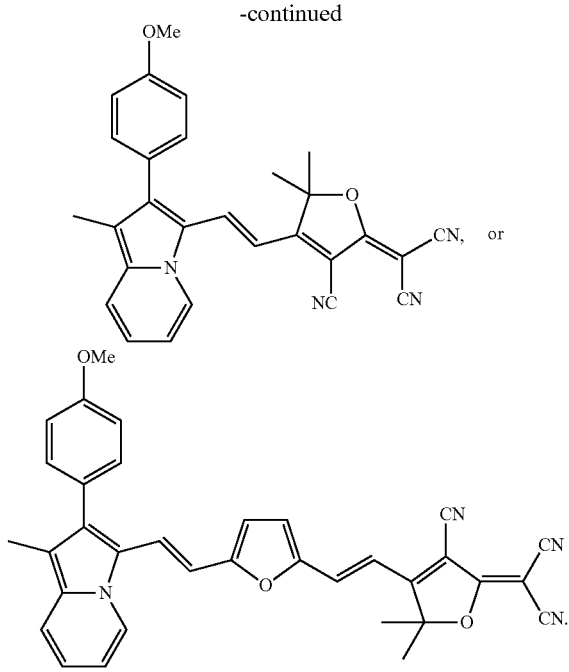
15. A dye-sensitized solar cell, comprising:
an anode plate and a cathode plate; a dye of claim 1;
a semiconducting oxide;
a redox couple or charge transport material.
16. The solar cell of claim 15, wherein the semiconducting oxide is $TiO_2$, ZnO, or $SnO_2$.
17. The solar cell of claim 15, wherein the dye is of the following formula:
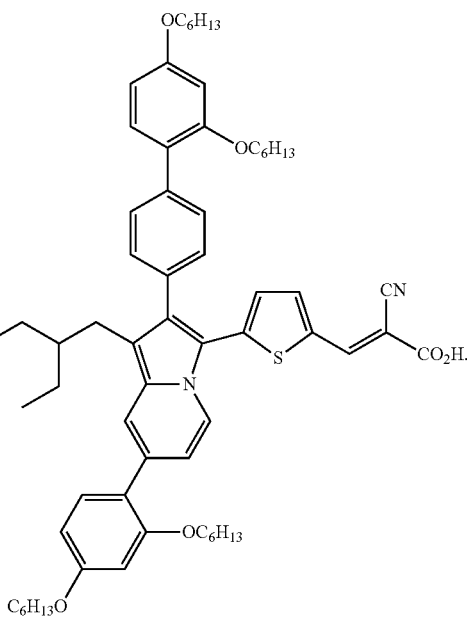
* * * * *